(12) United States Patent
Jin et al.

(10) Patent No.: US 10,077,507 B2
(45) Date of Patent: Sep. 18, 2018

(54) SOLUTION GROWTH OF SINGLE-CRYSTAL PEROVSKITE STRUCTURES

(71) Applicant: Wisconsin Alumni Research Foundation, Madison, WI (US)

(72) Inventors: Song Jin, Madison, WI (US); Yongping Fu, Madison, WI (US); Fei Meng, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 81 days.

(21) Appl. No.: 14/954,442

(22) Filed: Nov. 30, 2015

(65) Prior Publication Data

US 2017/0152608 A1    Jun. 1, 2017

(51) Int. Cl.
| | |
|---|---|
| C07F 7/00 | (2006.01) |
| C30B 7/14 | (2006.01) |
| C30B 29/60 | (2006.01) |
| C07F 7/24 | (2006.01) |
| H01L 51/00 | (2006.01) |
| C30B 29/12 | (2006.01) |
| H01L 51/50 | (2006.01) |

(52) U.S. Cl.
CPC .............. *C30B 7/14* (2013.01); *C07F 7/24* (2013.01); *C30B 29/12* (2013.01); *C30B 29/60* (2013.01); *H01L 51/0084* (2013.01); *H01L 51/5012* (2013.01)

(58) Field of Classification Search
CPC  C30B 7/14; C30B 29/54; C30B 29/60; C30B 29/64; C07F 7/22; C07F 7/24; C07F 7/30; H01L 51/0084
USPC .......................................................... 556/81
See application file for complete search history.

(56) References Cited

PUBLICATIONS

Sutherland et al., ACS Nano, vol. 8, No. 10, pp. 10947-10952 (2014).*
Fu, A. et al., Lower threshold for nanowire lasers, Nat. Mater. 14, Jun. 2015, pp. 557-558.
Jeon, N. J. et al., Compositional engineering of perovskite materials for high-performance solar cells, Nature 517, Jan. 22, 2015, pp. 476-480.
Yang, W. S. et al., High-performance photovoltaic perovskite layers fabricated through intramolecular exchange, Science 348, Jun. 12, 2015, pp. 1234-1237.
Deschler, F. et al., High Photoluminescence Efficiency and Optically Pumped Lasing in Solution-Processed Mixed Halide Perovskite Semiconductors, J. Phys. Chem. Lett. 5, Mar. 24, 2014, pp. 1421-1426.
Xing, G. C. et al., Low-temperature solution-processed wavelength-tunable perovskites for lasing, Nat. Mater. 13, Mar. 16, 2014, pp. 476-480.
Stranks, S. D. et al., Enhanced Amplified Spontaneous Emission in Perovskites Using a Flexible Cholesteric Liquid Crystal Reflector, Nano Lett. 15, May 19, 2015, pp. 4935-4941.
Suárez, I. et al., Polymer/Perovskite Amplifying Waveguides for Active Hybrid Silicon Photonics, Adv. Mater. 27, Aug. 31, 2015, pp. 6157-6162.
Zhang, Q. et al., Room-Temperature Near-Infrared High.Q Perovskite Whispering-Gallery Planar Nanolasers, Nano Lett. 14, Aug. 14, 2014, pp. 5995-6001.
Xing, J. et al., Vapor Phase Synthesis of Organometal Halide Perovskite Nanowires for Tunable Room-Temperature Nanolasers, Nano Lett. 15, Jun. 4, 2015, pp. 4571-4577.
Sutherland, B. R. et al., Conformal Organohalide Perovskites Enable Lasing on Spherical Resonators, ACS Nano 8, Oct. 14, 2014, pp. 10947-10952.
Liao, Q. et al., Perovskite Microdisk Microlasers Self-Assembled from Solution, Adv. Mater. 27, Apr. 22, 2015, pp. 3405-3410.
Ha, S. T. et al., Synthesis of Organic-Inorganic Lead Halide Perovskite Nanoplatelets: Towards High-Performance Perovskite Solar Cells and Optoelectronic Devices, Adv. Opt. Mater. 2, May 23, 2014, pp. 838-844.
Im, J. H. et al., Nanowire Perovskite Solar Cell, Nano Lett. 15, Feb. 24, 2015, pp. 2120-2126.
Zhuo, S. et al., Self-Template-Directed Synthesis of Porous Perovskite Nanowires at Room Temperature for High-Performance Visible-Light Photodetectors, Angew. Chem. 54, Mar. 16, 2015, pp. 5693-5696.
Chen, Z. et al., Shape-controlled synthesis of organolead halide perovskite nanocrystals and their tunable optical absorption, Mater. Res. Express 1 015034, Mar. 11, 2014, pp. 1-12.
Yongping Fu et al., Single Crystal $CH_3NH_3PbI_3$ and $CH_3NH_3PbBr_3$ Perovskite Nanowires, Nanorods and Nanoplates with Room-Temperature Photoluminescence, Abstract for Materials Research Society Conference, Boston, MA , Sep. 1, 2014, pp. 1.
Yongping Fu et al., Single Crystalline Lead Halide Perovskite Nanomaterials, Poster Presentation for Materials Research Society Conference, Boston, MA, Dec. 1, 2014, pp. 1.
Gregor Kieslich et al., Solid-state principles applied to organic-inorganic perovskites: new tricks for an old dog, Chem. Sci. 5, Aug. 15, 2014, pp. 4712-4715.
Gregor Kieslich et al., An extended Tolerance Factor approach for organic-inorganic perovskites, Chem. Sci. 6, Apr. 14, 2015, pp. 3430-3433.

(Continued)

*Primary Examiner* — Clinton Brooks
*Assistant Examiner* — Kofi Adzamli
(74) *Attorney, Agent, or Firm* — Bell & Manning, LLC

(57) ABSTRACT

A method for growing single-crystal perovskite structures comprises immersing a film of a metal precursor compound on a surface of a substrate, the metal precursor compound comprising a metal ion B, in a solution comprising a cation precursor compound, the cation precursor compound comprising a cation ion A and an anion X, at a concentration of the cation precursor compound, a growth time, and a growth temperature sufficient to dissolve the film to release the metal ion B to form a complex with the anion X and sufficient to induce recrystallization of the complex with the cation ion A to form a plurality of single-crystal perovskite structures composed of A, B and X. The single-crystal perovskite structures, devices incorporating the same, and methods of using the devices are also provided.

21 Claims, 38 Drawing Sheets

(56) References Cited

PUBLICATIONS

Zhang et al., Ultrasmooth organic-inorganic perovskite thin-film formation and crystallization for efficient planar heterojunction solar cells, Nature Communications 6, Article No. 6142, Jan. 30, 2015, pp. 1-10.

Yongping Fu, et al., Solution Growth of Single Crystal Methylammonium Lead Halide Perovskite Nanostructures for Optoelectronic and Photovoltaic Applications , J. Am. Chem. Soc. 137 , Apr. 14, 2015, pp. 5810-5818.

Haiming Zhu et al., Lead halide perovskite nanowire lasers with low lasing thresholds and high quality factors, Nature Materials vol. 14, Apr. 13, 2015, pp. 636-643.

Feng Zhu et al., Shape Evolution and Single Particle Luminescence of Organometal Halide Perovskite Nanocrystals, ACS Nano 9 (3), Feb. 9, 2015, pp. 2948-2959.

Kangning Liang et al., Synthesis and Characterization of Organic-Inorganic Perovskite Thin Films Prepared Using a Versatile Two-Step Dipping Technique, Chem. Mater. 10, Jan. 19, 1998, pp. 403-411.

Shuang Yang et al., Formation Mechanism of Freestanding CH3NH3PbI3 Functional Crystals: In Situ Transformation vs Dissolution-Crystallization, Chem. Mater. 26, Nov. 14, 2014, pp. 6705-6710.

\* cited by examiner

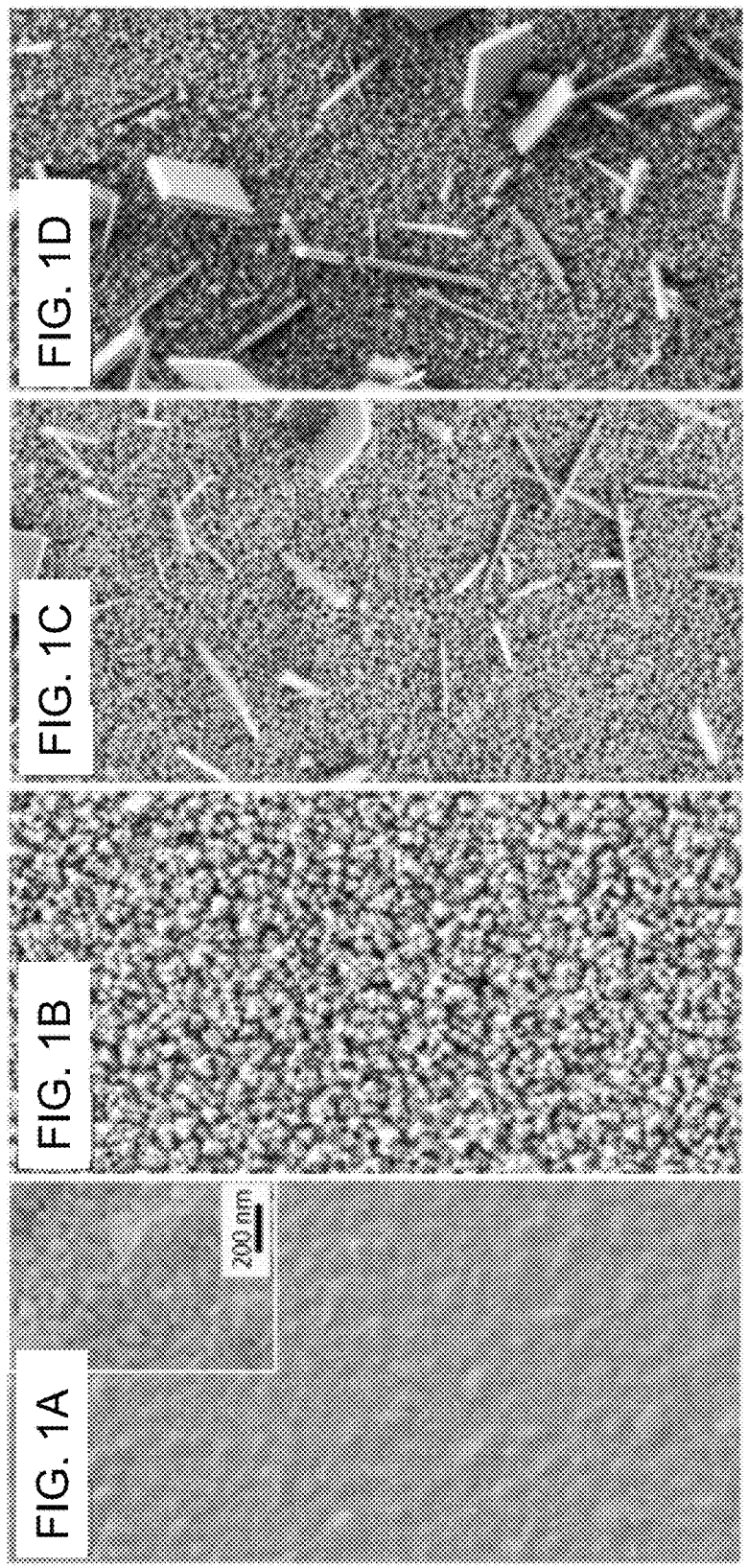

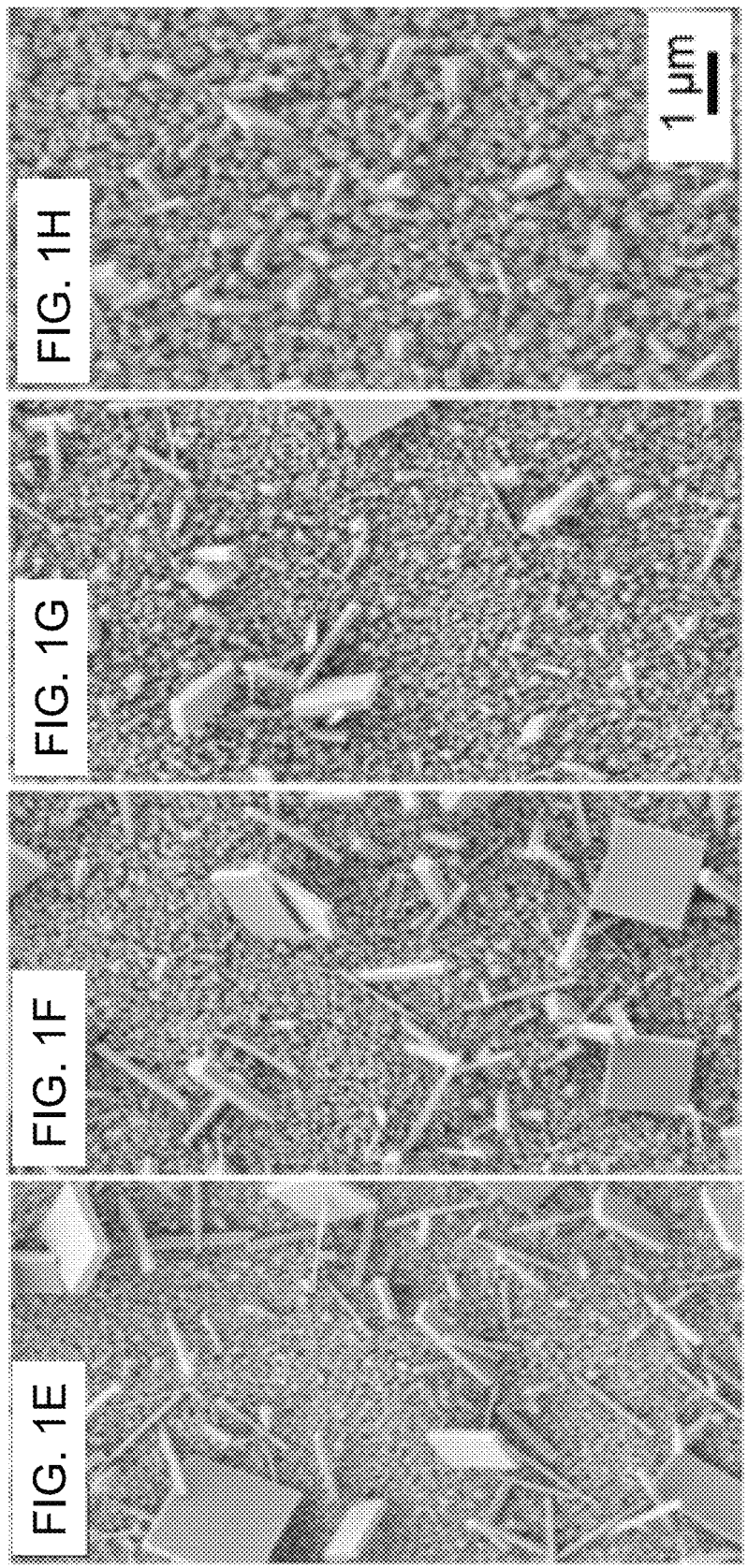

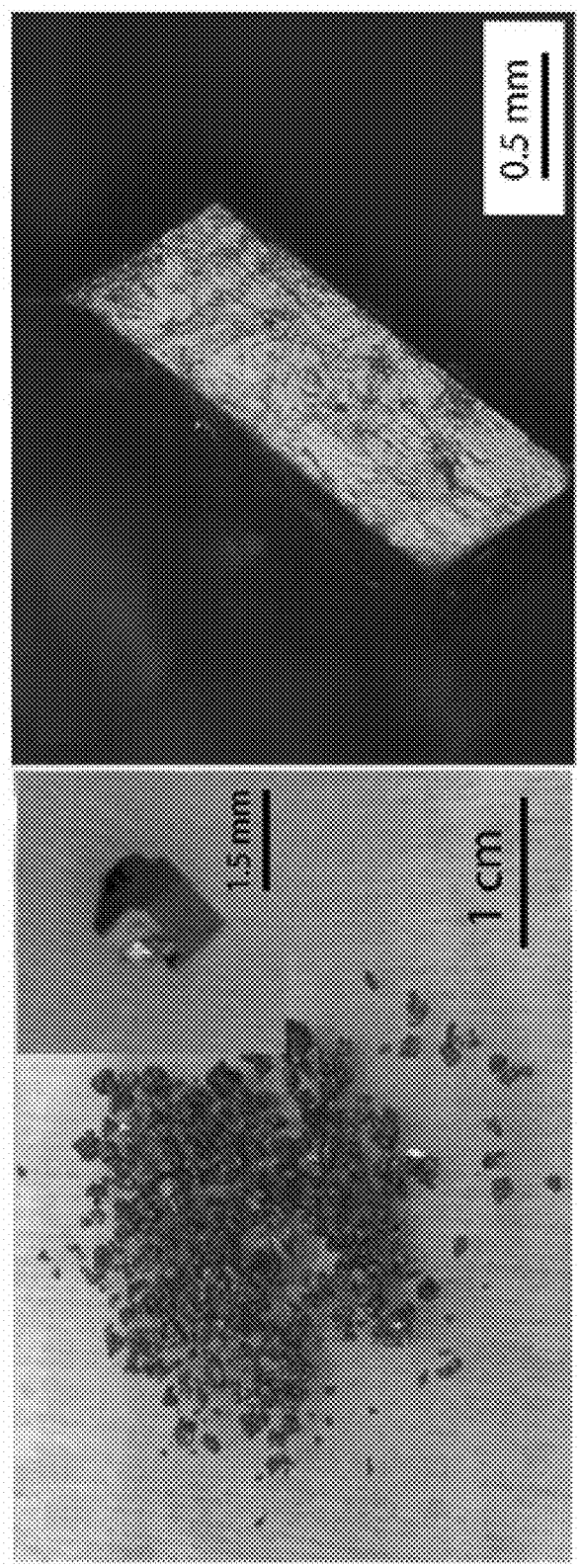

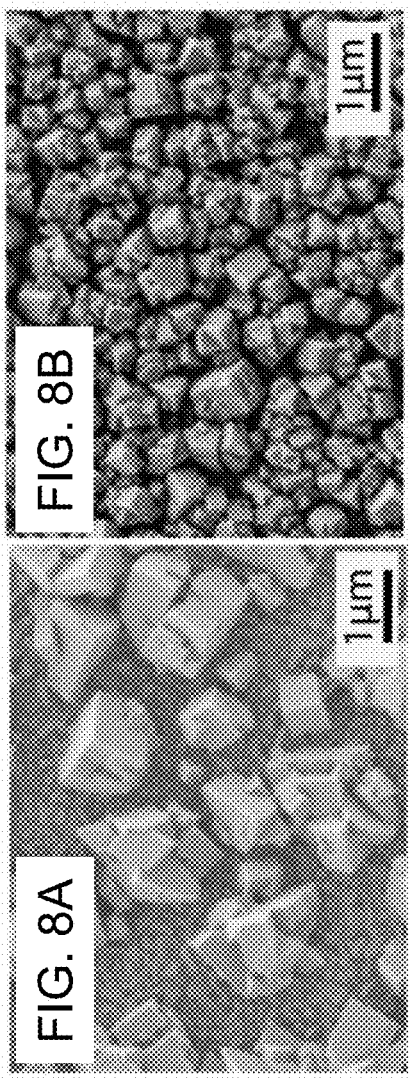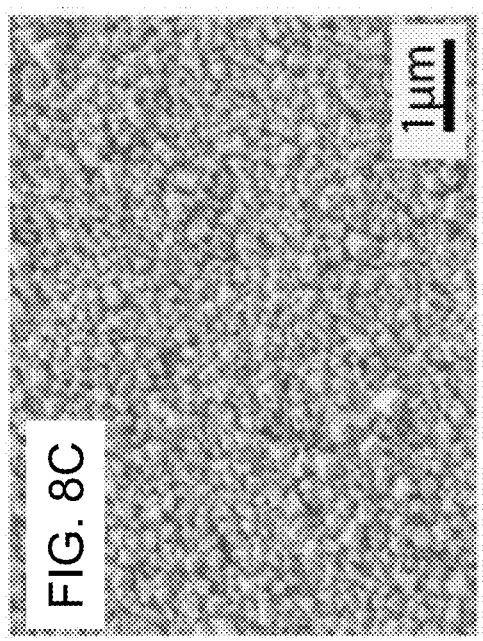

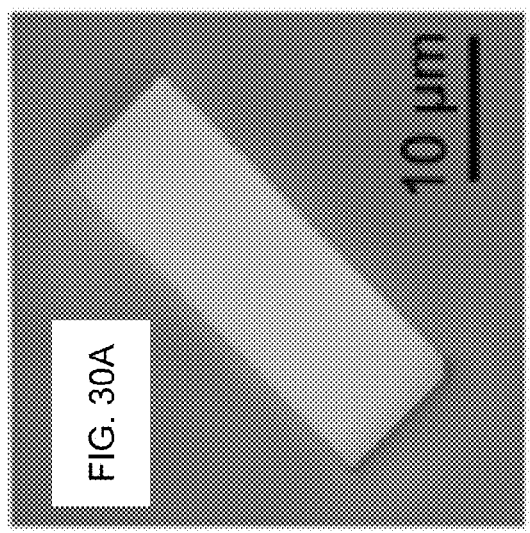 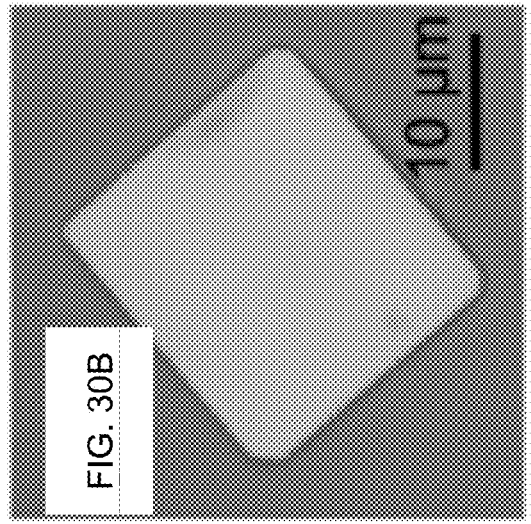

SOLUTION GROWTH OF SINGLE-CRYSTAL PEROVSKITE STRUCTURES

REFERENCE TO GOVERNMENT RIGHTS

This invention was made with government support under DE-SC0002162 awarded by the US Department of Energy. The government has certain rights in the invention.

BACKGROUND

Hybrid organic-inorganic perovskite materials have attracted interest as promising materials for both photovoltaic and optoelectronic applications. Three-dimensional (3D) organic-inorganic hybrid perovskites generally adopt the formula of $ABX_3$, wherein A is an organic cation, B is a metal ion and X is a halide anion. Two-dimensional (2D) organic-inorganic hybrid perovskites generally adopt the formula of $A_2BX_4$. These 2D materials are layered structures in which each layer consists of an extended network of corner-sharing metal halide octahedral $[MX_6]^{4-}$ and two layers of organic cations on both sides to balance the charge.

Methylammonium lead iodide perovskite, $CH_3NH_3PbI_3$ ($MAPbI_3$), is a 3D perovskite material emerging as a "superstar" semiconductor for cost-effective photovoltaic (PV) applications. It is a semiconductor with a suitable and direct optical band gap (1.57 eV), a high optical absorption coefficient ($\alpha=10^4$-$10^5$ cm$^{-1}$ for hv>1.7 eV), and a long electron/hole diffusion length (a few μm) even in solution-processed polycrystalline thin films, making $MAPbI_3$ advantageous in photovoltaic applications. A variety of methods have been used to prepare $MAPbI_3$ thin films for photovoltaic devices, including spin coating from a $MAPbI_3$ solution, sequential solution deposition, vapor co-evaporation, and vapor-assisted solution conversion. However, these techniques usually produce polycrystalline $MAPbI_3$ perovskite thin films. Crystallinity, shape and size all affect the ability to make use of the $MAPbI_3$ in electronic, optoelectronic and photonic applications.

Formamidinium lead iodide perovskite, $CH(NH_2)_2PbI_3$ ($FAPbI_3$), is another 3D perovskite which is receiving attention in the photovoltaic research community, although successful incorporation of this material into viable optoelectronic devices other than solar cells has been limited. Use of formamidinium in place of methylammonium leads to a semiconductor with a slightly lower bandgap of 1.47 eV, as well as better temperature and moisture stability.

Similar to 3D methylammonium lead triiodide perovskite, the 2D layered perovskite thin films may be prepared by similar methods. Such 2D perovskites have been used in electroluminescence (EL) devices, scintillation detectors for X-ray radiation, optical microcavities, and exciton or bi-exciton lasing. However, the device performance and photostability of the 2D perovskites has been limited, at least in part due to poor crystal quality.

Semiconductor nanowire (NW) lasers, due to their ultra-compact physical sizes, highly localized coherent output, and efficient waveguiding, are promising building blocks in fully integrated nanoscale photonic and optoelectronic devices. Each NW can serve as waveguide along the axial direction while the two end facets form a Fabry-Perot cavity for optical amplification. Optically pumped lasing has been demonstrated from a number of classic inorganic semiconductor NWs, such as ZnO, GaN, CdS and GaAs with emission from the UV to the near-IR regions. One of the major obstacles limiting potential applications of semiconductor NW lasers is the high threshold carrier density required for lasing. The high lasing threshold means low quantum efficiency; this not only makes key technical advancement, such as electrically driven lasing and integration into optoelectronic devices difficult, but also imposes fundamental limits due to the onset of Auger recombination losses. Despite considerable efforts to improve NW quality using demanding growth conditions that usually require high temperature and high vacuum and core/shell structures to reduce surface recombination, lasing thresholds in NW lasers remain unsatisfactorily high.

SUMMARY

Provided are solution growth methods for growing single-crystal perovskite structures. Also provided are the single-crystal perovskite structures, devices comprising the single-crystal perovskite structures and related methods.

In one aspect, methods for growing single-crystal perovskite structures are provided. In one embodiment, the method comprises immersing a film of a metal precursor compound on a surface of a substrate, the metal precursor compound comprising a metal ion B, in a solution comprising a cation precursor compound, the cation precursor compound comprising a cation ion A and an anion X, at a concentration of the cation precursor compound, a growth time, and a growth temperature sufficient to dissolve the film to release the metal ion B to form a complex with the anion X and sufficient to induce recrystallization of the complex with the cation ion A to form a plurality of single-crystal perovskite structures composed of A, B and X.

In another aspect, single-crystal perovskite structures are provided. In one embodiment, a single-crystal perovskite structure is configured to produce lasing action when under the influence of an applied electromagnetic field, wherein the perovskite has formula $ABX_3$, wherein A is a protonated amine or an alkali metal ion; B is selected from a post-transition metal, a metalloid, a transition metal, an alkaline earth metal, and a lanthanide; and X is selected from a halide, $RCOO^-$, wherein R is H or an alkyl group, $CN^-$, $N_3^-$, and $BH_4^-$; or the perovskite has formula $A_2BX_4$, wherein A is selected from $C_{n1}H_{2n1+1}NH_3^+$, wherein $n_1$ is 3 or greater; $C_{n2}H_{2n2-1}C_{n3}H_{2n3}NH_3^+$, wherein $n_2$ is 3 or greater and wherein $n_3$ is 0 or greater; and $C_6H_5C_{n4}H_{2n4}NH_3^+$, wherein $n_4$ is 0 or greater; B is selected from a post-transition metal, a metalloid, a transition metal, an alkaline earth metal, and a lanthanide; and X is selected from a halide, $RCOO^-$, wherein R is H or an alkyl group, $CN^-$, $N_3^-$, and $BH_4^-$.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

FIGS. 1A-1H show the morphologies of as-grown $MAPbI_3$ nanostructures using $PbI_2$ and different concentrations of MAI/IPA solutions at a reaction time of 10 min. FIG. 1A shows a SEM image of pre-deposited $PbI_2$ film on FTO substrate. FIGS. 1B-1H show SEM images of as-grown $MAPbI_3$ nanostructures grown using condition of 10 mg/mL, 20 mg/mL, 30 mg/mL, 40 mg/mL, 50 mg/mL, 60 mg/mL and 70 mg/mL MAI/IPA solution, respectively. All the images share the same scale bar shown in FIG. 1H.

FIGS. 3A-3D show the SEM images of as-grown MAPbI$_3$ perovskite nanostructures at a reaction time of 1 min, 60 min, 3 h 40 min, and 19 h 30 min. FIGS. 3E and 3F show more SEM images with higher magnification of as-grown perovskite nanostructures at the 19 h 30 min reaction time.

FIG. 5A shows a low-resolution TEM image of a MAPbI$_3$ NW; the inset is the corresponding SAED pattern along ZA [110]. FIG. 5B shows a low-resolution TEM image of a MAPbI$_3$ nanoplate; inset is the corresponding SAED pattern along ZA [001]. FIG. 5C is a high-resolution TEM image of a single-crystal MAPbI$_3$ nanoplate.

FIG. 6A shows the visible absorption spectrum of MAPbI$_3$ film synthesized from a 40 mg/mL MAI/IPA solution and 30 min reaction time in comparison with the confocal microscopy photoluminescence of a single nanoplate and bulk crystal excited by a 532 nm laser source, respectively. The inset shows a dark-field optical microscopy image of a single MAPbI$_3$ nanoplate with a size of about 2 μm×3 μm. FIG. 6B shows the carrier decay dynamics of MAPbI$_3$ perovskite nanostructures (transmission mode) and bulk single crystal (reflection mode) at 795 nm under a pump fluence of 9.8 μJ/cm$^2$.

FIGS. 7A-7B show photographs of bulk single crystals. FIG. 7A shows optical images of bulk MAPbI$_3$ crystals. FIG. 7B shows a dark-field image of a MAPbI$_3$ single crystal.

FIGS. 8A-8C show structural characterizations of nanostructured MAPbI$_3$ films converted at low MAI precursor concentrations. SEM images of nanostructured MAPbI$_3$ films converted at different MAI concentrations are shown, including 5 mg/mL (FIG. 8A), 7.5 mg/mL (FIG. 8B) and 10 mg/mL (FIG. 8C) with a conversion time of 2 min. (d) The PXRD patterns of these as-converted MAPbI$_3$ films, insets are the corresponding optical images.

FIGS. 30A and 30B show optical images of individual shape-defined nanoplatelets with different dimensions on silicon substrate.

FIG. 32A shows a (PEA)$_2$PbI$_4$ microwire. FIG. 32B shows a (PEA)$_2$PbBr$_{0.6}$I$_{3.4}$ rectangular nanoplatelet. FIG. 32C shows a (PEA)$_2$PbBr$_{2.4}$I$_{1.6}$ hexagonal nanoplatelet. FIG. 32D shows a (PEA)$_2$PbBr$_{3.1}$I$_{0.9}$ rectangular nanoplatelet. FIG. 32E shows a (PEA)$_2$PbBr$_{3.1}$I$_{0.9}$ elongated hexagonal nanoplatelet.

DETAILED DESCRIPTION

Figure 2:
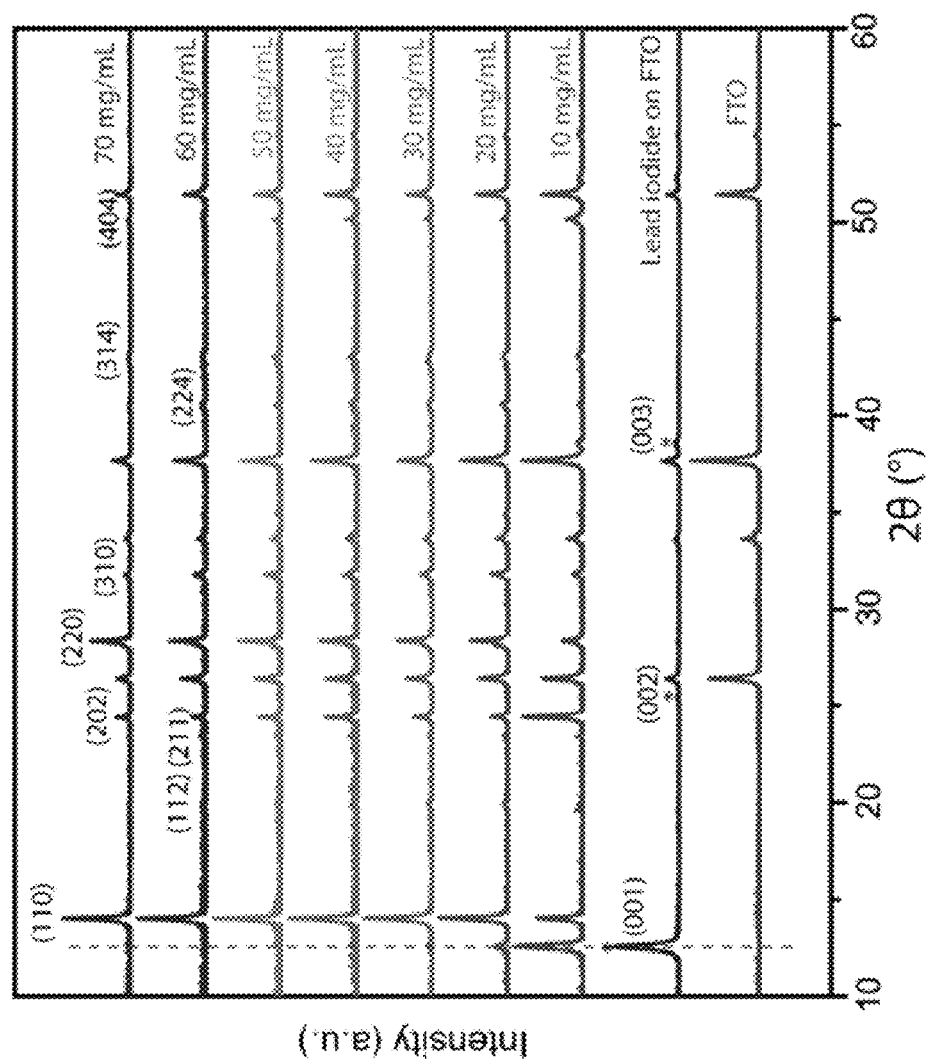
FIG. 2 shows the PXRD patterns of as-grown MAPbI$_3$ nanostructures using PbI$_2$ and different concentrations of MAI/IPA solutions at a reaction time of 10 min, in comparison with lead iodide and FTO substrate.

Provided are solution growth methods for growing single-crystal perovskite structures. Also provided are the single-crystal perovskite structures, devices comprising the single-crystal perovskite structures and related methods.

Although growth methods have been developed in an attempt to capitalize on the advantageous properties of certain hybrid organic-inorganic perovskite materials, such methods have produced materials having sub-optimal quality, structure and properties which have limited or prevented effective use in optical electronic devices. By contrast, the disclosed growth methods offer a simple, fast, scalable, controllable and cost-effective strategy for achieving perovskite structures, including hybrid organic-inorganic perovskites structures, that have a crystalline quality, shape and size which renders them practically suitable for use in a variety of electronic, optoelectronic and photonic applications, including light emitting and lasing applications. The unique combination of structural features of at least some embodiments of the disclosed hybrid organic-inorganic perovskite structures provides them with superior properties (e.g., low defect density, long carrier lifetime and carrier diffusion time, room temperature photoluminescence with high quantum yield) and additional properties (e.g., laser emission) as compared to hybrid organic-inorganic perovskite materials formed using conventional synthesis methods. The disclosed methods are based on low temperature dissolution of a film of a metal precursor compound in a solution of a cation precursor compound and recrystallization of metal anion complexes to form to single-crystal perovskite structures.

The perovskite from which the single-crystal perovskite structures are composed may have Formula I, $$ABX_3 \quad \text{(Formula I)}.$$

In Formula I, A (the cation) may be a protonated amine or an alkali metal ion; B (the metal) may be a divalent metal ion; and X (the anion) may be an anion capable of bonding to B. A variety of protonated amines may be used, e.g., a primary ammonium, a secondary ammonium, a tertiary ammonium, a quaternary ammonium, or an iminium. Suitable illustrative protonated amines include, e.g., NH$_4^+$ (ammonium); CH$_3$NH$_3^+$ (methylammonium); NH$_3$OH$^+$ (hydroxylammonium); NH$_3$NH$_2^+$ (hydrazinium); (CH$_2$)$_3$NH$_2^+$ (azetidinium); CH(NH$_2$)$_2^+$ (formamidinium); C$_3$N$_2$H$_5^+$ (imidazolium); (CH$_3$)$_2$NH$_2^+$ (dimethylammonium); (CH$_3$CH$_2$)NH$_3^+$ (ethylammonium); (NH$_2$)$_3$C$^+$ (guanidinium); (CH$_3$)$_4$N$^+$ (tetramethylammonium); C$_3$H$_4$NS$^+$ (thiazolium); NC$_4$H$_8^+$ (3-pyrollinium); and C$_7$H$_7^+$ (tropylium). Alkali metal ions, such as Cs$^+$, can be used as A.

A variety of divalent metal ions may be used, e.g., a post-transition metal or a metalloid such as Ge$^{2+}$, Sn$^{2+}$, Pb$^{2+}$; a transition metal such as Mn$^{2+}$, Fe$^{2-}$, Co$^{2+}$, Ni$^{2+}$, Pd$^{2+}$, Pt$^{2+}$, Cu$^{2+}$, Zn$^{2+}$, Cd$^{2+}$, Hg$^{2+}$; an alkaline earth metal such as Be$^{2+}$, Mg$^{2+}$, Ca$^{2-}$, Sr$^{2+}$, Ba$^{2+}$; and a lanthanide such as Eu$^{2+}$, Tm$^{2+}$, Yb$^{2+}$. However, in some embodiments, the divalent metal ion is not an alkaline earth metal.

A variety of anions may be used, e.g., a halide such as F$^-$, Cl$^-$, Br$^-$, I$^-$; an organic anion such as RCOO$^-$, wherein R is H or an alkyl group (e.g., methyl or ethyl); CN$^-$; N$_3^-$; and BH$_4^-$. In some embodiments, the anion may be oxygen (O).

Formula I encompasses alloy perovskites, i.e., perovskites which include more than one type of cation (A) in varying relative amounts (provided the sum of the amounts is 1), more than one type of metal (B) in varying relative amounts (provided the sum of the amounts is 1), more than one type of anion (X) in varying relative amounts (provided the sum of the amounts is 3), or combinations thereof. By way of illustration, alloy perovskites having formula (A$_1$)$_x$(A$_2$)$_{1-x}$B (X$_1$)$_y$(X$_2$)$_{3-y}$, wherein x ranges from 0 to 1 and y ranges from 0 to 3 are encompassed by Formula I. As another illustration, alloy perovskites having formula (A$_1$)$_x$(A$_2$)$_{1-x}$ (B$_1$)$_z$(B$_2$)$_{1-z}$(X$_1$)$_y$(X$_2$)$_{3-y}$, wherein x ranges from 0 to 1, z ranges from 0 to 1, and y ranges from 0 to 3 are encompassed by Formula I.

The perovskite may be a hybrid organic-inorganic perovskite, by which it is meant that at least one of the ions of A, B, and X (typically A) comprises an organic group. In some embodiments, A provides the organic group. Various organic groups may be used, e.g., alkyl and aryl. In some embodiments, the perovskite has Formula I, wherein A comprises an organic group; B is Pb$^{2+}$ or Sn$^{2+}$ and X is a halide. A may be a protonated amine. A may be selected from primary ammoniums and iminiums.

Figure 18:
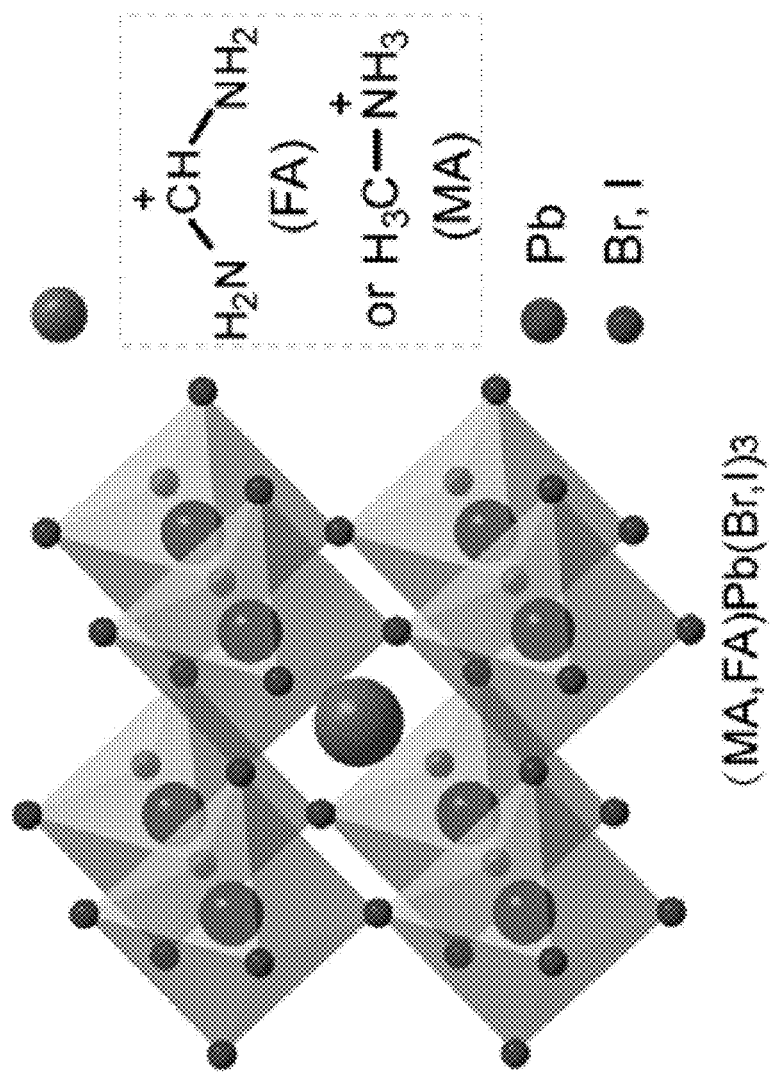
FIG. 18 shows a schematic of crystal structure of lead halide perovskites APbX$_3$, A=formamidinium (FA) or methylammonium (MA), X=Br or I.

Perovskites having Formula I may be referred to as three-dimensional (3D) perovskites. FIG. 18 shows the crystal structure of perovskites having Formula I.

The perovskite from which the single-crystal perovskite structures are composed may have Formula II, $$A_2BX_4 \quad \text{(Formula II)}.$$

In Formula II, A (the cation) may be selected from protonated long chain alkylamine C$_n$H$_{2n+1}$NH$_3^+$, wherein n is 3 or greater (but typically less than 20); C$_{n1}$H$_{2n1-1}$ C$_{n2}$H$_{2n2}$NH$_3^+$, wherein n$_1$ is 3 or greater (but typically less than 20) and wherein n$_2$ is 0 or greater (but typically less than 20); C$_6$H$_{11}$C$_n$H$_{2n}$NH$_3^+$, wherein n is 0 or greater (but typically less than 20); and C$_6$H$_5$C$_n$H$_{2n}$NH$_3^+$, wherein n is 0 or greater (but typically less than 20). In Formula II, B and X may be as described above with respect to Formula I. In some embodiments, A is $C_6H_{11}NH_3^+$ (cyclohexylamine) or $C_6H_5C_2H_4NH_3^+$ (phenethylammonium). In some embodiments, A is $C_6H_5C_2H_4NH_3^+$ (phenethylammonium); B is $Pb^{2-}$ or $Sn^{2+}$; and X is a halide. Perovskites having Formula II may be referred to as two-dimensional (2D) perovskites. Perovskites having Formula II are hybrid organic-inorganic perovskites. Formula II also encompasses alloy perovskites as describe above with respect to Formula I.

In general, hybrid organic-inorganic perovskites generally adopt the formula of $(RNH_3)_2(CH_3NH_3)_{n-1}BX_{3n+1}$, in which R is long-chain alkyl or aryl group, B is a metal ion (e.g., $Pb^{2+}$, $Sn^{2-}$) and X is a halide anion (e.g., Cl, Br, I). The $CH_3NH_3^+$ group can also be another small protonated amine group such as a $CH(NH_2)_2^-$ (formamidinium) group. When n is infinite, the hybrid organic-inorganic perovskites have a three-dimensional (3D) perovskite structure, such as methylammonium lead triiodide ($MAPbI_3$) or formamidinium lead iodide ($FAPbI_3$) and their alloys. In the extreme case when n=1, these hybrid organic-inorganic perovskites have a two-dimensional (2D) layered structure, described above in Formula II, in which each layer consists of an extended network of corner-sharing metal halide octahedra $[BX_6]^{4-}$ and two layers of organic cations on both sides to balance the charge.

In the Formula above, the following definitions may be used. An alkyl group may be a linear, branched or cyclic alkyl group in which the number of carbons may range from, e.g., 2 to 24, 2 to 20, 2 to 18, 2 to 12, 2 to 6, 1 to 3, etc. The alkyl group may be unsubstituted, by which it is meant the alkyl group contains no heteroatoms. The alkyl group may be substituted, by which it is meant an unsubstituted alkyl group in which one or more bonds to a carbon(s) or hydrogen(s) are replaced by a bond to non-hydrogen and non-carbon atoms. Non-hydrogen and non-carbon atoms include, e.g., a halogen atom such as F, Cl, Br, and I; an oxygen atom, including an oxygen atom in groups such as hydroxyl, alkoxy, aryloxy, carbonyl, carboxyl, and ester groups; a nitrogen atom, including a nitrogen atom in groups such as amines, amides, alkylamines, arylamines, and alkylarylamines, and nitriles; and a sulfur atom. Methyl and ethyl are suitable alkyl groups.

An aryl group may be monocyclic having one aromatic ring or polycyclic having fused aromatic rings (e.g., two, three, etc. rings). Monocyclic and polycyclic aryl groups may be unsubstituted or substituted. Substituted monocyclic and polycyclic aryl groups are groups in which one or more bonds to a carbon(s) or hydrogen(s) are replaced by a bond to non-hydrogen and non-carbon atoms. Illustrative non-hydrogen and non-carbon atoms have been described above.

The particular composition of the perovskite structure may be selected depending upon the particular application. By way of illustration, the perovskite may be a perovskite which is capable of light emission of a selected wavelength or range of wavelengths when under the influence of an applied electromagnetic field. The wavelength(s) may be in the visible or the near-infrared portion of the electromagnetic spectrum. The wavelength(s) may be in the range of from about 400 nm to about 800 nm.

The perovskite structures are single-crystal in nature. By "single-crystal" it is meant that the extended crystal lattice of the perovskite structure is substantially continuous and substantially unbroken with few or substantially no grain boundaries and is substantially single phase having a perovskite crystal structure. Thus, the single-crystal perovskite structures are distinguished from perovskite materials characterized by two or more crystalline phases and from polycrystalline perovskite materials, both of which may have multiple crystalline orientations and many crystalline domain boundaries. The single-crystal nature of the perovskite structures may be confirmed using x-ray diffraction (XRD), transmission electron microscopy (TEM), and electron diffraction (ED). When the structures are sufficiently large in some dimension(s), optical microscopy, especially when assisted with polarized light, can reveal the crystalline domains and also confirm their single-crystal nature. With respect to "single-crystal", the term "substantially" is used in recognition of the fact that the crystal lattice may not be perfectly continuous, perfectly unbroken and may not have zero grain boundaries. Similarly, the single-crystal perovskite structures may have a very small amount of impurities. Nevertheless, the term "substantially" is meant to connote perovskite structures which would be considered to be single-crystal, e.g., based upon a comparison of their XRD patterns, ED patterns, and/or TEM images to those of an ideal single-crystal perovskite.

The term "structure" in "perovskite structure" is meant to connote that the disclosed methods are capable of producing perovskite materials which are composed of distinct and distinguishable structural elements having a definable shape and size. One or more dimensions of the structures may be on the order of nanometers (i.e., between about 1 nm and about 1000 nm) and the term "nanostructure" or "nano" may be used in reference to such structures. Each of the dimensions of the structures may be on the order of micrometers (i.e., between about 1 µm and about 1000 µm) and the term "microstructure" or "micro" may be used in reference to such structures.

The perovskite structures may be characterized by their shape. The perovskite structures are generally elongated structures having opposing ends and relatively large aspect ratios (i.e., the ratio of the largest dimension, generally defined as the length l, to the smallest dimension). In some embodiments, the aspect ratio is at least 5. In some embodiments, the aspect ratio is at least 10, at least 100, or at least 1000. This includes embodiments, in which the aspect ratio is in the range of from 5 to 1,000, or from 10 to 1,000 or from 10 to 100.

Figure 32:
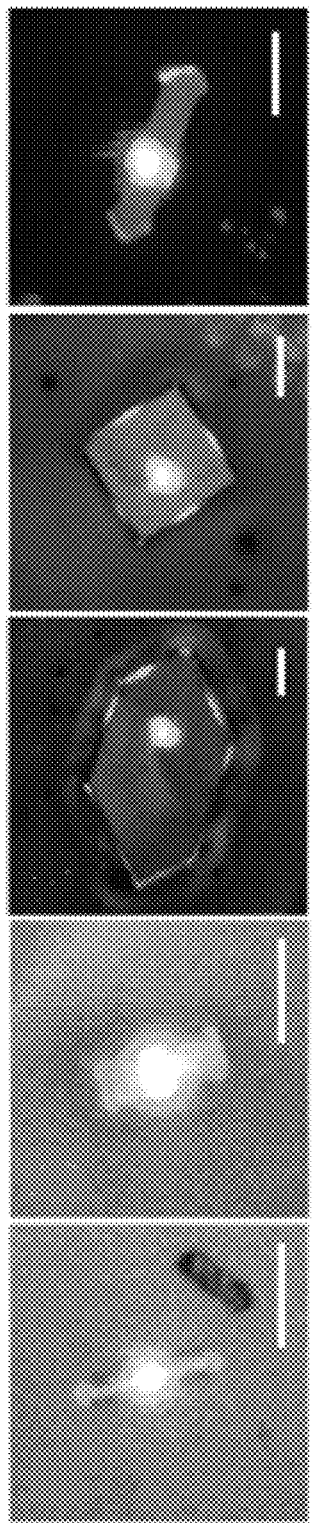
FIGS. 32A-E show optical images of a series of individual microstructures of (PEA)$_2$Pb(Br,I)$_4$ alloys showing strong waveguiding effect.

In some embodiments, the perovskite structures may be characterized by a length l, a width w, and a thickness t. In such embodiments, t is the smallest dimension and generally, l>w. Perovskite structures in which l and w are closer in magnitude (including of similar magnitude) and l, w>>t may be referred to as "plates," "platelets" and "belts." However, the use of l, w and t is not meant to imply that the shape of the perovskite structure in the plane defined by l and w is limited to rectangular shapes. For example, the shape may be a hexagonal plate (see, e.g., FIG. 32C and 32E). In that case, l may refer to the largest dimension across opposing sides in the plane defined by the plate and w may refer to the smallest dimension across opposing sides in the plane defined by the plate.

Perovskite structures in which w and t are closer in magnitude (including of similar magnitude) and l>>w, t may be referred to as "wires," "rods," and "tubes" (if the perovskite structure defines an interior bore). Perovskite structures in which w~t and/or perovskite structures which have a circular or hexagonal or similarly shaped cross-section (taken perpendicular to l) may be characterized a diameter d, rather than a width w and thickness t. In such structures, l>>d. Thus, rods, wires and tubes may be characterized by a diameter d. Plates, belts, wires, rods and tubes may be distinguished from structures having aspect ratios ~1 such as spheres, cubes, etc. Illustrative plates, belts and wires are shown in FIGS. 3E and 3F and FIGS. 30A and 30B.

The particular dimensions of the perovskite structures may vary. For perovskite structures characterized by a length l, a width w, and a thickness t (e.g., plates and belts), l may be in the range of from about 1 µm to about 100 µm. This includes embodiments in which l is in the range of from about 1 µm to about 50 µm, from about 1 µm to about 10 µm, from about 10 µm to about 100 µm. or from about 10 µm to about 50 µm. The width w may be in the range of from about 1 µm to about 100 µm. This includes embodiments in which w is in the range of from about 1 µm to about 50 µm, from about 1 µm to about 10 µm, from about 10 µm to about 100 µm, or from about 10 µm to about 50 µm. The thickness t may be in the range of from about 10 nm to about 10 µm. This includes embodiments in which t is in the range of from about 10 nm to about 5 µm, from about 10 nm to about 1 µm, from about 50 nm to about 10 µm, from about 50 nm to about 5 µm, from about 50 nm to about 1 µm, from about 100 nm to about 10 µm, from about 100 nm to about 5 µm, from about 100 nm to about 1 µm, from about 10 nm to about 100 nm, from about 10 nm to about 50 nm, or from about 20 nm to about 50 nm.

For perovskite structures characterized by a length l and a diameter d (e.g., rods, wires and tubes), l may be in the range of from about 1 µm to about 100 µm. This includes embodiments in which l is in the range of from about 1 µm to about 50 µm. from about 1 µm to about 10 µm. from about 10 µm to about 100 µm, or from about 10 µm to about 50 µm. The diameter d may be in the range of from about 10 nm to about 1 µm. This includes embodiments in which d is in the range of from about 50 nm to about 1 µm, or from about 100 nm to about 1 µm.

The dimensions of the perovskite structures further distinguish them from bulk materials (e.g., see FIGS. 7A-7B) as well as smaller nanostructures (structures having one, two, or three dimensions of less than about 10 nm).

The thickness t or the diameter d may be selected such that the perovskite structure is capable of supporting a waveguide mode(s) in order to produce lasing action when under the influence of an applied electromagnetic field. For such applications, t or d may still less than about 10 µm, but sufficiently large (e.g., greater than about 50 nm, greater than about 75 nm or greater than about 100 nm) so as to support the waveguide mode(s). Such perovskite structures are distinguished from structures in which the thickness t or the diameter d is too small to support a waveguide mode(s).

The dimensions described above may refer to an average value over a collection of perovskite structures.

Figure 13:
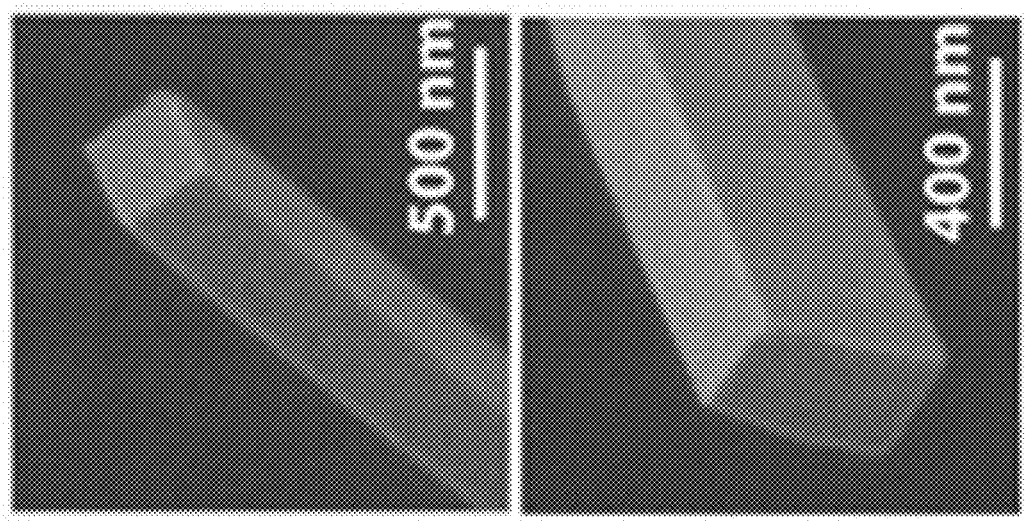
FIG. 13 shows magnified SEM images of two CH$_3$NH$_3$PbI$_3$ NWs, showing an end facet of each NW.

The perovskite structures may be characterized by the shape of a cross-section taken perpendicular to an axis defined along the largest dimension of the structure (e.g., l). In some embodiments, the cross-section is rectangular, square, or hexagonal. As discussed in Example 2, below, rectangular or square cross-sections make such perovskite structures particularly amenable to post-processing, e.g., deposition of a metal film on a surface of the perovskite structure. Similarly, the perovskite structures may be characterized by the shape of the facets defined at the opposing ends of the perovskite structure along its length (i.e., the end facets). The shape of the end facets may be rectangular, square or hexagonal. The end facets may be substantially parallel to one another and substantially perpendicular to an axis defined along the length of the perovskite structure. The end facets may be substantially smooth and flat. Illustrative end facets are shown in FIG. 13. The end facets shown in FIG. 13, which are substantially parallel to one another, substantially perpendicular to the longitudinal axes of the perovskite structures, and substantially smooth and flat, are configured such that they form a Fabry-Perot optical cavity. The disclosed methods are capable of providing such end facets as part of the growth process; no subsequent cleaving step is required.

Regardless of the particular shape of the perovskite structures, the shape is well-defined (i.e., the shape may be characterized by a regular, recognizable geometry) and uniform (i.e., the shape is substantially maintained along the length of the perovskite structure). Similarly, the other dimensions of the perovskite structure (e.g., w, t, or d) are substantially uniform along the length of the perovskite structure. In addition to the end facets of the perovskite structure, the other facets of the perovskite structure are substantially smooth and flat and neighboring facets meet at substantially sharp edges. Thus, the perovskite structures are distinguished from perovskite materials formed using other conventional synthetic methods which provide irregularly shaped structures, non-uniform structures, and/or structures having rough surfaces and edges.

Because of their unique structural features described above, perovskite structures formed using the disclosed methods are capable of exhibiting properties which are superior to, and/or different from, perovskite materials formed using other conventional synthetic methods. Moreover, the disclosed methods are capable of providing a particular combination of structural features, depending upon the desired application. By way of illustration, at least some embodiments of the perovskite structures are configured such that they produce lasing action from the perovskite structure when under the influence of an applied electromagnetic field. In such an embodiment, the perovskite from which the structure is formed is the active medium and is selected to achieve light emission when under the influence of an applied electromagnetic field. The thickness t or the diameter d is selected such that the perovskite structure supports a waveguide mode(s). The facets at opposing ends of the perovskite structure are configured to provide optical feedback for a selected wavelength of light from the light emission and to produce lasing action from the perovskite structure when under the influence of an applied electromagnetic field. The electromagnetic field may be derived from an optical source (e.g., a laser) or an electrical source. In the latter case, the perovskite structure may comprise a layer of a conductive material (e.g., a metal such as Al or Au) coating a surface of the perovskite structure to facilitate electrical injection. In some embodiments, the perovskite structure is a perovskite wire, rod or belt and may be characterized by a rectangular or hexagonal cross-section and rectangular or hexagonal end facets. The aspect ratio may be at least 10, at least 25, at least 50, at least 100. The aspect ratio may be in the range of from 10 to 100. The diameter d may be in the range of from about 100 nm to about 1 µm. The lasing action may be from the two end facets of the perovskite wire, rod or belt.

As illustrated in Examples 2 and 3, below, the disclosed methods are capable of producing perovskite structures exhibiting lasing action at room temperature with very low lasing thresholds ($P_{TH}$) and very high quality factors (Q). The particular $P_{TH}$ and Q depends, at least in part, upon the perovskite from which the structure is formed. In some embodiments, the perovskite is a hybrid organic-inorganic lead halide perovskite (e.g., $ABX_3$, wherein A is a cation (e.g., a protonated amine) comprising an organic group or a combination of such cations; B is lead; and X is a halide or a combination of halides) and is characterized by a $P_{TH}$ of no more than about 7 µJcm$^{-2}$. This includes embodiments in which the P$_{TH}$ is no more than about 5 µJcm$^{-2}$, or no more than about 1000 nJcm$^{-2}$. In some embodiments, the perovskite is a hybrid organic-inorganic lead halide perovskite characterized by a Q factor of at least 1000. This includes embodiments in which the Q factor is at least 1500, at least 2000, at least 2500, at least 3000, at least 3500, at least 4000, at least 8000, or at least 10000. P$_{TH}$ and Q may be determined using the optical characterization techniques described in Examples 2 and 3, below.

As described above, at least some embodiments of the perovskite structures may be used in lasing applications. In one embodiment, a method of using a perovskite structure comprises applying an electromagnetic field to the perovskite structure sufficient to stimulate light emission from the perovskite, whereby optical feedback between the end facets of the perovskite structure for a selected wavelength of light from the light emission produces lasing action.

In some embodiments, the perovskite structures are nanoplates or wires configured to provide a whispering galley model (WGM) optical cavity.

The perovskite structures may be delivered in a variety of forms. By way of illustration, one form is a composition comprising a solvent and a plurality of perovskite structures dispersed in the solvent. Another form is a substrate comprising a plurality of perovskite structures dispersed on the surface of the substrate. In some embodiments, the perovskite structures may be arranged in an array on the surface of the substrate. The perovskite structures within the array may be the same or different (e.g., they may be composed of the same type or different types of perovskites). If the substrate is a growth substrate upon which the perovskite structures were grown, the perovskite structures may be dispersed randomly on the surface, be attached to the surface at an end or a side, and may extend generally upwardly from the surface (see, e.g., FIGS. 1C-1F and FIGS. 3E-3F and FIGS. 27A-27B).

The disclosed methods are based on low temperature dissolution of a film of a metal precursor compound in a solution of a cation precursor compound and recrystallization of metal anion complexes to form to single-crystal perovskite structures.

As described above, the disclosed methods are based on low temperature dissolution of a film of a metal precursor compound (which releases the metal from the film to form a metal anion complex) in a solution of a cation precursor compound and subsequent recrystallization of the metal anion complexes with cations from the cation precursor compound to form the single-crystal perovskite structures. In one embodiment, a method comprises immersing a film of a metal precursor compound in a solution comprising a cation precursor compound at a concentration of the cation precursor compound, a growth time, and a growth temperature sufficient to dissolve the film and induce recrystallization to form a plurality of single-crystal perovskite structures.

The metal precursor compound provides a source of the metal (B) of the perovskite (e.g., the metal precursor compound comprises a divalent metal ion such as any of the divalent metal ions described above). The cation precursor compound provides a source of the cation (A) of the perovskite (e.g., the cation precursor compound comprises a protonated amine such as any of the protonated amines described above). One or both of these precursor compounds provides a source of the anion (X) of the perovskite (i.e., one or both of the metal precursor compound and the cation precursor compound further comprises any of the anions described above). Thus, the particular choice of the precursor compounds depends, at least in part, upon the desired perovskite. However, the metal precursor compound may be selected to be sparingly soluble at room temperature in the selected solution of the cation precursor compound.

Suitable metal precursor compounds include metal halides (e.g., PbI$_2$, PbBr$_2$, PbCl$_2$); metal formate (e.g., Pb(HCOO)$_2$); metal carboxylates (e.g., Pb(RCOO)$_2$, wherein R is an alkyl group, e.g., methyl or ethyl); metal carbonates (e.g., PbCO$_3$); metal chalcogenides (e.g., PbO, PbS, PbTe); metal nitrates (e.g., Pb(NO$_3$)$_2$) or perchlorates (e.g., Pb(ClO$_4$)$_2$) or sulfates (e.g., PbSO$_4$). These illustrative compounds are based on lead, but other metals may be used, including the divalent metal ions described above. Similar compounds may be used for cation precursor compounds e.g., halides such as CH$_3$CH$_3$I, CH$_3$CH$_3$Br, CH$_3$CH$_3$Cl, CH(NH$_2$)$_2$I, CH(NH$_2$)$_2$Br, etc.

Illustrative methods for making metal precursor compounds and cation precursor compounds are provided in the Examples below.

The inventors have found that providing the metal precursor compound as a film on a substrate is important for achieving perovskite structures having the crystallinity and other structural features described above. The film may be disposed on a variety of substrates, e.g., a fluorine-doped tin oxide coated glass substrate or an uncoated glass substrate. The film may be formed using a variety of techniques, e.g., spin coating, drop casting, etc. Films having different thicknesses may be used, e.g., a thickness in the range of from 100 nm to 800 µm. Substantially smooth and flat films facilitate the formation of high quality perovskite structures, but they are not required.

In some embodiments, the film may substantially completely cover the surface of the substrate such that there are few or no regions of exposed substrate. In other embodiments, the film may partially cover the surface of the substrate such that there exists a plurality of regions of exposed substrate.

The inventors have also found that the concentration of the cation precursor compound in the solution is important for achieving perovskite structures having the crystallinity and other structural features described above. In general, the concentration should be sufficiently high to complex to and dissolve the film of the metal precursor compound, thereby releasing the metal from the film to form metal anion complex intermediates in the solution, but sufficiently low such that the perovskite is able to crystallize out of the solution. In other words, the local concentration of the released metal anion complexes should be minimized to maintain a low supersaturation condition for crystal growth. As shown in Example 1, below, the inventors have found that there exists a cation precursor concentration range which achieves this condition and allows for the optimal growth of the single-crystal perovskite structures. The particular concentration range will depend upon the composition of the perovskite structure (see, e.g., Formula I or II). By way of illustration, a suitable cation precursor (CH$_3$NH$_3$I) concentration range for forming single-crystal methylammonium lead iodide perovskite structures is in the range of from about 20 mg/mL to about 60 mg/mL. This concentration range is significantly higher than those used in other conventional synthetic methods for forming methylammonium lead iodide perovskite materials. Various solvents may be used to form the solution of the cation precursor compound, provided the solvent does not dissolve the cation precursor compound and the perovskite, but dissolves the metal anion complex intermediates, e.g., an organic solvent such as isopropyl alcohol.

The growth time and growth temperature may be selected to achieve single-crystal perovskite structures having certain shapes, cross-sections and dimensions. Suitable growth times and growth temperatures are illustrated in the Examples, below. However, the growth time may be on the order of several hours. The growth temperature may be room temperature, or for certain types of perovskite, slightly elevated, e.g., about 50° C.

The inventors have also found that the orientation of the film of the metal precursor compound during the immersion step can be important for achieving optimal single-crystal perovskite structures having uniform morphology and high yield. The orientation is referenced with respect to the interface formed between the solution of the cation precursor compound and the surrounding atmosphere. In some embodiments, the film of the metal precursor compound is oriented face up in the solution of the cation precursor compound, i.e., the surface of the film faces towards the interface. In other embodiments, the film of the metal precursor compound is oriented face down in the solution of the cation precursor compound, i.e., the surface of the film faces away from the interface.

As described above, the perovskite of the perovskite structures may be an alloy comprising more than one type of cation (A), more than one type of metal ion (B) and/or more than one type of anion (X). Such alloys may be formed by including more than one type of cation precursor compound in the solution of cation precursor compound, and in the case of B ion alloys, more than one type of metal precursor compound. The ratio of the concentration of each type may be selected depending upon the desired composition.

In some embodiments, the immersion step is accomplished in the presence of a second substrate. The second substrate (e.g., silicon, $CaF_2$, etc.) may be uncoated. The film of the metal precursor compound may be positioned such that it is oppositely facing the surface of the second substrate. The film of the metal precursor compound may be resting on, or otherwise in contact with, the surface of the second substrate. During the growth time at the growth temperature and appropriate concentration of the cation precursor compound, the film of the metal precursor compound dissolves, thereby releasing the metal from the film to form metal anion complexes, which recrystallize with cations from the cation precursor compound to form the perovskite structures on the surface of the second substrate. In this embodiment, the substrate having the film of the metal precursor compound may be referred to as the "precursor" substrate. This embodiment of the method of forming perovskite structures may be referred to as "solution transport crystal growth." This embodiment of the method may be used to form perovskite structures in which the perovskite has Formula II. (See Example 4.)

The method may comprise additional steps. In one embodiment, the method comprises a pre-growth step in which the film of the metal precursor compound is first immersed in a first solution of a first cation precursor compound at a concentration of the first cation precursor compound, a seeding time, and a seeding temperature sufficient to form a seed layer on the film of the metal precursor compound. The subsequent immersion step comprises immersing the seeded film of the metal precursor compound in a second solution comprising a second cation precursor compound at a concentration of the second cation precursor compound, a growth time, and a growth temperature sufficient to grow the plurality of single-crystal perovskite structures. This embodiment also provides alloy perovskite structures. The concentration of the first cation precursor compound may be relatively high and the seeding time may be relatively short as compared to the concentration of the second cation precursor compound and the growth time, respectively.

In another embodiment, the method comprises a post-growth annealing step in which the substrate is heated at an annealing temperature (e.g., 100° C., 150° C., 200° C.) for an annealing time (e.g., a few minutes). Such an annealing step may be used to provide the proper phase for the single-crystal perovskite structures.

Figure 33:
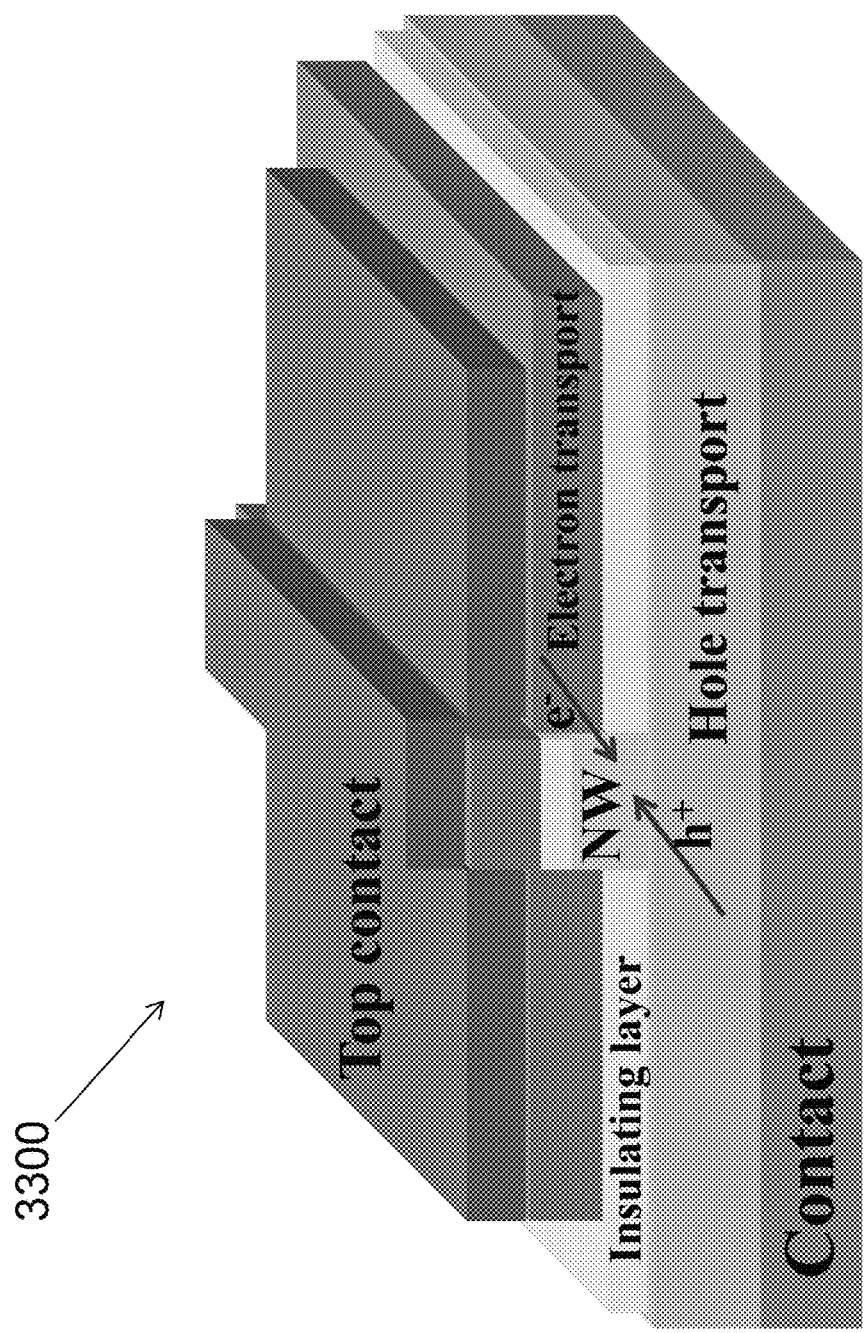
FIG. 33 shows an illustrative embodiment of a light emitting diode or an electrically driven laser comprising a single perovskite nanowire (NW).
Figure 34:
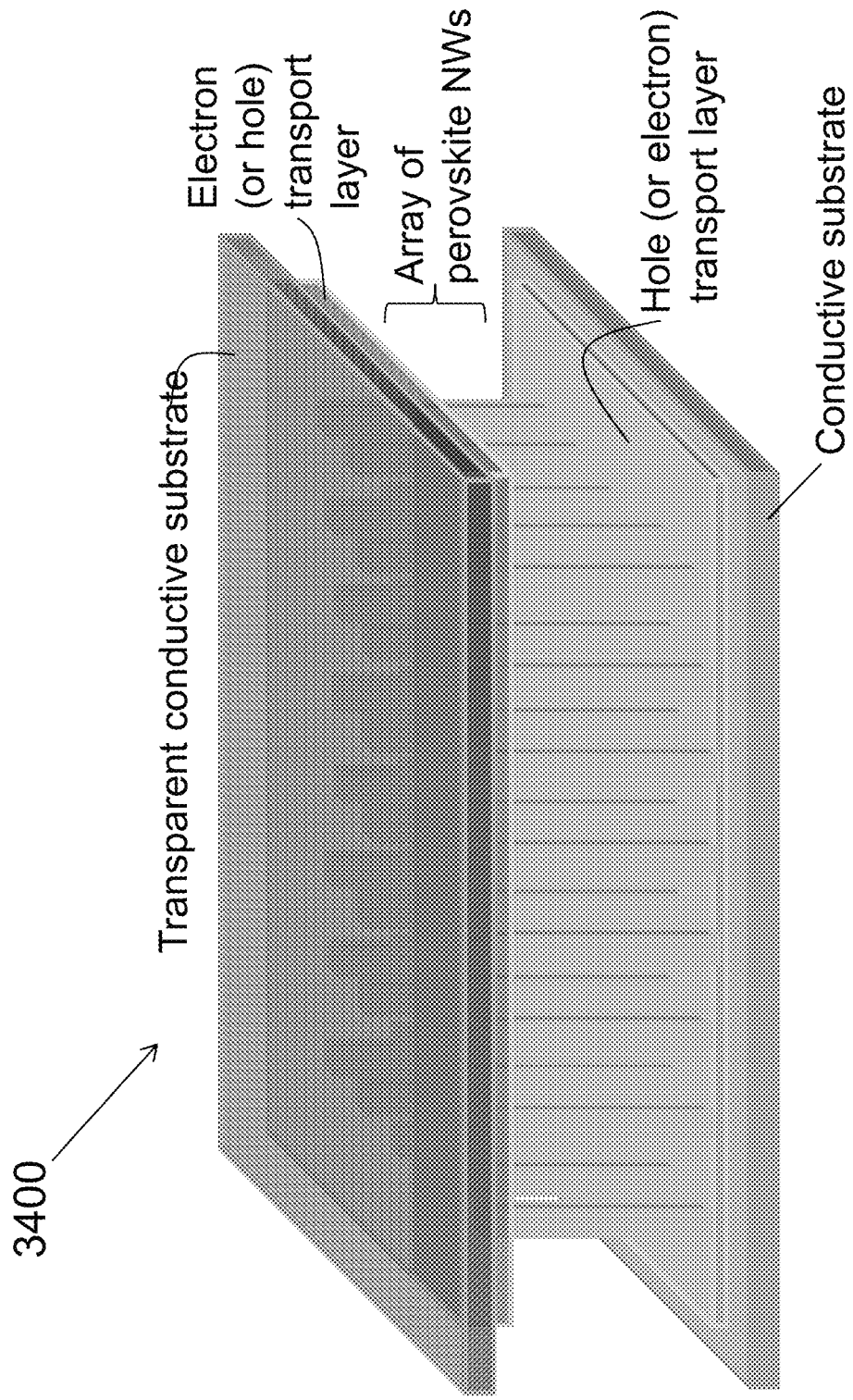
FIG. 34 shows an illustrative embodiment of a light emitting diode or an electrically driven laser comprising an array of substantially vertically aligned perovskite nanowires.
Figure 35:
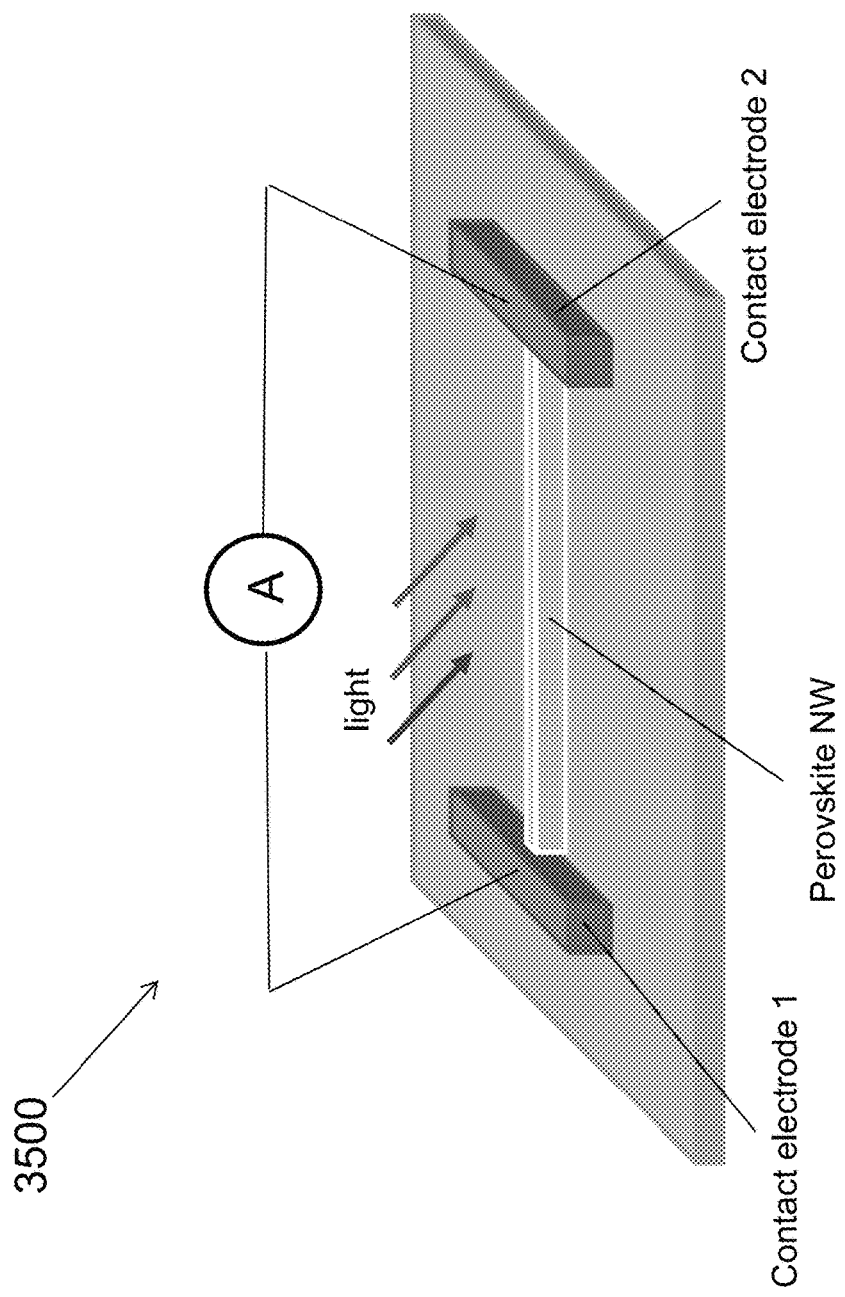
FIG. 35 shows an illustrative embodiment of a photodetector comprising a single perovskite nanowire.
Figure 36:
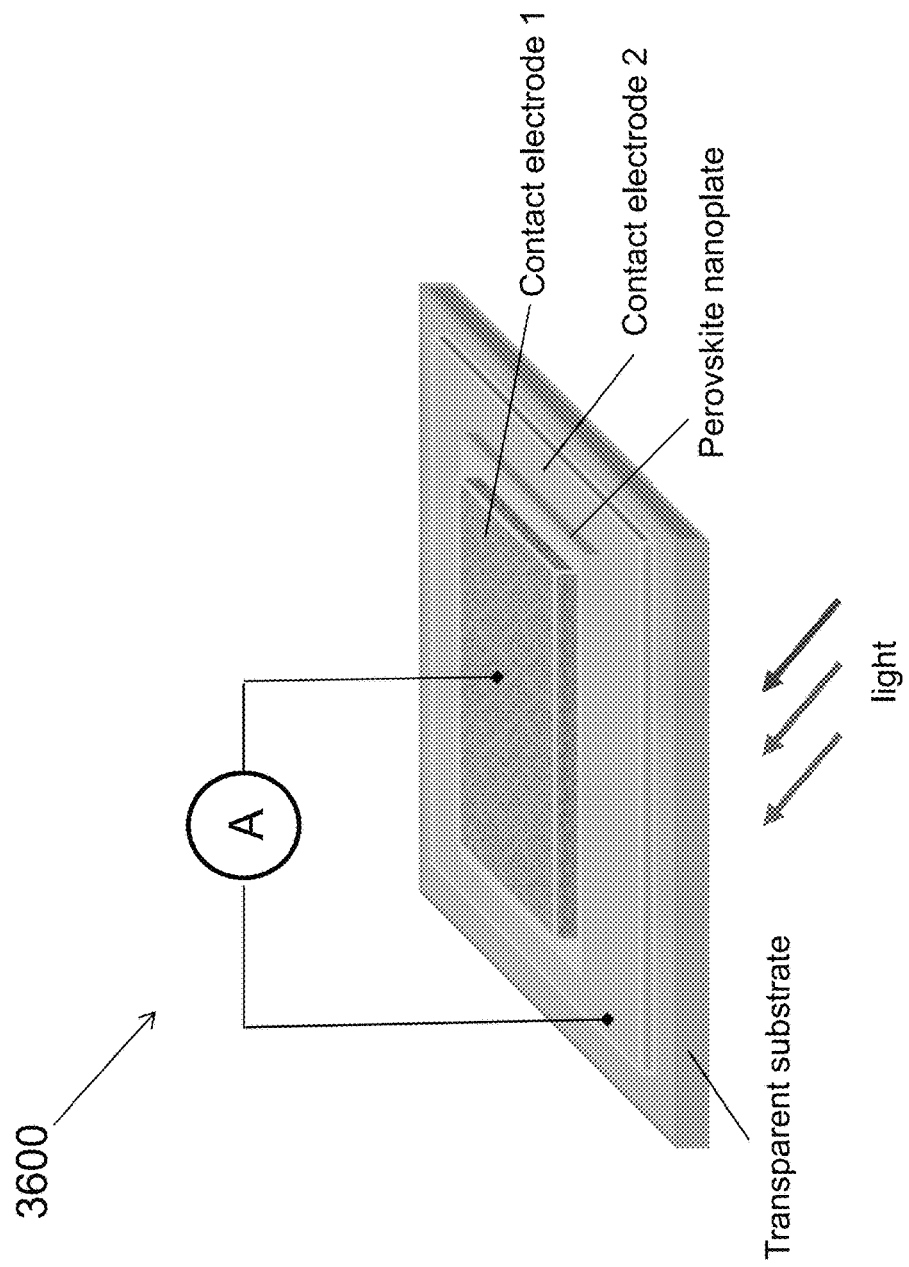
FIG. 36 shows an illustrative embodiment of a photodetector comprising a single perovskite nanoplate.

The perovskite structures formed using the disclosed methods may be used as building blocks to form a variety of devices. Due to their dimensions, the perovskite structures enable the miniaturization of such devices. In the devices, the perovskite structures may be used individually or in a plurality, e.g., in an array of perovskite structures. Illustrative devices include perovskite structures configured to produce light emission and/or lasing action (e.g., light emitting diodes and lasers). Other devices can include photodetectors. Still other devices can be based on circuits (e.g., logic gate structures) and sensors (e.g., chemical and/or biological sensors. Illustrative devices are shown in FIGS. 33-36. FIG. 33 is an illustrative embodiment of a light emitting diode or an electrically driven laser 3300 comprising a single perovskite nanowire (NW). FIG. 34 is an illustrative embodiment of a light emitting diode or an electrically driven laser 3400 comprising an array of substantially vertically aligned perovskite nanowires. FIG. 35 is an illustrative embodiment of a photodetector 3500 comprising a single perovskite nanowire. FIG. 35 is an illustrative embodiment of a photodetector 3600 comprising a single perovskite nanoplate.

The present disclosure encompasses the methods described above as well as the single-crystal perovskite structures, the devices incorporating the structures, and methods of using the devices.

EXAMPLES

Example 1

Single Crystal Methylammonium Lead Halide Perovskite Nanostructures

This example is derived from Fu Y., et. al., Solution Growth of Single Crystal Methylammonium Lead Halide Perovskite Nanostructures for Optoelectronic and Photovoltaic Applications, *J. Am. Chem. Soc.* 2015, 137, 5810-5818, which is hereby incorporated by reference in its entirety.

Materials and Methods

All chemicals and regents were purchased from Sigma-Aldrich and used as received unless noted otherwise.

Synthesis of $CH_3NH_3I$ and $CH_3NH_3Br$. The $CH_3NH_3I$ (MAI) was synthesized by slowly mixing 1:1 methylamine (40% in methanol) and HI (57 wt % in water) in a flask. The $CH_3NH_3I$ salt precipitated as the solvent was carefully evaporated. The product was washed with diethyl ether for several times and then dried at 80° C. in a vacuum oven for ~24 h. The $CH_3NH_3Br$ (MABr) was synthesized using similar method using HBr.

Growth of $MAPbI_3$ and $MAPbBr_3$ nanostructures. The single crystal $MAPbI_3$ nanostructures were synthesized by placing lead iodide ($PbI_2$) or lead acetate ($PbAc_2$) film on fluorine-doped tin oxide coated glass substrates (FTO, 10

Ω/sq) or glass slides (for optical characterization) into a MAI solution in isopropanol (1 mL), with the lead precursor coated side facing up at room temperature (22° C.). For the synthesis of MAPbBr$_3$ nanostructures, the substrate was placed in MABr solution in isopropanol (1 mL), with the PbI$_2$ coated side facing down. The PbI$_2$ film was prepared by spin coating a solution of 400 mg/mL PbI$_2$ (99.99%) in dimethylformamide (DMF) at 3000 r.p.m for 15 s. The PbAc$_2$ film was prepared by spin coating a solution of 100 mg/mL PbAc$_2$.3H$_2$O in nanopure water at 2000 r.p.m for 30 s. Before spin coating, the FTO substrate was ultrasonically cleaned in IPA, acetone and ethanol for 5 min sequentially, and then was cleaned with oxygen plasma (150 W RF, 1 sccm O$_2$, <200 mTorr, 3 min) to remove organic residues. Both PbI$_2$ and PbAc$_2$ film were dried at 100° C. for 30 s to remove the remnant solvent before placed into the MAI solution. After a specified reaction time, the FTO substrate was removed and dipped into isopropanol solvent to remove any leftover salt on the film, dried under a stream of nitrogen flow, and then dried on a hot plate at 100° C. for another 15 s.

Synthesis of bulk MAPbI$_3$ single crystals. Following the previously reported method (Poglitsch, A.; Weber, D. *Journal of Chemical Physics* 1987, 87, 6373), the MAPbI$_3$ single crystals were grown by slow precipitation from a hydroiodic acid solution containing lead precursor. Specifically, 2.9 g of PbAc$_2$.3H$_2$O was dissolved in 10 ml of a concentrated aqueous HI solution (57 wt %) in a 100 mL flask and heated to 100° C. in an oil bath. After 3.1 g of CH$_3$NH$_3$I was added to this solution, a lot of precipitate was formed by slowly cooling the solution from 100° C. to 40° C. in 60 h. These products were collected and rinsed with IPA for several times before dried on a hot plate.

Structural characterizations of perovskite nanostructures. The scanning electron microscopy (SEM) was performed using a LEO SUPRA 55 VP field-emission SEM operated at 1.5 kV. The sample for transmission electron microscope (TEM) was prepared by dry transferring the as-grown MAPbI$_3$ nanostructures onto a TEM grid (Ted Pella, lacey carbon type-A support film, 300-mesh, copper, #01890-F). The TEM were carried out on a FEI Titan scanning transmission electron microscope (STEM) at an accelerating voltage of 200 kV or Technai T12 TEM at an accelerating voltage of 120 kV. The PXRD data were collected on as as-grown samples on substrates using a Bruker D8 Advance Powder X-ray Diffractometer with Cu Kα radiation. The background was fitted and then subtracted using Jade program.

Surface photoresponse measurement. The sample used in time-resolved SPR was synthesized using PbI$_2$ precursor and 40 mg/mL MAI/IPA solution at a reaction time of 20 h. The measurements were performed under ambient conditions (in air) in a capacitor-like arrangement. The perovskite sample and an FTO/glass electrode were assembled in a custom-made cell holder separated by a 127 μm thick Teflon spacer. The sample was illuminated through the FTO sense electrode by ~3 ns pulses at 0.1 mJ/pulse from a tunable laser (NT340, Ekspla, Inc., Vilnius, Lithuania). The signal collected was using exciting wavelength at 700 nm. The response from the sense electrode was amplified by a fast amplifier (Model TA2000B-1, FAST ComTec GmbH, Oberhaching/Munchen, Germany) with a 50 Ω input and output impedances, 1.5 GHz bandwidth, and 10× voltage gain, and was recorded by a digital oscilloscope (DSO9404A, Agilent, Inc., Santa Clara, Calif.).

Figure 3A:
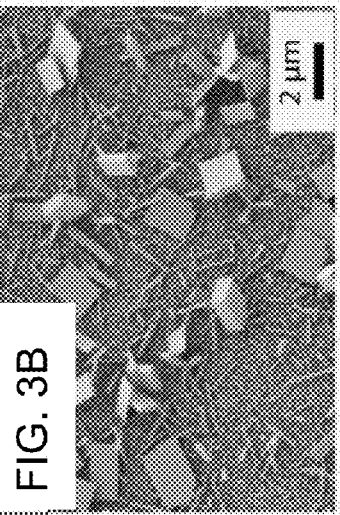
FIGS. 3A-3F show the structural characterizations of MAPbI$_3$ nanostructures synthesized using PbI$_2$ precursor at different reaction times. The concentration of MAI/IPA solution was fixed at 40 mg/mL.
Figure 3B:
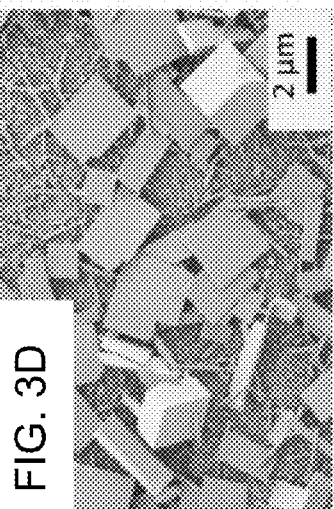
Figure 3C:
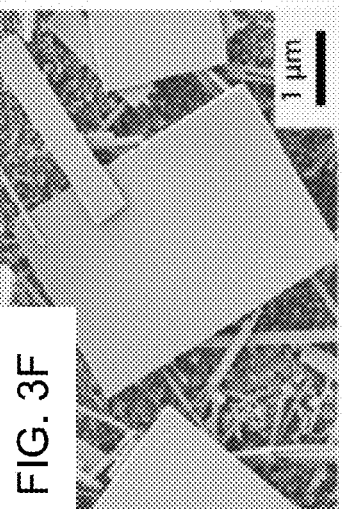
Figure 3D:
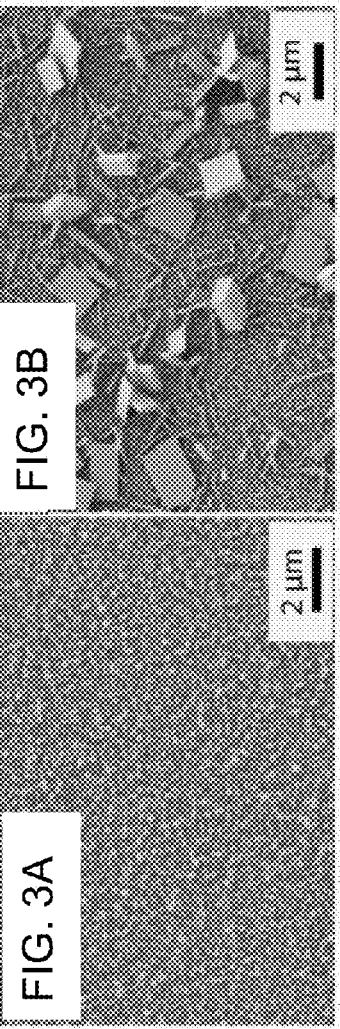
Figure 3E:
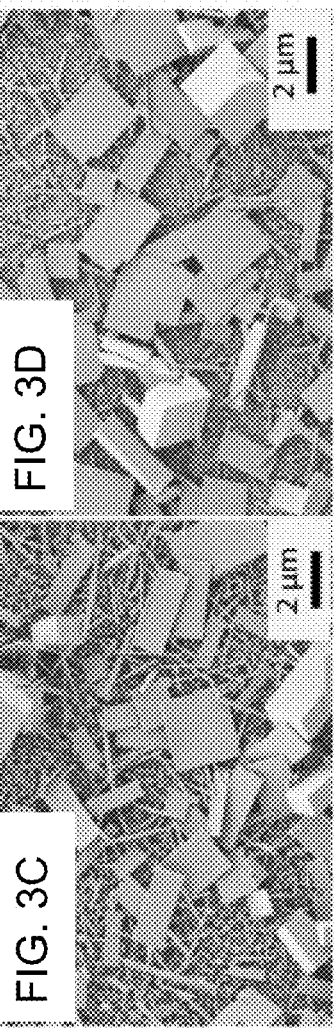

Optical characterization of MAPbI$_3$ nanostructures and bulk crystals. The photoluminescence (PL) of single crystal nanoplates and bulk crystals was collected with an Aramis Confocal Raman Microscope using a 532 nm laser source with a neutral density filter D4 and D3, respectively. The spatial resolution was about 1μm. The samples for PL measurement and dark-field image were transferred from FTO substrates to silicon substrates covered with SiO$_2$ (330 nm) by a dry transfer method. The dark field image of nanoplate (FIG. 3*d* inset) was taken using an optical microscope (Olympus, BX51M). The UV-Vis absorption of as-grown thin film was collected using a JASCO V-550 spectrometer.

For ultrafast pump-probe spectroscopy, the MAPbI$_3$ nanostructures were sealed with two pieces of glass slides using parafilm as spacer on a hot plate (100° C.) to minimize the exposure to moisture in the air. The pump beam was at 600 nm with a FWHM diameter at sample position was measured to be 1.44 mm, and pump power was set at 9.8 μJ/cm$^2$. The probe was set at 795 nm with a FWHM diameter of 589 μm. Both pulses had 50 fs FWHM, and the pump beam was chopped to half the repetition rate of the probe to allow active background subtraction. Transient absorption mode was used for the nanostructures and transient reflection mode was used for bulk single crystals. Both were measured from—200 ps to 3.7 ns in 50 ps steps.

Fabrication and characterization of solar cells. The FTO substrate was first patterned by etching with a 2 M HCl solution and Zn powders around a mask formed by strips of adhesive tape (3M, Scotch® Magic™ Tape). Before spin-coating PbI$_2$, a layer of compact TiO$_2$ film was deposited by spin-coating a solution consisted of 0.23 M titanium isopropoxide and 0.013 M HCl solution in isopropanol at 2000 rpm for 60 s on such patterned FTO substrate. This Ti precursor solution was prepared according to previous literature. (Docampo, P.; Ball, J. M.; Darwich, M.; Eperon, G. E.; Snaith, H. J. *Nature communications* 2013, 4, 2761.) The FTO substrate was then annealed in a muffle furnace at 500° C. for 30 min. The procedures of PbI$_2$ deposition and its conversion to nanostructured MAPbI$_3$ film followed the procedures presented above. After MAPbI$_3$ conversion, a hole conductor layer was deposited on nanostructured MAPbI$_3$ films by spin-coating a solution containing 70 mg spiro-MeOTAD, 30 μL 4-tert-butylpyridine, and 18 μL of 520 mg/mL acetonitrile solution of lithium bis(trifluoromethylsulphonyl) imide in 1 mL chlorobenzene at 3000 rpm for 30 s. The Au counter electrode was deposited on spiro-MeOTAD film by e-beam evaporating 100 nm of Au (Kurt J. Lesker Co., 99.99%) at 1 Å/s. A 1 kW Xe short arc lamp solar simulator (Newport Corp., Model 91191) with a AM1.5G filter was used to illuminate the devices at an intensity of 100 mW/cm$^2$. All J-V curve measurements were recorded in a two-electrode configuration using a Bio-Logic SP-200 potentiostat at a scan rate of 100 mV/s. The area of device was defined by the overlap of Au contact and FTO electrode, which was around 0.08 cm$^2$. The accurate value was measured by reading pixels of micrographs taken with an optical microscope.

Introduction

In this Example, the crystal growth of lead halide perovskite nanostructures using a facile solution conversion from lead iodide (and lead acetate) films to MAPbI$_3$ and MAPbBr$_3$ is demonstrated. Following a unique growth pathway, single crystal nanowires (NWs), nanorods (NRs), nanobelts (NBs), and nanoplates of MAPbI$_3$ were successfully grown. The room-temperature PL intensity of these 1D and 2D perovskite nanostructures is 200 times stronger than bulk single crystals directly grown from aqueous solutions and the carrier lifetime is ~10 times longer. In addition, following a different growth pathway, a highly crystalline nanostructured MAPbI$_3$ film with micrometer grain size and high surface coverage is achieved. Preliminary fabrication of photovoltaic devices based on such films achieved a power conversion efficiency of 10.6%.

Results and Discussion

Growth and characterizations of single crystal MAPbI$_3$ nanostructures. To synthesize single crystal perovskite NWs, NRs and nanoplates, a compact and uniform lead iodide (PbI$_2$) film was first introduced on fluorine-doped tin oxide (FTO) glass substrates by spin coating PbI$_2$ solution in dimethylformamide (DMF), and then dipped into methyl ammonium iodide (CH$_3$NH$_3$I, MAI) solution in isopropanol (IPA) (see detail in the Experimental Section). FIG. 1A shows the morphology of PbI$_2$ film before conversion. It exhibits uniform grains of several tens of nanometers. The PbI$_2$ deposited by spin-coating from DMF solution is the hexagonal 2H polytype, as confirmed by powder X-ray diffraction (PXRD), where the four diffraction peaks correspond to the (001), (002), (003) and (004) lattice planes of PbI$_2$ (see FIG. 2).

The effect of MAI concentration on crystal growth at room temperature was first investigated, while the growth time was fixed at 10 min. Representative morphologies of as-converted films using different concentrations of MAI are shown in FIGS. 1B-1H. The corresponding powder X-ray diffraction (PXRD) patterns are provided in FIG. 2. The film converted at MAI concentration of 10 mg/mL exhibits many crystalline cubic-like grains with size of several tens of nanometer on top of the surface. However, the PXRD (FIG. 2, 10 mg/mL curve) shows both the diffraction peaks from the MAPbI$_3$ phase and a relatively strong diffraction peak at 12.60° that corresponds to the (001) lattice plane of unconverted PbI$_2$, indicating the conversion is incomplete. The reason for incomplete conversion may be that the crystalline MAPbI$_3$ initially formed on the surface obstructs the continual diffusion of MA$^+$ ions to react with PbI$_2$, which will be discussed later. However, it is interesting that increasing the concentration of MAI (i.e. 20-60 mg/mL) leads to the growth of perovskite NRs and nanoplates with well-defined facets (FIGS. 1C-1G). However, when the concentration of MAI was further increased above 70 mg/mL, the NRs and nanoplates were reduced in both size and density again (FIG. 1H). Dissolution of PbI$_2$ was also observed. It was noted the FTO substrates are almost covered by MAPbI$_3$ nanoparticles in FIGS. 1C-1H. The PXRD (FIG. 2) confirms the as-converted MAPbI$_3$ is the tetragonal phase (Space group I4/mcm, a=8.8743 Å, c=12.6708 Å) at all MAI concentrations, while some amounts of PbI$_2$ still exist at low MAI concentrations (i.e. 10 mg/mL and 20 mg/mL). However, the (001) diffraction peak from PbI$_2$ gradually disappears as MAI concentration increases, indicating the conversion is faster and more complete.

Figure 3F:
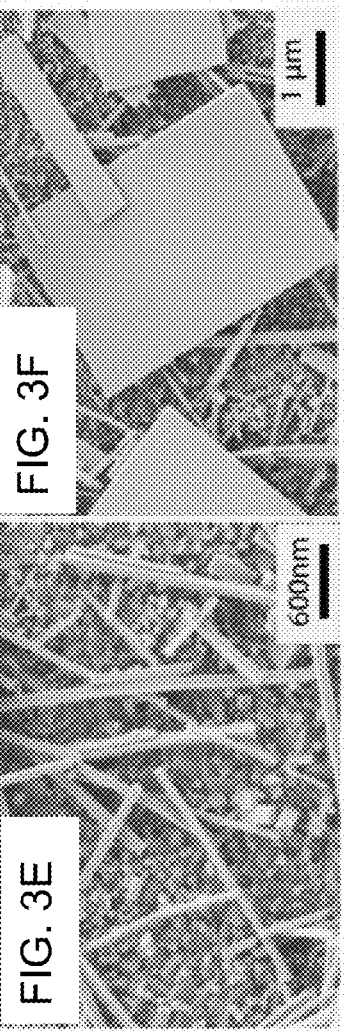
Figure 4:
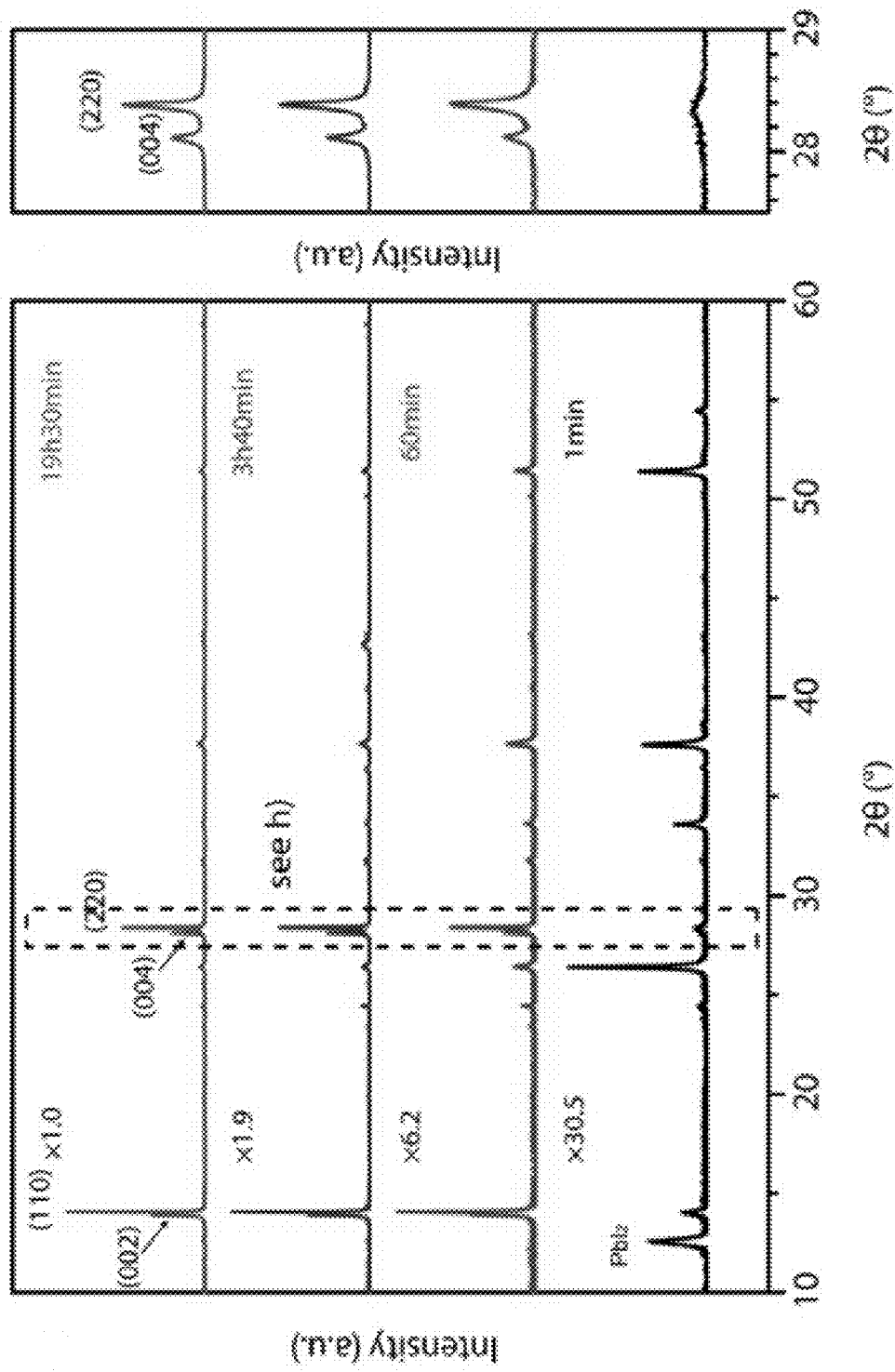
FIG. 4 shows the PXRD patterns corresponding to FIGS. 3A-3D. In order to compare relative diffraction intensity, all peak intensities are normalized to the strongest (110) diffraction peak of the MAPbI$_3$ film grown at 19 h 30 min. The details in the dashed rectangular box are shown in the box to the right.

The effect of reaction time on crystal growth was then investigated. The experiments were carried out at room temperature under the same concentration of MAI at 40 mg/mL. FIGS. 3A-3D display the SEM images of as-grown MAPbI$_3$ perovskite at a reaction time of 1 min, 60 min, 3 h 40 min, and 19 h 30 min, respectively. At a growth time of 1 min, the morphology of as-converted MAPbI$_3$ is similar to FIG. 1B, exhibiting many crystalline cubic-like grains with flat facets. At 10 min, it can clearly be seen that NWs and nanoplates have grown from the surface (FIG. 1E). The size of these MAPbI$_3$ nanostructures continues to increase as the reaction time increases further. In addition, it was noticed that in the background the MAPbI$_3$ perovskite nanoparticles on FTO progressively dissolved. The products at 19 h 30 min are NWs, NRs and nanoplates with well-defined flat facets on almost bare FTO substrates, as highlighted in FIGS. 3E and 3F. The NRs ranges from 1 to 3 μm in length, and are several tens of nanometers in diameter. The size and shape of the nanoplates vary, while the thickness is usually around a few hundred nanometers. FIG. 3F shows a nanoplate with ~2.3 μm×3 μm dimensions and a nanobelt with ~0.5 μm×2.5 μm dimensions. The PXRD patterns of the MAPbI$_3$ nanostructures (FIG. 4) show the diffraction peak intensity increases dramatically as the reaction time increases, indicating a significant enhancement in the crystallinity of MAPbI$_3$ nanostructures. By fitting the PXRD patterns, unit cell parameters of a=0.8884 nm, c=1.2690 nm were obtained. Moreover, the clear split of the (220) and (004) peaks (highlighted in the box to the right) further confirmed the as-grown MAPbI$_3$ nanostructures were the tetragonal phase and have high crystal quality. The appearance of (002) and (004) peaks as reaction time increases may also suggest the MAPbI$_3$ nanoplates preferentially orientate along the (001) direction.

Figure 5A:
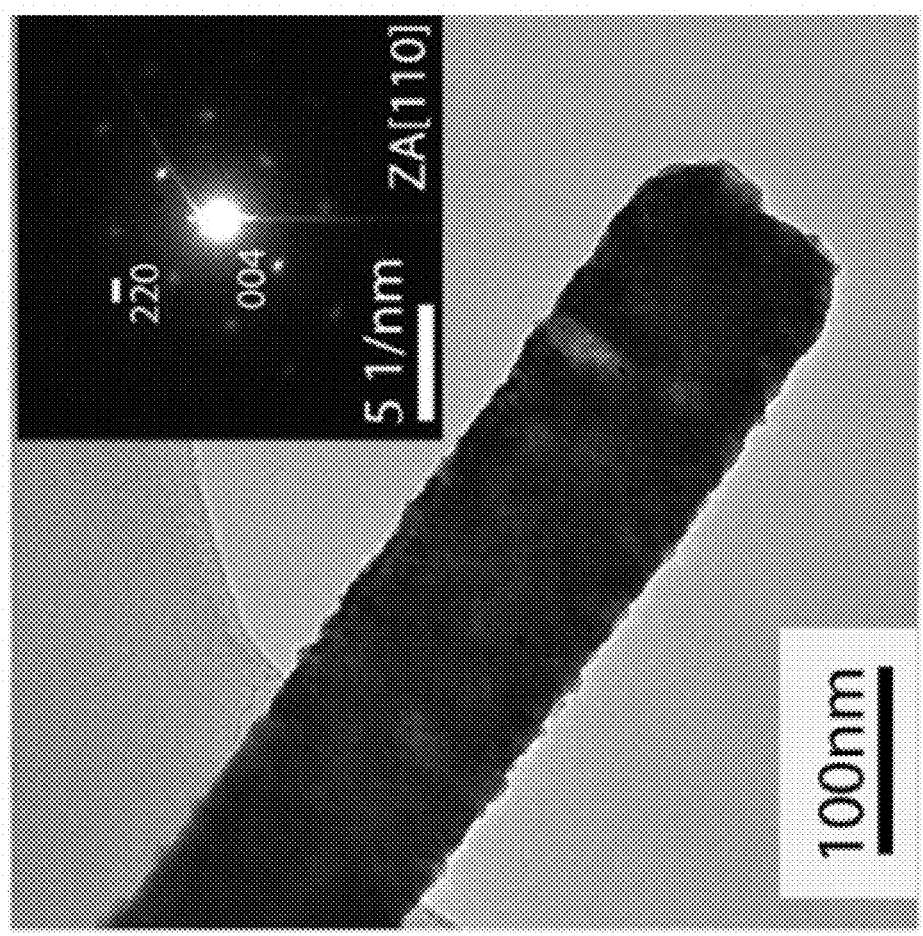
FIGS. 5A-5C show transmission electron microscopy (TEM) characterizations of single crystal MAPbI$_3$ NW and nanoplate and optical characterizations of single crystal MAPbI$_3$ nanostructures and bulk crystal.
Figures 5B, 5C:
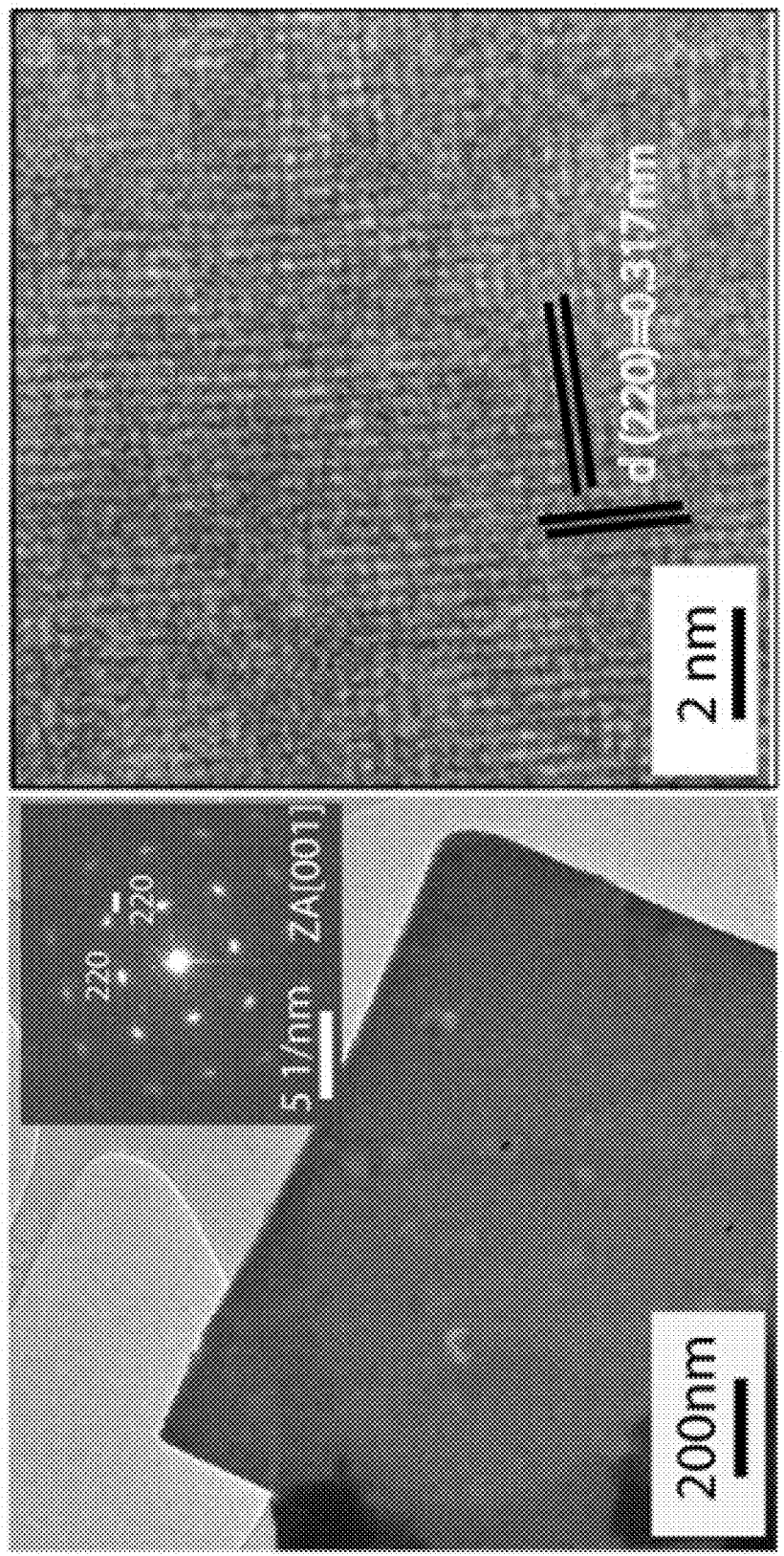

The transmission electron microscope (TEM) and electron diffraction (ED) analysis of the MAPbI$_3$ nanostructures further confirms the crystal structure and single crystal nature of the products (FIGS. 5A-5C). Representative low-resolution TEM images (FIGS. 5A, 5B) of some representative NW and nanoplate obtained under 120 kV electron beam confirm the product is single crystalline. The sharp diffraction spots seen in the corresponding SAED patterns shown in the insets can be indexed to a tetragonal perovskite crystal structure with the zone axes (ZA) of [110] or [001]. It is clear that the large flat facets of the MAPbI$_3$ nanoplates are the c planes of the tetragonal perovskite crystal structure. The acquisition of high resolution TEM on NWs is challenging, due to instability of NWs under 200 kV electron beam. Nevertheless, the nanoplates appear slightly more stable than NWs, likely due to their larger size. The stability made it possible to obtain lattice-resolved high resolution TEM (HRTEM) images. A representative HRTEM image of a MAPbI$_3$ nanoplate (FIG. 5C) shows an interplanar distance of ~0.317 nm, which can be attributed to the (220) family planes and is in good agreement with the tetragonal lattice parameters calculated from PXRD data ($d_{220}$=0.314 nm).

Physical property and optical study of single crystal MAPbI$_3$ nanostructures. These single crystal nanostructures were further used to characterize the fundamental physical properties of MAPbI$_3$. In order to determine whether the nanostructures are intrinsic or slightly doped n-type semiconductors, the MAPbI$_3$ nanostructures (shown in FIG. 3D) were studied using time-resolved surface photoresponse (SPR) measurements, which is a contactless technique to reveal charge separation on the surface of a material. The positive sign of the SPR signal (data not shown) indicates an accumulation of positive charges at the surface. For an n-type semiconductor, there is often upward band-bending near the surface, since most semiconductors have their surface Fermi levels pinned approximately near the middle of the bandgap. This position causes an accumulation of holes near the surface upon exciting the semiconductors. Therefore, the sign of the signal observed in the SPR measurements confirms that these single crystal MAPbI$_3$ nanostructures are n-type semiconductors, which is similar to the n-type doping observed for polycrystalline MAPbI$_3$ thin films which were also synthesized (data not shown).

Figure 6B:
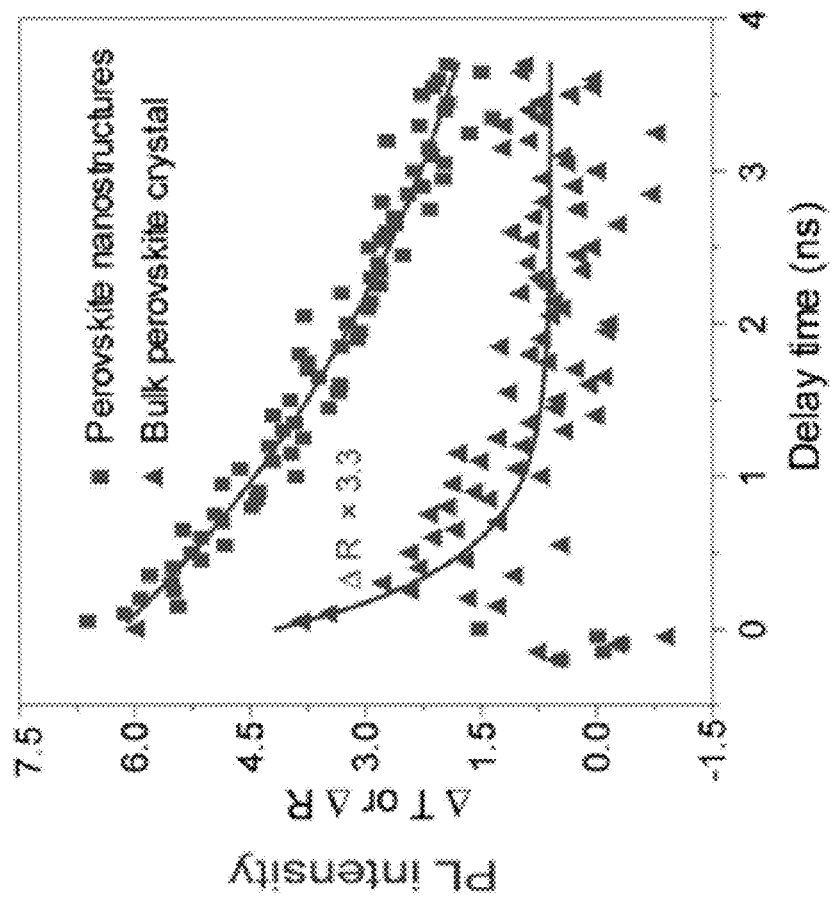
FIGS. 6A-6B compare optical characterizations of single crystal MAPbI$_3$ nanostructures and bulk crystal.
Figure 6A:
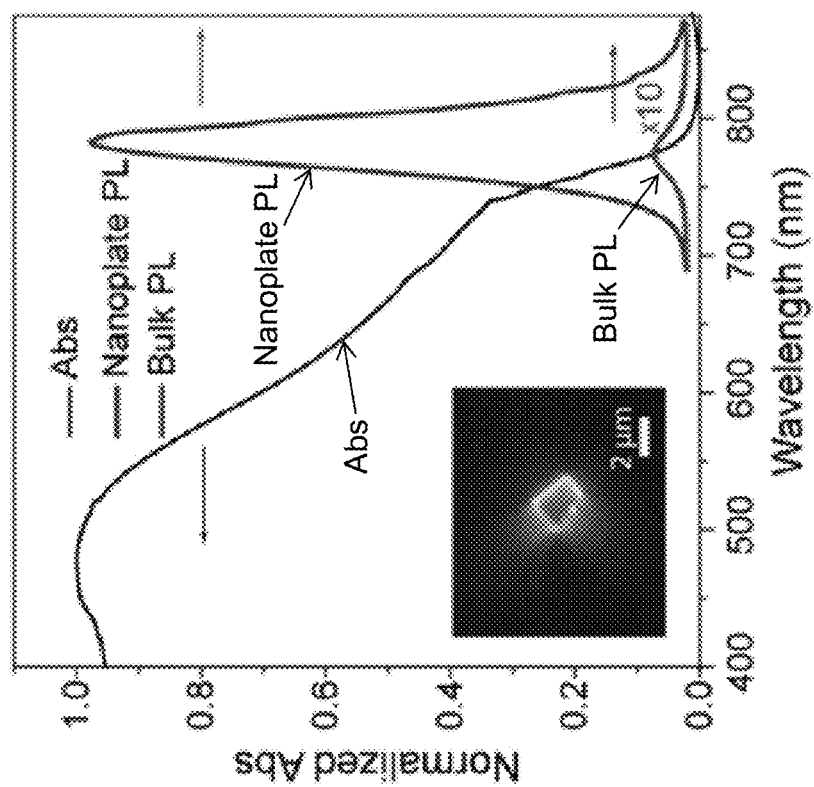

Preliminary optical studies showed that these single-crystal MAPbI$_3$ nanostructures have better photophysical characteristics than the polycrystalline thin films commonly reported and bulk crystals grown from aqueous solutions. The nanoplates were transferred from FTO to silicon substrates coated with $SiO_2$ (330 nm) by the dry transfer method. The photoluminescence (PL) of the single objects was collected with a confocal Raman microscope using a 532 nm laser source. The onset of the $MAPbI_3$ film absorption spectrum (FIG. 6A) occurs at ~790 nm, corresponding to a bandgap of 1.57 eV. The representative confocal PL spectrum of a single $MAPbI_3$ nanoplate (FIG. 6A) at room temperature shows a band-edge emission peak of 784 nm with a width at half maximum of ~40 nm. The inset in FIG. 6A shows a typical dark-field microscopy image of a single perovskite nanoplate. Also measured was the PL of a bulk $MAPbI_3$ single crystal grown by slow precipitation from aqueous solution of hydroiodic acid containing lead precursor and methylammonium iodide (see Experimental Section for detail) following a reported synthesis. (Poglitsch, A.; Weber, D. *Journal of Chemical Physics* 1987, 87, 6373.) Photographs of such bulk crystals are shown in FIGS. 7A-7B. A much weaker PL (~200 times weaker intensity than that from nanoplate) was detected from the bulk crystal (FIG. 6A).

In order to better understand the photoexcited charge carrier dynamics, ultrafast pump-probe spectroscopy measurements were further performed on $MAPbI_3$ nanostructures and bulk single crystals. FIG. 6B shows photoexcited carrier kinetics of both $MAPbI_3$ samples at a low pump fluence of 9.8 $\mu J/cm^2$. The $MAPbI_3$ nanostructures exhibit a carrier lifetime of 3.0 ns in a single exponential fit, while the bulk single crystal presents a much faster decay component with a lifetime of 0.47 ns after photoexcitation. The faster decay of photoexcited carriers and weaker PL in the bulk crystal is likely due to surface trap mediated nonradiative recombination. Therefore, even though the crystal structure of the bulk and nanostructures is identical, different preparation methods may be the cause of higher (surface) defect density in bulk single crystals, which is likely due to the severe loss of MAI that is more soluble in water when the single crystals are taken from aqueous solutions. Furthermore, the carrier lifetime observed for these $MAPbI_3$ nanostructures is also longer than that reported for typical solution-processed polycrystalline thin films observed under similar pump fluence. (Xing, G. C.; Mathews, N.; Sun, S. Y.; Lim, S. S.; Lam, Y. M.; Gratzel, M.; Mhaisalkar, S.; Sum, T. C. *Science* 2013, 342, 344; Yamada, Y.; Nakamura, T.; Endo, M.; Wakamiya, A.; Kanemitsu, Y. *Journal of the American Chemical Society* 2014, 136, 11610; Manser, J. S.; Kamat, P. V. *Nature Photonics* 2014, 8, 737.) In conclusion, the stronger room-temperature PL and longer carrier lifetime observed in these as-grown single crystal $MAPbI_3$ nanostructures indicate superior optical and semiconducting quality.

Figure 9:
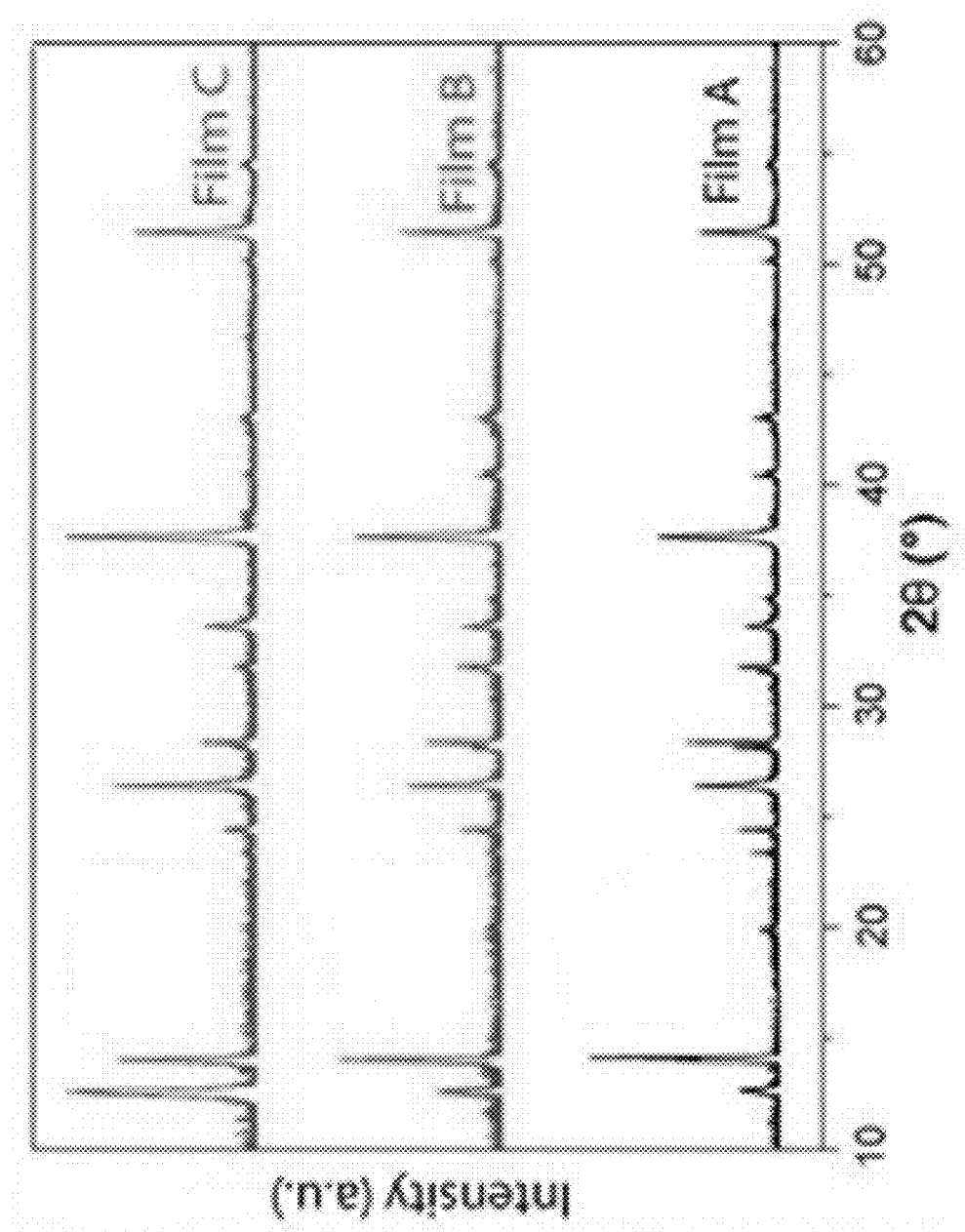
FIG. 9 shows the PXRD patterns of the as-converted MAPbI$_3$ films of FIGS. 8A-8C.

Growth of nanostructured $MAPbI_3$ films for photovoltaic application. As presented above, single crystal $MAPbI_3$ NWs and nanoplates can be synthesized using MAI/IPA solutions within a concentration range of 20-50 mg/mL. However, when 10 mg/mL MAI/IPA solution was used, small cubic-like $MAPbI_3$ grains of a few hundred nanometers are formed on the surface (FIG. 1B) and result in incomplete conversion. Surprisingly, it was found that the morphology of the converted $MAPbI_3$ changed significantly as the MAI concentration decreased slightly below 10 mg/mL. SEM images of $MAPbI_3$ films converted at 5 mg/mL, 7.5 mg/mL and 10 mg/mL with a reaction time of 2 min were obtained (films A,B, C, respectively) are shown in FIGS. 8A-8C. The A and B films are distinctly different. Film A had micro-sized (1-2 µm) "island-like" polycrystalline domains with a poor coverage on FTO, while film B had ~0.5-1 µm polycrystalline grains and almost full coverage on FTO. Film C had very good coverage but much smaller domain size, typical of perovskite thin film conversion. The physical appearance of the three films was also significantly different. The color of film C formed with 10 mg/mL MAI/IPA became light brown immediately (within 1 s) as $PbI_2$ was immersed into the solution. But, the color was almost unchanged during the remaining time suggesting that further conversion was obstructed. However, the color for the converted film B with 7.5 mg/mL MAI concentration gradually turned from yellow to brown and then to red black in ~90 s. For the 5 mg/mL MAI concentration, the sample (Film A) gradually changed to black with progressive exposure of the underlying FTO substrate over~60 s. The corresponding PXRD patterns shown in FIG. 9 showed that all as-converted products are the perovskite phase, even though some $PbI_2$ remained. Also, film A and film B have better crystallinity than film C, as indicated by the split of (004) and (220) diffraction peaks near the 2θ of 28°.

Photovoltaic devices were then fabricated with these polycrystalline nanostructured $MAPbI_3$ films and investigated (see Experimental Section for details of device fabrication and measurement). The J-V curves were obtained (data not shown). The device parameters are tabulated in Table 1.

TABLE 1

Photovoltaic device parameters of perovskite solar cells constructed with nanostructured $MAPbI_3$ film A, film B and film C.

| Device | $V_{oc}$ (V) | $J_{sc}$ (mA/cm$^2$) | FF | η % |
|---|---|---|---|---|
| Film A | 0.634 | 4.9 | 0.26 | 0.8 |
| Film B | 0.900 | 21.0 | 0.55 | 10.6 |
| Film C | 1.07 | 3.9 | 0.50 | 1.4 |

Results showed that film B had the best photovoltaic performance with a short-circuit current density ($J_{sc}$) of 21.0 mA/cm$^2$, an open-circuit voltage ($V_{oc}$) of 900 mV, a fill factor (FF) of 0.55, and a power conversion efficiency of 10.6%. The very poor performance of film A is likely due to the discontinuities caused by numerous pin-holes in the film. The pin-holes in $MAPbI_3$ film can cause serious recombination, resulting in a decrease in $V_{oc}$ and $J_{sc}$. Film C had a higher $V_{oc}$ than film B, but the $J_{sc}$ was much smaller. The higher $V_{oc}$ can be explained by the full coverage, while the smaller $J_{sc}$ is likely due to the less complete conversion into perovskite in film C. Moreover, the film B showed much higher light absorption than film C (data not shown). Compared to the single-crystal nanostructures in FIG. 3D, the absorption spectra and PL spectra of these micro-sized crystals (film A and B) displayed a small blue shift in the absorption edge and PL peak (data not shown), which is in agreement with the finding that larger crystallites present smaller band gap reported by D'Innocenzo et al. (D'Innocenzo, V.; Srimath Kandada, A. R.; De Bastiani, M.; Gandini, M.; Petrozza, A. *J. Am. Chem. Soc.* 2014, 136, 17730.) Moreover, film B showed similar carrier dynamics to the single-crystal nanostructures (data not shown), suggesting "single crystal-like" properties in such micro-sized crystals films. However, it is noted that it is difficult to create micro-sized nanostructured $MAPbI_3$ films with full coverage consistently, since the morphology of such converted nanostructures is very sensitive to the MAI concentration and the morphology of pre-deposited $PbI_2$ film.

Figures 10A, 10B:
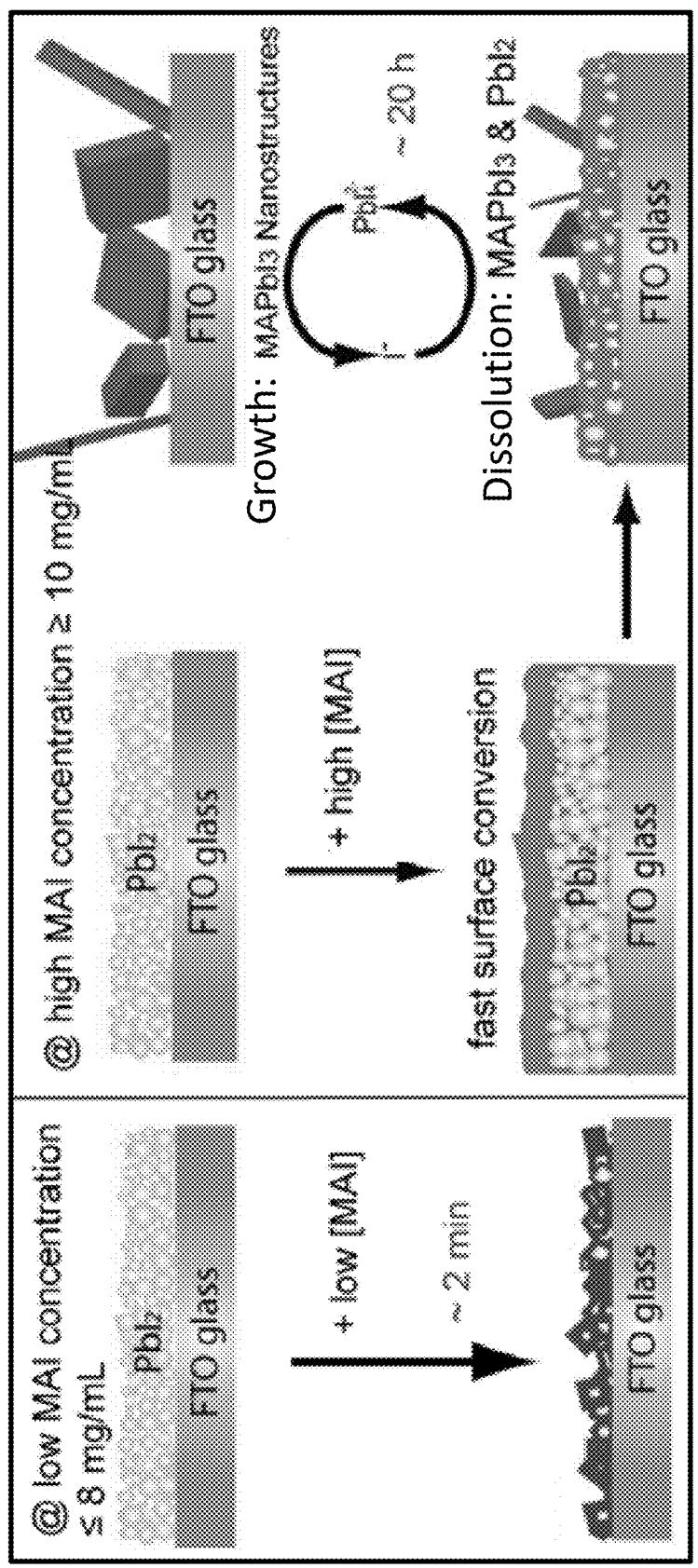
FIGS. 10A-10B show schematic illustrations of two growth mechanisms of crystalline MAPbI$_3$ nanostructures: corresponding to one growth pathway at a lower MAI concentration (FIG. 10A) and another, distinct growth pathway at a higher MAI concentration (FIG. 10B). The first growth pathway (FIG. 10A) is faster than the second growth pathway (FIG. 10B).

Growth mechanisms of crystalline MAPbI$_3$ nanostructures. Without wishing to be bound by theory, two growth mechanisms are proposed for the crystal growth of MAPbI$_3$. The first growth mechanism, which dominates at low concentration (≤8 mg/mL) of MAI precursor, is illustrated in FIG. 10A. The second growth mechanism, which dominates at high concentration (≥10 mg/mL) of MAI precursor, is illustrated in FIG. 10B. Only the second growth mechanism provides single crystalline nanostructures. At low concentration (≤8 mg/mL) of MAI precursor, diffusion of the MAI into the layered structured PbI$_2$ results in the direct formation of MAPbI$_3$, following the reaction (a) below. The reaction will be gradually suppressed as crystalline MAPbI$_3$ forms on the surface and obstructs further MA$^+$ diffusion into the underlying PbI$_2$. The obstruction may lead to the incomplete conversion seen in FIGS. 8B and 8C.

$$PbI_2(s)+CH_3NH_3^+(sol)+I^-(sol) \rightarrow CH_3NH_3PbI_3(s) \quad (a)$$

However, at higher MAI concentrations (≥10 mg/mL), crystalline MAPbI$_3$ thin film immediately forms on the PbI$_2$ surface and severely obstructs the diffusion of MA$^+$ and I$^-$ ions and their reaction with PbI$_2$. This mechanism results in rather incomplete conversion after a short period of reaction as confirmed by PXRD (FIG. 2). However, further increases in MAI and thus I$^-$ concentration (≥20 mg/mL) results in the thermodynamically favorable formation of PbI$_4^{2-}$ complex ions in the solution. PbI$_2$ becomes more soluble in concentrated iodide solution due to the formation of lead iodide complex ions (PbI$_4^{2-}$). Such excess amount of I$^-$ ions may provide the driving force that dissolves the initially formed MAPbI$_3$ and the buried, unconverted PbI$_2$ by the following reactions until the local concentration of PbI$_4^{2-}$ reaches saturation:

$$CH_3NH_3PbI_3(s)+I^-(sol) \rightarrow CH_3NH_3^+(sol)+PbI_4^{2-}(sol) \quad (b)$$

$$PbI_2(s)+2I^-(sol) \rightarrow PbI_4^{2-}(sol) \quad (c)$$

After the MAI solution is oversaturated with PbI$_4^{2-}$ complexes, PbI$_4^{2-}$ ions will react with CH$_3$NH$_3^+$ ions and slowly recrystallize to grow single crystal MAPbI$_3$ NWs and nanoplates (reaction d).

$$PbI_4^{2-}(sol)+CH_3NH_3^+(sol) \rightarrow CH_3NH_3PbI_3(s)+I^-(sol) \quad (d)$$

The proper local low supersaturation of crystal growth precursors and the slow release of precursor from the surface as controlled by reaction (c) may facilitate the anisotropic crystal growth and formation of 1D NWs, NRs, and 2D nanoplates. However, if MAI concentration is too high (≥70 mg mg/mL), most PbI$_2$ precursor gets dissolved and exists as PbI$_4^{2-}$ in the solution, and only very little can reprecipitate to form MAPbI$_3$ nanostructures (FIG. 1H).

The growth behaviors observed when MABr was used to replace MAI precursor further confirmed the growth mechanisms discussed above. With a low MABr concentration of 4 mg/mL and a reaction time of 1 min, the PXRD (data not shown) showed diffraction peaks at 14.71°, 20.93° and 29.80°, which can be assigned to the (100), (110) and (200) lattice planes of MAPbI$_2$Br. The PL had a strong emission at 739 nm (data not shown) that is characteristic of the MAPbI$_2$Br phase. SEM images of the as-converted film revealed cubic-like polycrystalline grains (data not shown) similar to FIG. 8B. The formation of mixed halide MAPbI$_2$Br confirmed that the first growth reaction mechanism dominates at a low MABr or MAI precursor concentration.

$$PbI_2(s)+CH_3NH_3^+(sol)+Br^-(sol) \rightarrow CH_3NH_3PbI_2Br(s) \quad (e)$$

However, when the MABr concentration was 12 mg/mL and the reaction time was 1 min, the PXRD (data not shown) showed the (100) and (200) diffraction peaks shifted to higher angles 14.81° and 29.96°, respectively, indicating the as-converted film becomes MAPbI$_x$Br$_{3-x}$. However, there was still unconverted PbI$_2$ in the film. The corresponding SEM showed that a compact layer of MAPbI$_x$Br$_{3-x}$ was formed on the surface with many points of nucleation (data not shown). When the reaction time was further increased to 4 h, the PXRD showed diffraction peaks at 14.83°, 21.12° and 30.04° corresponding to the (100), (110) and (200) lattice planes of the cubic MAPbBr$_3$ phase (Space group Pm$\bar{3}$m, a=5.9334 Å) and the diffraction peak from PbI$_2$ disappeared (data not shown). The SEM image showed NWs (of single crystal MAPbBr$_3$) were grown on the surface (data not shown). These MAPbBr$_3$ NWs were ~2 µm in length and around 100 nm in diameter. These MAPbBr$_3$ NWs also showed very strong PL at room temperature (data not shown). Following the discussion of the second growth mechanism above, the high concentrations of Br$^-$ ions from MABr precursor may result in the dissolution of PbI$_2$ to form PbBr$_4^{2-}$ complexes due to the overwhelming excess of Br$^-$ ions in the reaction (f), and thus enable the growth of pure MAPbBr$_3$ NWs after they recrystallize with the CH$_3$NH$_3^+$ ions following the reaction (g).

$$PbI_2(s)+4Br^-(sol) \rightarrow PbBr_4^{2-}(sol)+2I^-(sol) \quad (f)$$

$$PbBr_4^{2-}(sol)+CH_3NH_3^+(sol) \rightarrow CH_3NH_3PbBr_3(s)+Br^-(sol) \quad (g)$$

It was further shown that the lead precursor is not limited to PbI$_2$ to grow MAPbI$_3$ NWs and nanoplates. PbI$_2$ was replaced with lead acetate trihydrate (PbAc$_2$·3H$_2$O) and single crystal MAPbI$_3$ nanostructures were also synthesized. The lead acetate was deposited on the FTO substrate by spin coating a lead acetate trihydrate aqueous solution. Due to the partial hydrolysis of lead acetate, the resulting film was actually 3PbAc$_2$·PbO·H$_2$O as revealed by PXRD (data not shown). Nevertheless, it was very clear that MAPbI$_3$ NWs and nanoplates could be readily grown at the 40 mg/mL MAI/IPA solution concentration and a 1 h reaction time. The PXRD (data not shown) confirmed that the as-grown product was the pure tetragonal phase MAPbI$_3$. Interestingly, it was found that this approach also leads to a faster growth of MAPbI$_3$ than when PbI$_2$ is used as precursor. The length of the NWs reached 6 µm in a short amount of time, almost triple of the NWs in FIG. 1B. The size of nanoplates was also much larger. The faster growth may occur because PbAc$_2$ is much more soluble than PbI$_2$, and thus PbI$_4^{2-}$ complexes are formed and become saturated for crystal growth more quickly.

Conclusion

In conclusion, we have demonstrated the synthesis of single crystal MAPbI$_3$ nanowires, nanorods and nanoplates via a distinct growth mechanism in the solution conversion from PbI$_2$ (and PbAc$_2$) to MAPbI$_3$. PXRD and TEM confirm the good single-crystal quality and tetragonal perovskite phase of these nanostructures. These single crystal nanostructures are identified as n-type semiconductors by surface photovoltage measurement. Moreover, these nanostructures have stronger room temperature photoluminescence and longer excited state lifetimes than their bulk and thin film counterparts. These single-crystal nanostructures not only can serve as model systems for studying the fundamental electrical transport and optical properties of MAPbI$_3$ and improving them for solar energy conversion applications, but also can be interesting building blocks for nanophotonic/ electronic applications, for example, nanowire lasers, as further discussed in Example 2, below.

Example 2

Lead Halide Perovskite Nanowire Lasers

This example is derived from Zhu H., et. al., Lead halide perovskites nanowire lasers with low lasing threshold and high quality factors, *Nature Materials* 14, 636-642 (2015), which is hereby incorporated by reference in its entirety.

Materials and Methods

All chemicals and regents were purchased from Sigma-Aldrich and used as received unless noted otherwise.

Synthesis of $CH_3NH_3X$ (X=I, Br, Cl). $CH_3NH_3I$ was synthesized by slowly mixing 60 mL of methylamine (40% in methanol) and 65 mL of HI (57 wt % in water by weight) in a flask in an ice bath with stirring. The $CH_3NH_3I$ salt precipitated as the solvent was carefully removed at 50° C. on a rotate evaporator (Buchi R215, Switzerland). The yellowish raw product was washed with diethyl ether. The purified product was collected by filtration and dried at 80° C. in a vacuum oven for 24 h.

$CH_3NH_3Br$ (or $CH_3NH_3Cl$) was synthesized by slowly mixing 30 mL of methylamine (40% in methanol) and 28 mL of HBr (48 wt % in water by weight) [or 20 mL of HCl (37 wt % in water by weight)] in a beaker in an ice bath with stirring. Most water was then evaporated on a hot plate in a fume hood. The remaining salt was collected by filtration and washed with diethyl ether several times. Finally, the product was dried at 80° C. in a vacuum oven for 24 h.

Growth of single crystal $CH_3NH_3PbX_3$ (X=I, Br, Cl) perovskite and mixed halide nanowires. The single crystal $CH_3NH_3PbX_3$ nanowires were synthesized from a $PbAc_2$ thin film immersed in a $CH_3NH_3X$ solution in isopropanol (IPA) at room temperature (22° C.) in ambient environment. $PbAc_2$ thin film was prepared by dropcasting 100 mg/mL $PbAc_2 \cdot 3H_2O$ aqueous solution on a glass slide (placed in an oven at 65° C.), and then dried for another 30 min at 65° C. The mass loading was ~1 mg/cm². For the synthesis of $CH_3NH_3PbI_3$ nanowires, a piece of glass slide (~1-2 cm²) coated with $PbAc_2$ was carefully placed in 1 mL 40 mg/mL $CH_3NH_3I/IPA$ solution, with the $PbAc_2$ coated side facing up. For the synthesis of $CH_3NH_3PbBr_3$ (or $CH_3NH_3PbCl_3$) nanowires, the $PbAc_2$ glass slide was placed in 1 mL $CH_3NH_3Br/IPA$ (or $CH_3NH_3Cl/IPA$) solution with a concentration of 5 mg/mL, with the $PbAc_2$ coated side facing down.

For the synthesis of $CH_3NH_3PbBr_yI_{3-y}$ nanowires, the $PbAc_2$ film was placed with the $PbAc_2$ coated side facing down in 1 mL of mixed $CH_3NH_3I$ and $CH_3NH_3Br$ in IPA solution with a concentration ratio of 16:6, 16:4, 12:4, 10:6 and 2:7 mg/mL. Note, the $PbAc_2$ film was first pre-dipped into 40 mg/mL $CH_3NH_3I/IPA$ solution for ~10 s to form a "seeding layer". For the synthesis of $CH_3NH_3PbCl_xBr_{3-x}$ nanowires, the $PbAc_2$ film was placed with the $PbAc_2$ coated side facing down at 50° C. in 1 mL of mixed $CH_3NH_3Br$ and $CH_3NH_3Cl$ in IPA solution with a concentration ratio of 4:1 and 3.5:1.5 mg/mL. All the experiments were performed in air and at room temperature (22° C.) without any heating procedure, except for the synthesis of $CH_3NH_3PbBr_yI_{3-y}$ nanowires which was carried out in an oven at 50° C. After a reaction time of ~20 h, the glass slide was taken out, and subsequently dipped into isopropanol for ~5s to remove the residual salt on the film. The product was then dried under a stream of nitrogen flow.

Structural characterizations. The optical images of $CH_3NH_3PbX_3$ nanostructures were obtained on an Olympus BX51M optical microscopy. The scanning electron microscopy (SEM) images were collected on a LEO SUPRA 55 VP field-emission SEM operated at 1.5 kV. The resolution is 0.01°. The PXRD data were acquired on a Siemens STOE diffractometer with Cu Kα radiation. Note that some minor peaks associated with Cu Kβ radiation not completely filtered out in the instrument were observed in the PXRD (data not shown) and reflect the high crystalline quality of the samples. They and x value in $CH_3NH_3PbBr_yI_{3-y}$ (and $CH_3NH_3PbCl_xBr_{3-x}$) can be estimated by assuming the lattice parameter change linearly with y (and x) value. The sample for transmission electron microscope (TEM) was prepared by dry transfer of as-grown $CH_3NH_3PbI_3$ nanostructures onto a TEM grid (Ted Pella, lacey carbon type-A support film, 300-mesh, copper, #01890-F). The TEM images were acquired on a FEI Titan Aberration-corrected (S)TEM at an accelerating voltage of 200 kV. The image was taken in a fast operation using a large spot size to minimized sample damage by the electron beam. Energy-dispersive X-ray spectroscopy (EDX) was performed on single $CH_3NH_3PbX_3$ NWs transferred onto a $SiO_2$/Si wafer using a LEO 1530 field-emission SEM equipped with an EDS detector operating at 10.0 kV.

Optical characterization. Optically pumped lasing measurements were carried out on a home-build far field epi-fluorescence microscope setup (Olympus, IX73 inverted microscope). NWs on the as-grown substrate were dry-transferred and dispersed onto a silicon substrate covered with a 300 nm thick layer of silica. Each sample was mounted in a $N_2$ gas filled cell for optical measurements. The 402 nm excitation light was generated from the second harmonic of the fundamental output (805 nm, 100 fs, 250 kHz) of a regenerative amplifier (Coherent RegA amplifier seeded by Coherent Mira oscillator). The light was focused onto the sample surface by a 50X, NA=0.5 objective (Olympus LMPLFLN50X) and the pulse duration was broadened to ~150 fs. Laser beam size was optimized using a lens in front of the microscope to give a beam waist of 34 μm (FWHM) to ensure uniform illumination of each NW. The polarization of the excitation beam was not changed since the absorption anisotropy in these NWs was small (<10%). The emission from each NW was collected by the same objective and focused into a spectrograph (Princeton Instruments, IsoPlane 160) with 1200 g/mm grating and detected by a liquid-$N_2$ cooled CCD (PyLoN 400 and PyLon IR). The instrument resolution (FWHM) was ~0.1 nm. All measurements were carried out at room temperature. Time resolved photoluminescence (TRPL) decay kinetics were collected on a single NW using a TCSPC module (B&H, SPC130) and a SPAD detector (IDQ, id100-50) with an instrument response function of ~100 ps (FWHM).

Introduction

In searching for an ideal material for NW lasing, this Example turns to a new class of hybrid organic-inorganic semiconductors, methyl ammonium lead halide perovskites ($CH_3NH_3PbX_3$, X=I, Br, Cl). This Example demonstrates the growth of high-quality single-crystal NWs from low temperature solution processing. Room temperature lasing in these NWs is demonstrated with (i) record-low lasing thresholds; (ii) record-high quality factors; (iii) near unity quantum yield, and (iv) broad tunability covering the near IR to visible wavelength region. These observations establish single crystal perovskite as the most efficient material system for NW lasers, and the order(s) of magnitude improvement in efficiency over all other conventional NW lasers significantly reduces the barriers towards achieving electrically injected NW lasing and towards integration into optoelectronic and sensing devices.

Results and Discussion

High-quality single-crystal NWs were synthesized using a lead acetate (PbAc$_2$) solid thin film deposited on glass substrate in contact with a high concentration of CH$_3$NH$_3$X (X=Cl, Br, or I) solution in isopropanol at room temperature (see Materials and Methods). Similar to the second growth mechanism discussed in Example 1, the following two-step growth mechanism for the growth of single crystal NWs and other nanostructures is proposed:

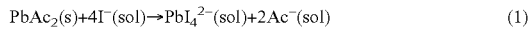

$$PbAc_2(s)+4I^-(sol) \rightarrow PbI_4^{2-}(sol)+2Ac^-(sol) \qquad (1)$$

$$PbI_4^{2-}(sol)+CH_3NH_3^+(sol) \rightarrow CH_3NH_3PbI_3(s)+I^-(sol) \qquad (2).$$

The key to successful nanostructure growth is the slow release of the low concentration Pb precursor (PbI$_4^{2-}$) from the solid film Pb(Ac)$_2$ on the substrate and the careful tuning of the CH$_3$NH$_3$X precursor concentration to maintain a low supersaturation condition for the crystal growth of perovskites.

Optical and scanning electron microscopy (SEM) images of CH$_3$NH$_3$PbI$_3$ NWs (and a few nanoplates) on a glass substrate after 24 hour growth time were obtained (data not shown). The CH$_3$NH$_3$PbI$_3$ NWs typically had lengths up to ~20 μm, with flat rectangular end facets. FIG. 13 shows magnified SEM images of two CH$_3$NH$_3$PbI$_3$ NWs, showing a square or rectangular cross-section and flat end facets perpendicular to the longitudinal axis of the NWs. The width of the rectangular cross section was typically a few hundred nanometers; the exact dimensions and aspect ratios varied from NW to NW.

Figure 11:
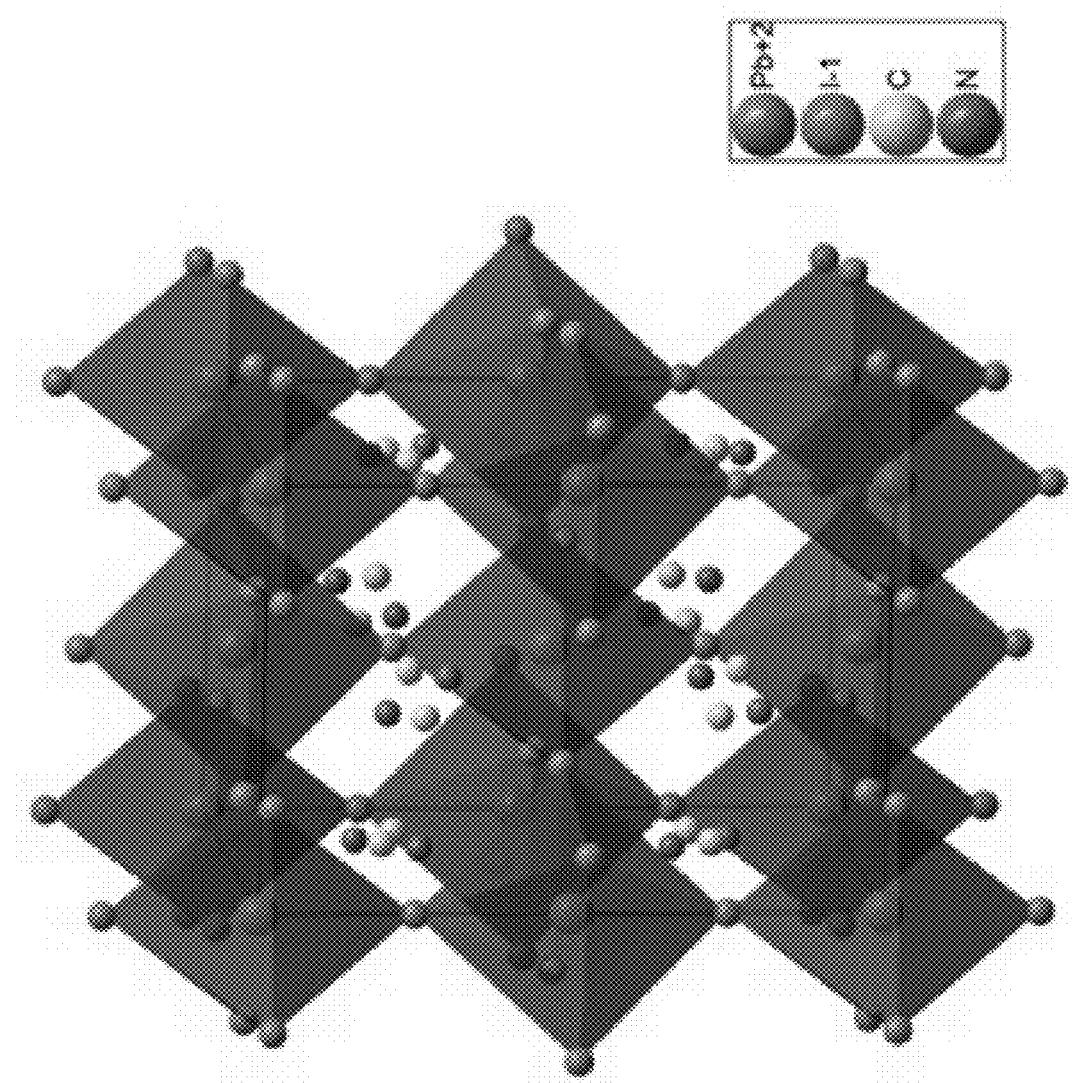
FIG. 11 shows a schematic view of the tetragonal crystal structure of CH$_3$NH$_3$PbI$_3$ perovskite.

The tetragonal crystal structure of CH$_3$NH$_3$PbI$_3$ perovskite is shown schematically in FIG. 11. Note that there are three phases of CH$_3$NH$_3$PbI$_3$. The cubic phase (Space group Pm$\bar{3}$m, a=6.276 Å) is stable at high temperature. In this ideal cubic structure, the Pb$^{2+}$ cation is in 6-fold coordination, surrounded by an octahedron of anions (PbI$_6$), and the CH$_3$NH$_3^+$ cation is in 12-fold cuboctahedral coordination. The cubic structure undergoes phase transition to a tetragonal structure (Space group I4/mcm, a=8.8743 Å, c=12.6708 Å) when the temperature is lower than 327.4 K due to the progressive ordering of the CH$_3$NH$_3^+$ ions. The tetragonal phase can be considered as a pseudo-cubic phase, in which the unit cell parameter a$_c$ can be related to that of the tetragonal cell, by a$_c$=a$_t$/$\sqrt{2}$≈c$_t$/2. When the temperature is further lowered to 162.2 K, the tetragonal phase further transitions to the orthorhombic phase (Space group Pnma, a=8.8362 Å, b=12.5804 Å, c=8.5551 Å) and the positions of CH$_3$NH$_3^+$ are fixed.

Figure 12:
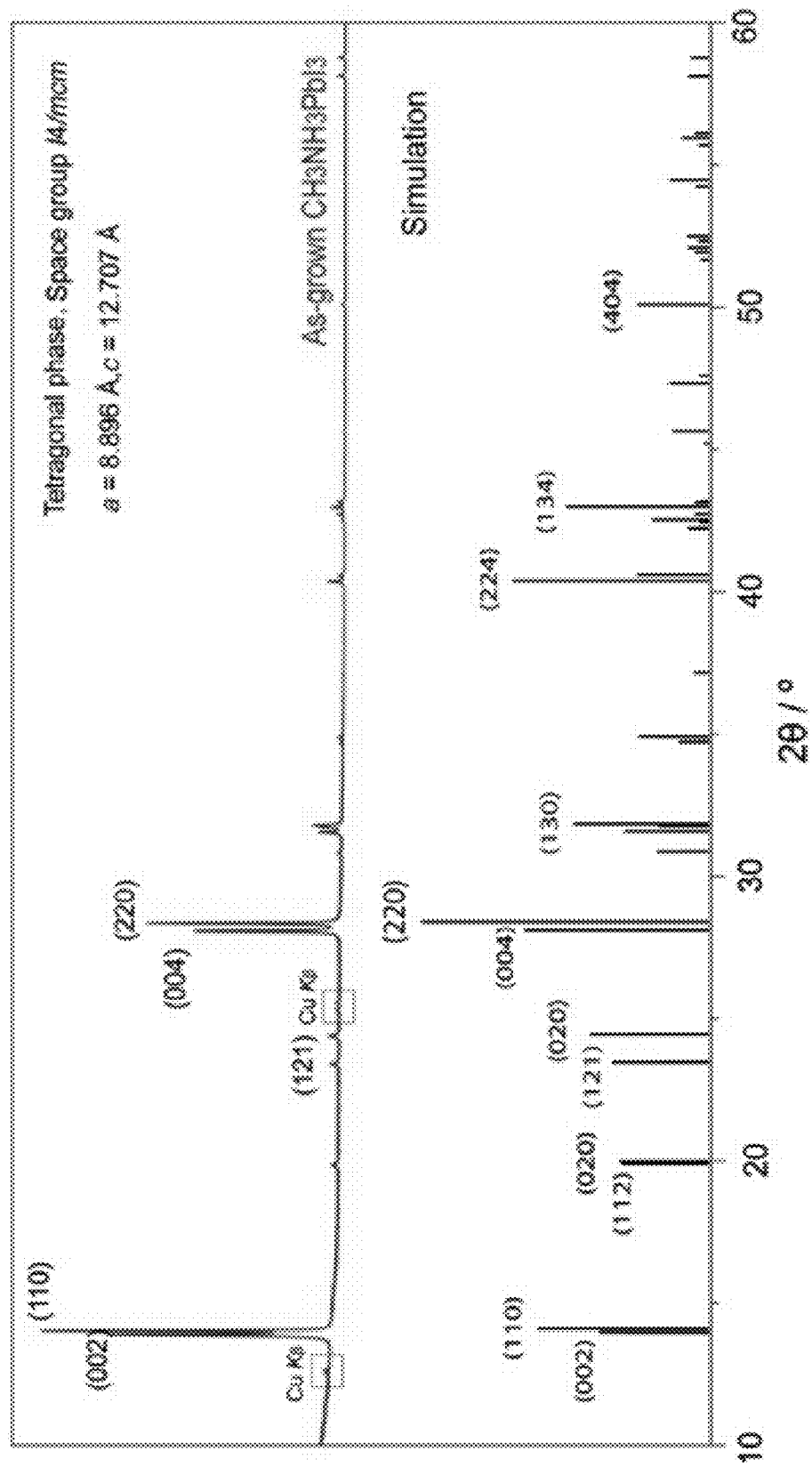
FIG. 12 shows the PXRD of as-grown CH$_3$NH$_3$PbI$_3$ nanostructures and the simulated PXRD of the tetragonal phase of CH$_3$NH$_3$PbI$_3$ perovskite.

The PXRD of as-grown CH$_3$NH$_3$PbI$_3$ nanostructures and the simulated PXRD of the tetragonal phase of CH$_3$NH$_3$PbI$_3$ perovskite, are shown in FIG. 12. The group of strong diffraction peaks could be well assigned to the tetragonal CH$_3$NH$_3$PbI$_3$ crystal structure without any impurity phases (i.e. PbI$_2$ or PbAc$_2$). The lattice parameters were calculated using Bragg's law λ=2dsinθ. The small peaks marked with rectangular boxes are diffraction peaks from Cu Kβ radiation, since Cu Kβ radiation is not completely filtered by Ni foil in our instrument. Compared to the PXRD patterns of spin-coated or vapor deposited CH$_3$NH$_3$PbI$_3$ thin films, the observation of the small (121) peak and the splitting of (220) and (004) peaks strongly confirm that the as-grown CH$_3$NH$_3$PbI$_3$ is the tetragonal phase, rather than the cubic phase, because the (121) family reflection is inconsistent with cubic symmetry and the split between (004) and (220) comes from the ordering of CH$_3$NH$_3^+$ ions in tetragonal phase.

Transmission electron microscope (TEM) analysis was also performed on single CH$_3$NH$_3$PbI$_3$ NWs (data not shown) to reveal the single crystal nature. Corresponding selected area electron diffraction (SAED) and fast Fourier transform (FFT) patterns were also obtained (data not shown). These data are similar to those presented in Example 1. The sharp diffraction spots were indexed to tetragonal crystal structure with zone axes (ZA) of [110] or [001] (which are identical directions of <100>in the pseudo-cubic lattice). The directions of [110] and [001] in tetragonal phase are not distinguishable by TEM due to the limited resolution and instability of sample in TEM. It could only be confirmed that the growth directions of NWs were [110] and/or [001] in the tetragonal lattice or <100>in the pseudo-cubic lattice. Quantitative elemental analysis from energy-dispersive X-ray spectroscopy (EDX) on individual NW yielded an I/Pb ratio of ~3, as expected from the CH$_3$NH$_3$PbI$_3$ stoichiometry (data not shown). All of these characterizations confirm high quality single crystal CH$_3$NH$_3$PbI$_3$ NWs with smooth end facets, making them ideal Fabry-Perot cavities for lasing.

Single-crystal NWs of other halide perovskites CH$_3$NH$_3$PbX$_3$ (X=Br, Cl) were also successfully synthesized by replacing CH$_3$NH$_3$I with CH$_3$NH$_3$Br or CH$_3$NH$_3$Cl. While the growth behavior was similar to that of CH$_3$NH$_3$PbI$_3$, it was found that much longer NWs (up to several tens of micrometers) could be obtained from CH$_3$NH$_3$PbBr$_3$ or CH$_3$NH$_3$PbCl$_3$ (data not shown). For CH$_3$NH$_3$PbBr$_3$ NWs, the typical length ranged from several μm up to ~100 μm. Magnified views of a CH$_3$NH$_3$PbBr$_3$ NW showed a rectangular cross section and flat, smooth facet at the end. For CH$_3$NH$_3$PbI$_3$ NWs, the length ranged from several μm to ~50 μm. Magnified views of a CH$_3$NH$_3$PbCl$_3$ NW also showed a rectangular cross section and flat, smooth facet at the end.

PXRD patterns (data not shown) confirmed the as-grown NWs and nanoplates were the cubic phase CH$_3$NH$_3$PbX$_3$ (Space group Pm$\bar{3}$m) without other impurities. EDX measurements on single NWs also confirm their stoichiometry (data not shown). It is noteworthy that, in some cases, the formation of single-crystal lead halide perovskite nanotubes was observed (data not shown). Because template-free, catalyst-free, and spontaneous formation of single-crystal hollow tubes is a signature of dislocation-driven crystal growth, this observation, together with the effectiveness of controlling the super-saturation to encourage the surface initiated NW growth, strongly suggests that the catalyst-free anisotropic growth of these lead halide perovskite NWs is likely driven by screw dislocations.

Figure 14:
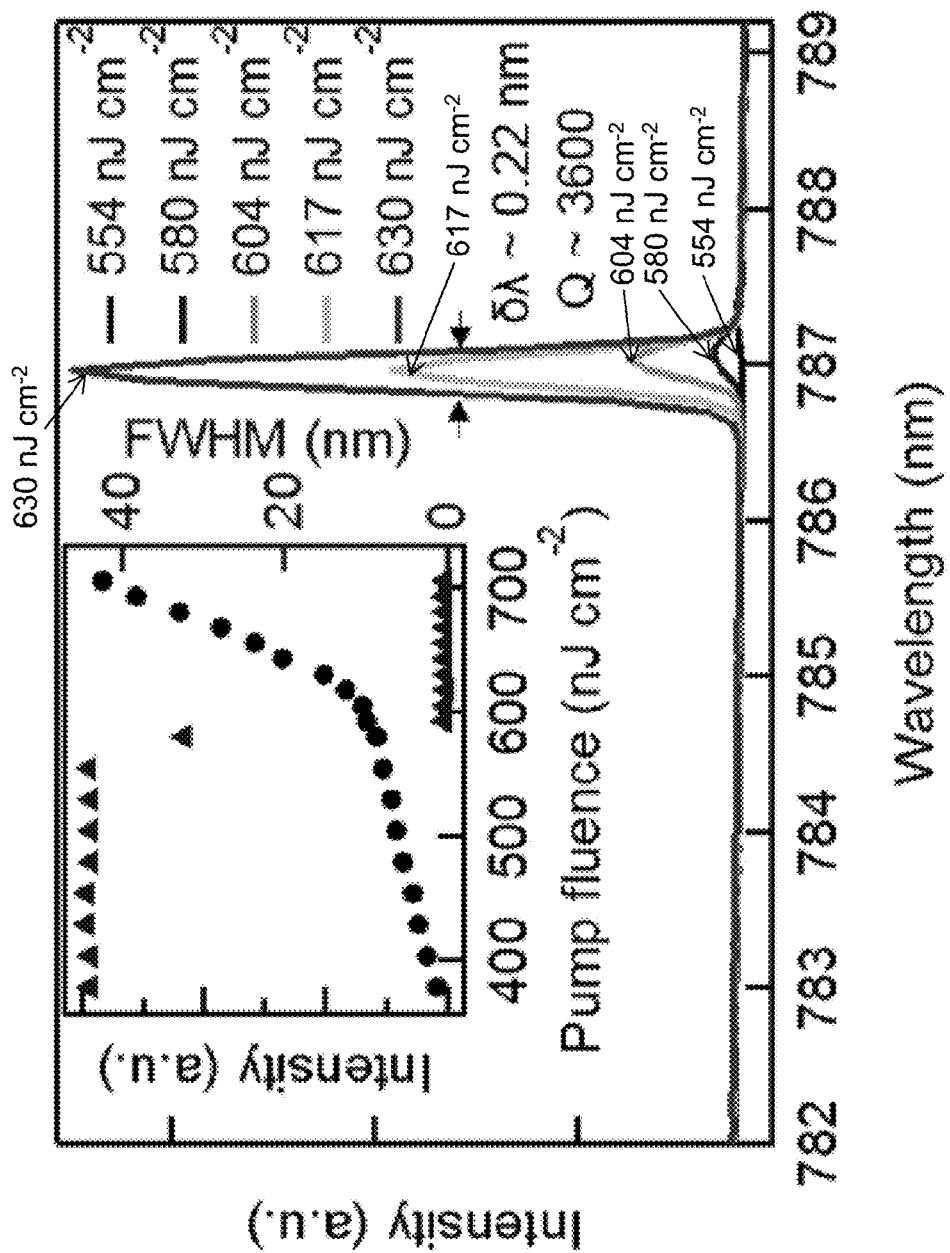
FIG. 14 shows representative NW emission spectra around the lasing threshold. The inset shows integrated emission intensity and FWHM as a function of P showing the lasing threshold at ~600 nJ cm$^{-2}$. The light-in-light-out (L-L) plot shows SPE and lasing in two linear regions. The FWHM of the lasing peak (δλ) at 630 nJ cm$^{-2}$ is 0.22 nm, corresponding to a Q factor ~3600.
Figure 15:
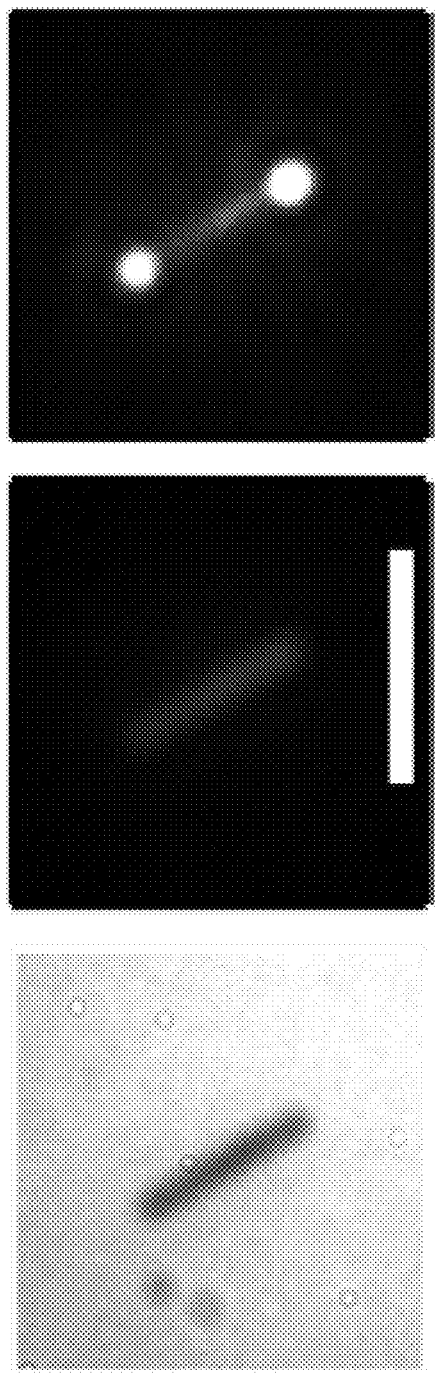
FIG. 15 shows optical images of a single NW with length of 8.5 μm. The left is an optical image. The middle and right images show the NW emission images below and above $P_{Th}$, respectively (scale bar: 10 μm). The emission is uniform below $P_{th}$ but mostly comes from two end facets with coherent interference under lasing operation.

To carry out the lasing experiment, a small number of well-dispersed perovskite NWs were transferred from the growth surface to a Si/SiO$_2$ substrate by a simple dry contact process. Optically pumped lasing measurements were performed on a home-built far field epi-fluorescence microscope at room temperature in dry N$_2$ atmosphere. A 402 nm pulsed laser beam (~150 fs, 250 kHz), with beam waist adjusted to be larger than the length of each NW, was used as nearly uniform pump source (see Materials and Methods). A two-dimensional 2D pseudo-color plot of NW emission spectra under different pump fluences (P) was obtained showing the broad spontaneous emission (SPE) peak below threshold (P$_{th}$) of ~600 nJ cm$^{-2}$ and a narrow lasing peak above threshold. Representative emission spectra near the lasing threshold are shown in FIG. 14. At low pump laser fluence (P<600 nJ·cm$^{-2}$), each emission spectrum shows a broad peak centered at ~777 nm with a full-width at half-maximum (FWHM) of δλ=44 nm; this corresponds to spontaneous emission (SPE). At P≥600 nJ cm$^{-2}$, a sharp peak at 787 nm appears and grows rapidly with increasing P, while the intensity of the broad SPE peak (non-lasing) remains almost constant (data not shown), indicating single mode lasing operation. The inset in FIG. 14 shows the light-in-light-out (L-L) data and FWHM plot as a function of P. Fitting the L-L plot to the expected S-curve model (Casperson, L. W. Threshold characteristics of multimode laser oscillators. *J. Appl. Phys.* 46, 5194-5201 (1975)) gives a room temperature lasing threshold of $P_{Th}$~595 nJ cm$^{-2}$ (data not shown). The FWHM plot shows a constant value below $P_{Th}$ and a sudden drop by more than two orders of magnitude at P≥$P_{Th}$. Additional representative L-L plot with fit to the S-curve were obtained (data not shown), further confirming lasing operation. It is noted that the emission image of the NW below $P_{Th}$ shows uniform intensity from the whole NW (middle image in FIG. 15) and that above $P_{th}$ (right image in FIG. 15) shows strong emission with spatial interference from the two coherent light sources at the two end facets. The bright emission localized at two ends is consistent with strong waveguiding effect and axial Fabry-Perot cavity modes, as confirmed later. The FWHM at P=630 nJ cm$^{-2}$, at which power the lasing peak dominates, is 0.22 nm. This gives a quality factor Q=λ/δλ~3600, which is more than an order of magnitude higher than that from the state-of-the-art GaAs-AlGaAs core-shell NW laser operating at a temperature of 4 K. (Chen, R. et al. Nanolasers grown on silicon. *Nat. Photonics* 5, 170-175 (2011).) For comparison, the Q factors from perovskite nanoplate whispering-gallery lasers were also much lower at 650~900 (Zhang, Q., Ha, S. T., Liu, X., Sum, T. C. & Xiong, Q. Room-temperature near-infrared high-q perovskite whispering-gallery planar nanolasers. *Nano Lett.* 14, 5995-6001 (2014). A small blue shift (≤0.5 nm) and broadening of the lasing peak as the pump power increases from the threshold to the highest value used are noted. The blue shift with increasing carrier density has been observed before in NW lasers and could have multiple origins: thermally induced bandgap/refractive index change, band filling, optical density fluctuations, and electron/hole many-body interactions.

Of the $CH_3NH_3PbI_3$ NWs examined (29 in total), more than 85% showed lasing, which confirms the quality of the single crystal NWs from the room temperature solution growth method. In addition to single mode lasing established in FIGS. 12-14, multiple lasing modes from some NWs were also observed (date not shown). In principle, multiple longitudinal modes in a Fabry-Perot cavity are competitive with each other and the one with the highest gain will dominate, but inhomogeneous gain saturation caused by spatial hole burning or crystal/cavity inhomogeneity can sustain multiple lasing modes. The lasing threshold of 25 NW lasers studied varies between 220 nJ·cm$^{-2}$ and 600 nJ·cm$^{-2}$. The NW lasing threshold depends on multiple factors e.g. dimensions, end facets, and crystalline quality (data not shown). The room temperature lasing threshold values of the single crystal $CH_3NH_3PbI_3$ NWs of this Example are nearly two orders of magnitude lower than those reported recently for near-IR lasing from lead halide perovskites in polycrystalline thin films or nano-plates. (Deschler, F. et al. High photoluminescence efficiency and optically pumped lasing in solution-processed mixed halide perovskite semiconductors. *J. Phys. Chem. Lett.* 5, 1421-1426 (2014); Xing, G. et al. Low-temperature solution-processed wavelength-tunable perovskites for lasing. *Nat. Mater.* 13, 476-480 (2014); Sutherland, B. R., Hoogland, S., Adachi, M. M., Wong, C. T. & Sargent, E. H. Conformal organohalide perovskites enable lasing on spherical resonators. *ACS Nano* 8, 10947-10952 (2014); Zhang, Q., Ha, S. T., Liu, X., Sum, T. C. & Xiong, Q. Room-temperature near-infrared high-q perovskite whispering-gallery planar nanolasers. *Nano Lett.* 14, 5995-6001 (2014).) The room temperature lasing threshold values of the single crystal $CH_3NH_3PbI_3$ NWs of this Example are three orders of magnitude lower than thresholds for a whole family of III-V near-IR NW lasers including those with specially engineered core-shell structures and operating at cryogenic temperatures. Based on the absorption cross-section (~5×10$^{-12}$ m$^2$ at 402 nm, calculated as described in the Supplementary Information to Zhu H., et. al., Lead halide perovskites nanowire lasers with low lasing threshold and high quality factors, *Nature Materials* 14, 636-642 (2015)), a threshold carrier density of $\rho_{Th}$=1.5-4.5×10$^{16}$ cm$^{-3}$ for pump power densities of 220-600 nJ·cm$^{-2}$ was calculated. These values are even lower than the estimated trap density of ~2×10$^{17}$ cm$^{-3}$ for polycrystalline $CH_3NH_3PbI_3$ thin films (Xing, G. et al. Low-temperature solution-processed wavelength-tunable perovskites for lasing. *Nat. Mater.* 13, 476-480 (2014)).

Figure 16:
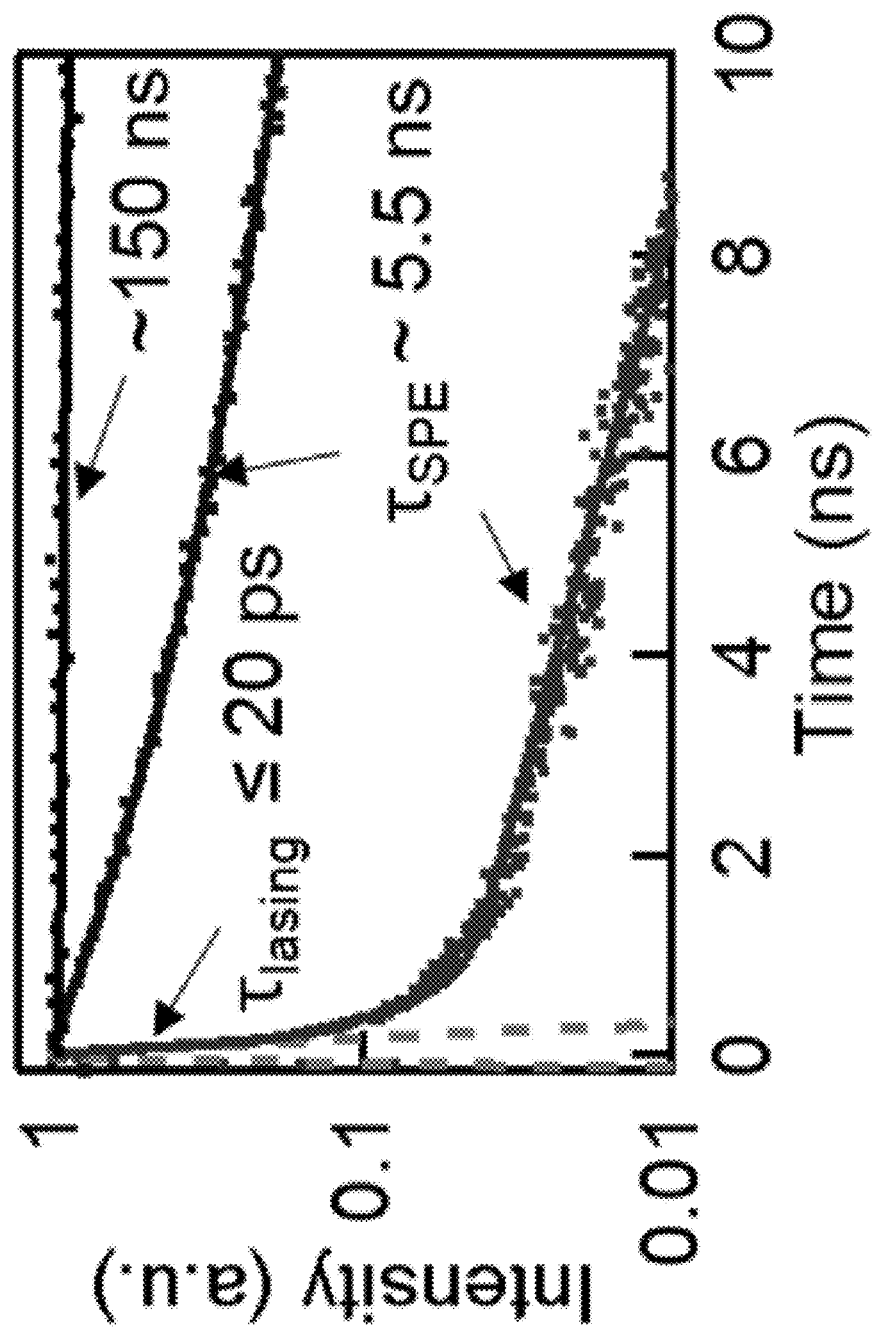
FIG. 16 shows time resolved photoluminescence (TRPL) decay kinetics after photoexcitation with fluence below (P~0.85 $P_{Th}$, middle curve) and above (P~1.1 $P_{Th}$, bottom curve) threshold, showing a ~5.5 ns spontaneous emission (SPE) decay process below $P_{Th}$ and a ≤20 ps lasing process above $P_{th}$. Also shown (top curve) is the TRPL decay kinetics with a lifetime ~150 ns at a very low photoexcited carrier density (1.5×10$^{14}$ cm$^{-3}$).

Further insight into the remarkable performance of the single crystal lead iodide perovskite NW laser comes from time-resolved photoluminescence (TRPL) measurements (FIG. 16). The SPE lifetime was as long as $\tau_{SPE}$=150 ns at low excitation densities (ρ=1.5×10$^{14}$ cm$^{-3}$ for the data points in the top curve of FIG. 16, confirming that the non-radiative decay rate is negligible $\tau_{SPE}$ decreases to 5.5 ns at high excitation density (ρ=0.85$\rho_{Th}$) before the appearance of the lasing peak (data points and fit line in middle curve of FIG. 16). Kinetic analysis of the ρ-dependent PL decay dynamics allows estimation of fluorescence quantum yields (QYs): the QY increases from ~60% at ρ=1×10$^{14}$ cm$^{-3}$ to ~87% at ρ=1×10$^{16}$ cm$^{-3}$ (as described in the Supplementary Information to Zhu H., et. al., Lead halide perovskites nanowire lasers with low lasing threshold and high quality factors, *Nature Materials* 14, 636-642 (2015)). It is expected that the PL QY will further increase to near unity (~100%), since the stimulated emission time ($\tau_{laser}$≤20 ps, instrument limited, data points and fit in bottom curve of FIG. 16) is 2-3 orders of magnitude shorter than $\tau_{SPE}$ just below the lasing threshold. For comparison, the QYs from $CH_3NH_3PbI_3$ polycrystalline thin films are <10% for SPE and ~15% for amplified SPE (Xing, G. et al. Low-temperature solution-processed wavelength-tunable perovskites for lasing. *Nat. Mater.* 13, 476-480 (2014)). As another comparison, the state-of-the-art GaAs-AlGaAs core-shell NW laser has a carrier lifetime of ~440 ps and a QY of ~0.4% (Saxena, D. et al. Optically pumped room-temperature GaAs nanowire lasers. *Nat. Photonics* 7, 963-968 (2013)). These comparisons suggest that the exceptionally low trap density in the single crystalline perovskite NWs of this Example is responsible for the superior lasing performance observed. Recent experiments on polycrystalline lead iodide perovskite thin films have pointed to a surface/interface origin of trap states, but trap states are likely absent on crystalline surfaces of low Miller indices, as is the case for the single crystal $CH_3NH_3PbX_3$ NWs of this Example. At the 1.5×10$^{16}$ cm$^{-3}$ threshold carrier density and using the reported Auger rate constant of 10$^{-28}$ cm$^6$ s$^{-1}$ nonradiative Auger recombination time of $\tau_{Auger} \propto 1/(k_{Auger}n^2)$~44 μs is estimated, which is six orders of magnitude longer than the stimulated emission lifetime (≤20 ps). The Auger loss becomes competitive only when the carrier density is 10$^3$ times higher than the lasing threshold. Without wishing to be bound to any particular theory, it is believed that the low threshold lasing in the perovskite NWs can be ascribed to a correlated electron-hole plasma (with negligible bound-exciton gas), which forms in a broad carrier density range of $10^{16}$~$10^{19}$ cm$^{-3}$. Thus, the single crystal lead halide perovskites of this Example provide extremely efficient NW lasers with high output power.

Similarly efficient lasing in the green spectral region from single crystal $CH_3NH_3PbBr_3$ NWs was also observed. Pseudo-2D presentation of emission spectra under different pump fluences and emission images above lasing thresholds for three $CH_3NH_3PbBr_3$ NWs with different lengths: (i) 7.5 µm; (ii) 13.6 µm and (iii) 23.6 µm were obtained (data not shown). In each case, a broad SPE peak (510-590 nm) was observed below $P_{Th}$ and sharp lasing peaks at ~550 nm were observed above $P_{Th}$. For P>$P_{Th}$, in all cases, interference of the two point-like coherent light sources from the two end facets of each NW was observed, confirming lasing operation. The TRPL kinetic traces of $CH_3NH_3PbBr_3$ NW below and above $P_{Th}$ were compared (data not shown). Similar to that of $CH_3NH_3PbI_3$ NWs, the TRPL data from the $CH_3NH_3PbBr_3$ NW shows ~2 ns SPE lifetime just below $P_{Th}$ and an ultrafast lasing component (≤20 ps, instrument limited) above $P_{Th}$. For the short NW ((i) 7.5 µm), one lasing peak was observed, while for the longer NWs ((ii) 13.6 µm and (iii) 23.6 µm), multiple and equally spaced lasing peaks were observed. The latter results from multiple longitudinal cavity modes with the same waveguide origin, as will be discussed later in waveguide mode simulation. The mode spacing decreases with NW length. For a cavity length L, the mode spacing ΔE is determined by $$\Delta E = \frac{hc}{2n}L^{-1},$$

where h is the Planck constant, c is the speed of light, n is the group index. The plot of mode spacing vs. reciprocal NW length ($L^{-1}$) conforms to a straight line intercepting at the origin (data not shown), confirming that the emission peaks in these NWs are indeed Fabry-Perot cavity modes. The dominant lasing peak near threshold can be fitted by a Gaussian function with FWHM=0.242±0.002 nm, corresponding to a Q factor of 2360±30. The lasing thresholds for the single crystalline $CH_3NH_3PbBr_3$ NWs vary from NW to NW: from 300 nJ·cm$^{-2}$ to 1000 nJ·cm$^{-2}$, without a clear dependence on NW length (data not shown). These $P_{Th}$ values are approximately one order of magnitude lower than the pump threshold for visible-wavelength CdS NW lasers grown by chemical vapor deposition (Agarwal, R., Barrelet, C. J. & Lieber, C. M. Lasing in single cadmium sulfide nanowire optical cavities. *Nano Lett.* 5, 917-920 (2005)). Single crystal $CH_3NH_3PbCl_3$ NWs (with bandgap emission at 410 nm) under 340 nm excitation was also examined, but lasing at room temperature was not observed, likely due to the high trap density in this material.

Figure 17:
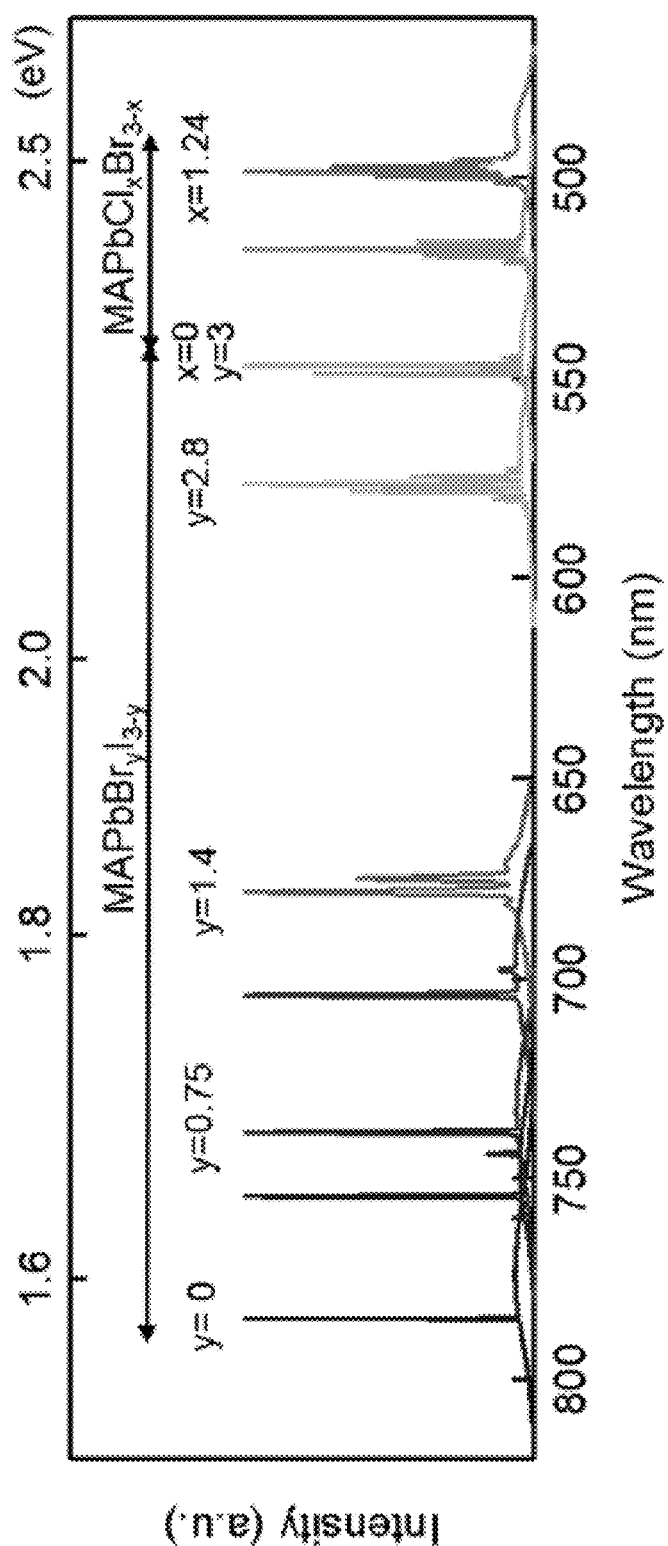
FIG. 17 shows that widely tunable lasing emission wavelength at room temperature is achieved from single crystal NW lasers of mixed lead halide perovskites.

A major advantage of lead halide perovskites for lasing application is the broad wavelength tunability based on controllable stoichiometry. This color tunability from near-IR to blue lasing in single crystal perovskite NWs is also demonstrated in this Example. By simply mixing different amounts of methylammonium (MA) iodide and bromide or bromide and chloride in the precursor solution, single crystal NWs of MAPbBr$_y$I$_{3-y}$ and MAPbCl$_x$Br$_{3-x}$ alloys with various stoichiometries were successfully synthesized. Optical and SEM images of $CH_3NH_3PbCl_{1.24}Br_{1.76}$ NWs were obtained (data not shown) as a representative case. The mixed halide NWs also display rectangular cross sections with flat end facets able to form laser cavities. The selective area SEM image and energy-dispersive X-ray spectroscopy (EDS) mapping of a single $CH_3NH_3PbCl_{1.24}Br_{1.76}$ NW (data not shown) showed uniform spatial distribution of Pb, Cl and Br throughout the NW. The PXRD of $CH_3NH_3PbCl_{1.24}Br_{1.76}$ nanostructures (data not shown) showed a set of diffraction peaks at 2θ=15.10°, 21.41° and 30.56°, which can be assigned to the (100), (110) and (200) lattice planes of the cubic perovskite phase. Compared to the PXRD patterns of pure $CH_3NH_3PbBr_3$ and $CH_3NH_3PbCl_3$, the shift of diffraction peaks clearly confirmed the alloying of Cl and Br into the as-grown NWs. The significantly blue- and red-shifted SPE peaks with respect to those of $CH_3NH_3PbBr_3$ and $CH_3NH_3PbCl_3$, respectively, confirmed the successful tuning of the NW bandgap (data not shown). Mixed bromide/iodide perovskites, MAPbBr$_y$I$_{3-y}$, were also successfully grown and the single crystal nature and lasing performance confirmed (data not shown). Therefore, the emission (SPE) of these NWs can be continuously tuned from near-IR to visible range (800-400 nm). The complete structural characterization and 2D pseudo-color plot of all NW emission spectra as a function of pump fluence were obtained (data not shown). As shown in FIG. 17, lasing operation at room temperature is observed from most NWs of mixed stoichiometry with similar or slightly higher lasing thresholds compared to those of pure lead halide (I, Br) perovskite NWs. The exception was found in MAPbCl$_x$Br$_{3-x}$ with x>1.24 and MAPbBr$_y$I$_{3-y}$ with y=2.3, where no lasing was observed under room temperature, likely a result of higher defect densities and/or poorer photostability.

Further analysis of these NW lasers shows that the lasing output is linearly polarized with high polarization purity (data not shown).

Compared to cylindrical or hexagonal NW, the rectangular cross section and geometry of these lead halide perovskite NW lasers make them more amenable and feasible for subsequent post-processing and device fabrication. The waveguide cavity lasing modes are robust in these rectangular NWs and persist after Au or Al metal thin films (5-10 nm thick) have been thermally evaporated on the top surface of $CH_3NH_3PbBr_3$ NWs (data not shown). After metal deposition, the SPE lifetime is shortened to hundreds of ps, presumably due to quenching effect from charge or energy transfer, but lasing performance is not significantly degraded. TRPL kinetics above lasing threshold again show the ultrafast stimulated lasing process (≤20 ps, instrument limited) out-competes the non-radiative loss, e.g. due to surface/interface trap state mediated recombination or energy transfer to the metal thin films (data not shown). Note that Au and Al are commonly used high and low workfunction metals for the injection of holes and electrons, respectively, and may be representative for electrode materials in the fabrication of electrically injected perovskite NW lasers. The long-term stability of these NWs was also tested and lasing measurements performed on aged NWs that have been kept in $N_2$ atmosphere (for $CH_3NH_3PbI_3$) or air (for $CH_3NH_3PbBr_3$) at room temperature and room light illumination for 4~6 months. The lasing thresholds from these aged NWs show similar or slight increased value compared with fresh NWs (data not shown). Because of the high repetition rate of the excitation laser and heat accumulation in these isolated nano objects, the lasing stability under continuous laser irradiation (with pump fluence above $P_{Th}$) degrades over a few tens of minutes. Such stability problem may be overcome with lower repetition rate and better heat transfer, and can be improved with better perovskite materials with improved thermal and photostability, as will be discussed in Example 3.

Conclusion

The results presented above establish room temperature lasing in the visible and near-IR region from single crystal perovskite NWs with the lowest lasing thresholds and highest Q factors reported to date for NW lasers. The exceptional lasing performance of lead halide perovskites can be attributed to long carrier lifetimes and low nonradiative recombination rates. In view of the unique rectangular NW geometry, the ease in growing single crystal perovskites and their nanostructures in solution phase at room temperature, the tunability of emission color across the visible spectrum with mixed halides, and the exceptional performance enhancement (lasing threshold, Q factor, and near unity quantum yield), lead halide perovskites may become the materials of choice for the implementation of NW lasers in a wide range of applications, such as nano-photonics, optical computing, and chemical/biological sensing.

Example 3

Nanowire Lasers of Formamidinium Lead Halide Perovskite and Their Stabilized Alloys Materials and Methods All chemicals and regents were purchased from Sigma-Aldrich and used as received unless noted otherwise.

Synthesis of $CH(NH_2)_2X$ (FAX, X=I, Br). The synthesis of formamidinium halide, $CH(NH_2)_2X$ (FAX, X=I, Br), followed the previous literature. (Eperon, G. E.; Stranks, S. D.; Menelaou, C.; Johnston, M. B.; Herz, L. M.; Snaith, H. *J. Energy Environ. Sci.* 2014, 7, 982-988.) Specifically, the $CH(NH_2)_2I$ or $CH(NH_2)_2Br$ was synthesized by slowly dissolving formamidinium acetate powder and HI (57 wt % in water) or HBr (48 wt % in water) in a evaporating dish in a molar ratio of 1:2. The $CH(NH_2)_2I$ or $CH(NH_2)_2Br$ salt gradually precipitated as the solvent was carefully removed at 100° C. on a hot plate. The product was collected by filtration and washed with diethyl ether several times. Finally, the product was recrystallized in ethanol to form white crystals, and dried at 50° C. in an oven for 24 hours.

Growth of hexagonal phase $CH(NH_2)_2PbI_3$ ($FAPbI_3$) nanowires and the conversion to the perovskite phase. The single-crystal hexagonal (yellow) phase $CH(NH_2)_2PbI_3$ nanowires were synthesized by immersing a piece of $PbAc_2$ coated glass slide in a 20 mg/mL $CH(NH_2)_2I$ solution in isopropanol (IPA), with the $PbAc_2$ coated side facing down in an oven at 50° C. The $PbAc_2$ thin film was prepared by dropcasting 100 mg/mL $PbAc_2 \cdot 3H_2O$ aqueous solution on a glass slide and dried at 60° C. Upon dipping the chip into the $CH(NH_2)_2I$ solution, the film turned yellow. After a reaction time of ~20 h, the glass slide was taken out, and subsequently washed in isopropanol and dried under $N_2$ flow. The perovskite (black) phase $CH(NH_2)_2PbI_3$ nanowires were obtained by annealing the chip on a hot plate at 170° C. for 5 min, which resulted in the products to turn into black color.

Growth of single-crystal $CH_3NH_3Br$ (MABr) stabilized $CH(NH_2)_2PbI_3$ perovskite NW ($FA_{0.75}MA_{0.25}$)$Pb(I_{2.7}Br_{0.3}$), $CH(NH_2)_2PbBr_3$ perovskite NW and other $(FA_{1-z}MA_z)Pb(Br_{3-y}I_y)$ alloys. To synthesize single crystal $(FA_{0.75}MA_{0.25})Pb(I_{2.7}Br_{0.3})$NWs, a $PbAc_2$ film on glass slide was first dipped into 1 mL 40 mg/mL MAI/IPA solution for ~2 min to form a "seeding layer" on the substrate surface. The substrate was then placed into 1 mL of mixed IPA solution of FAI and MABr with a concentration ratio of 20:5 mg/mL at room temperature for ~15 h, with the $PbAc_2$ coated side facing up. It was noted that the increased reaction time may cause the growth of hexagonal phase NWs. For the synthesis of $FAPbBr_3$ NWs, the $PbAc_2$ film was immersed into 1 mL of 10 mg/mL FABr/IPA solution in an oven at 50° C. for ~20 h, with the $PbAc_2$ coated side facing down. For the synthesis of $(FA_{1-z}MA_z)Pb(Br_{3-y}I_y)$ NWs, the $PbAc_2$ film was immersed into 1 mL of mixed IPA solution of FABr and MAI with a concentration ratio of 7:1, 7:2, 7:3, 7:4 and 7:5 mg/mL in an oven at 50° C. for ~20 h, with the $PbAc_2$ coated side facing down.

Thermal gravimetric analysis (TGA). The $MAPbI_3$ or $FAPbI_3$ samples for TGA were prepared through precipitation from $MAPbI_3$ or $FAPbI_3$ solution in dimethylformamide (DMF) by adding toluene as an antisolvent. Specifically, 200 mg of $PbI_2$ powder and 69 mg of MAI or 75 mg of FAI with a molar ratio of 1:1 were dissolved in 0.8 mL DMF to form a solution with a concentration of ~340 mg/mL. Upon adding ~5 mL of toluene into the solution, the $MAPbI_3$ or $FAPbI_3$ powders were precipitated and then collected by centrifuge at 10k rpm for 1 min. Finally, the $MAPbI_3$ and $FAPbI_3$ powders were dried at 100° C. and 170° C., respectively. Thermal gravimetric analyses of the as-prepared samples were performed using a TA Instruments Q500 Thermogravimetric Analyzer with a ramping rate of 2° C. $min^{-1}$ from room temperature up to ~350° C. under a nitrogen or oxygen environment with a flow rate of 50.0 mL/min.

H-NMR determination of the FA/MA ratio in the $(FA_{1-z}MA_z)Pb(Br_{3-y}I_y)$ alloys. The various perovskite alloys were prepared by adding 0.15 mL of 100 mg/mL $PbAc_2 \cdot 3H_2O$ aqueous solution into 15 mL of a mixed IPA solution of FABr and MAI with the desired concentration ratio. To ensure a complete conversion, the solution was placed in an ultrasonic bath for around 5 min. The powders were collected by centrifuging at 10k rpm for 1 min and then dried at 100° C. in the air. To carry out H-NMR, the as-prepared powders were first dispersed in methanol-d4 and the resulted suspension was further ultrasonicated to dissolve the perovskites as much as possible. Then a clear solution could be obtained by removing the undissolved powders through centrifugation and used for H-NMR measurement using a Bruker 400 MHz NMR spectrometer. HNMR (400 MHz, methanol-1-d) of FAI: 7.86 δ (s, 1H). HNMR (400 MHz, methanol-1-d) of MAI: 2.56 δ (s, 3H).

Structural characterizations. The optical images of $FA(MA)PbX_3$ nanostructures were obtained on an Olympus BX51M optical microscope. The scanning electron microscopy (SEM) images were collected on a LEO SUPRA 55 VP field-emission scanning electron microscope operated at 3 kV. Energy-dispersive X-ray spectroscopy (EDX) was performed on single NWs transferred onto a $SiO_2$/Si wafer using a LEO SUPRA 55 VP field-emission SEM equipped with an EDS detector operating at 15.0 kV. The PXRD data were collected on as-grown samples on glass substrates using a Bruker D8 Advance Powder X-ray Diffractometer with Cu Kα radiation.

Optical characterization. The optically pumped lasing measurements were carried out on a home-build far field epifluorescence microscope setup (Olympus, IX73 inverted microscope). NWs on as-grown substrates were dry-transferred and dispersed onto a silicon substrate covered with a 300 nm silica layer; each sample was mounted in a $N_2$ gas filled cell for optical measurements. The 402 nm excitation light was generated from the second harmonic of the fundamental output (805 nm, 100 fs, 250 kHz) from a regenerative amplifier (Coherent RegA amplifier seeded by Coherent Mira oscillator). The light was focused onto the sample surface by a 50X, NA=0.5 objective (Olympus LMPLFLN50X) and the pulse duration was broadened to ~150 fs. The laser beam size was optimized by using lens in front of microscope to give a beam waist of 34 μm (FWHM) to ensure uniform illumination of each NW. The polarization of the excitation beam was not changed since the absorption anisotropy in these NWs was small (<10%). The emission from each NW was collected by the same objective and focused into a spectrograph (Princeton Instruments, IsoPlane 160) with 1200 g/mm grating and detected by a liquid-$N_2$ cooled CCD (PyLoN 400 and PyLon IR). The instrument spectral resolution (FWHM) was ~0.1 nm. All measurements were carried out at room temperature. Time resolved photoluminescence (TRPL) decay kinetics was collected on single NWs using a TCSPC module (B&H, SPC130) and a SPAD detector (IDQ, id100-50) with an instrument response function ~100 ps (FWHM).

Introduction

Three-dimensional (3D) organic-inorganic hybrid perovskite may adopt the formula of $ABX_3$ (see FIG. 18 for crystal structure), in which A is an organic cation, B is a metal ion (e.g., $Pb^{2+}$, $Sn^{2+}$) and X is a halide anion. A major advantage of this family for light-emitting application is the wide compositional substitution towards to A, B and X sites, which allows for tailoring the optical and physical properties. For example, the exchange of the organic cation of the $MAPbI_3$ perovskite from methylammonium to formamidinium ($CH(NH_2)_2^+$, FA) leads to a semiconductor with a slightly lower bandgap of 1.47 eV (which is good for solar performance), as well as better temperature and moisture stability. Thermogravimetric analysis (TGA) was carried out in a $N_2$ or $O_2$ atmosphere to compare the thermal stability of $FAPbI_3$ and $MAPbI_3$ quantitatively (data not shown), showing that the onset of decomposition temperature of $FAPbI_3$ is significantly higher than that of $MAPbI_3$, especially in the presence of $O_2$.

However, unlike $MAPbI_3$, in the solution synthesis of $FAPbI_3$, the larger radius of FA cation favors the formation of a more stable hexagonal phase instead of perovskite structure at room temperature. The hexagonal phase is an indirect bandgap semiconductor with a non-perovskite type structure, which is not suitable for photovoltaic and light-emitting applications. This Example shows low-temperature solution growth of high-quality single-crystal hexagonal phase $FAPbI_3$ NWs followed by conversion to perovskite phase NWs, and a direct solution-growth of stabilized perovskite phase of $FAPbI_3$ NW alloys by incorporating a small amount of MABr into $FAPbI_3$. Optically-pumped room-temperature efficient lasing from the $FAPbI_3$ perovskite NWs and MABr-stablized $FAPbI_3$ perovskite NWs with near-infrared (NIR) emission of ~800 nm, low lasing thresholds~several μJ cm$^{-2}$ and high quality factors ~1500 is also demonstrated. Both types of NWs have shown significantly improved lasing stability than $MAPbI_3$ NW due to the enhanced thermal stability. The $FAPbI_3$ and MABr-stabilized $FAPbI_3$ nanowires display more than one order of magnitude improvement in lasing stability over $MAPbI_3$ nanowires, with durable lasing in the former under ~6×10$^8$ shots of sustained illumination of 402 nm pulsed laser excitation (150 fs, 250 kHz) at room temperature. In addition, this Example shows the solution growth of $FAPbBr_3$ NWs, mixed cation alloys of $(FA,MA)PbI_3$ NWs and double alloys of $(FA,MA)Pb(Br,I)_3$ NWs through cations and/or halide substitutions. Owing to the better photostability and cation-induced bandgap tuning effect, a further advantage of these NWs of FA-based perovskites over MA-based perovskites is that the lasing emissions are widely tunable in the region from visible to near-infrared wavelength.

Results and Discussion

Figure 19:
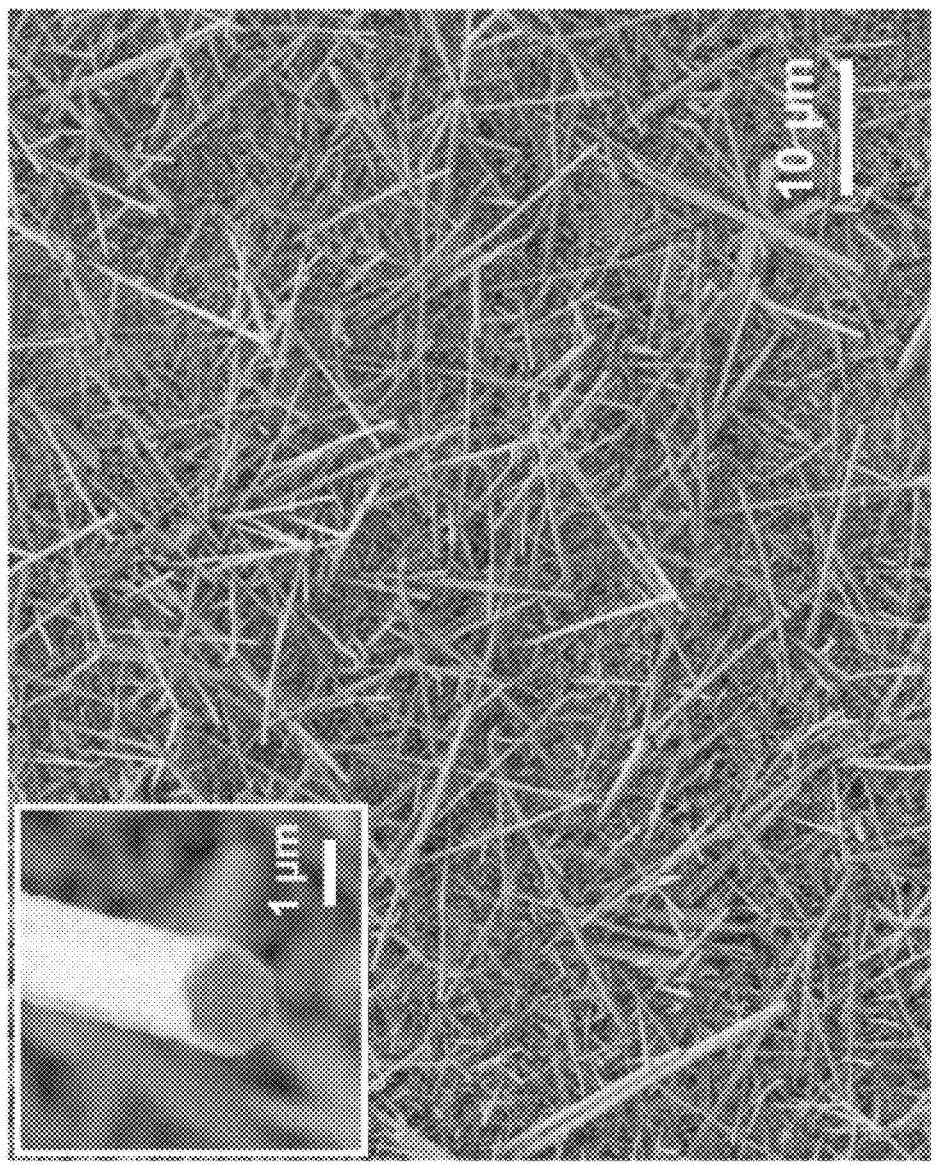
FIG. 19 shows a SEM image of as-converted perovskite phase FAPbI$_3$ NWs. The inset is a top view of a NW, showing a hexagonal cross-section and flat end facet.

Single-crystal $FAPbI_3$ NWs were successfully synthesized by reacting a lead acetate thin film deposited on a glass substrate immersed with a FAI solution in isopropanol (see Materials and Methods). However, an important difference is that the originally formed product of $FAPbI_3$ was observed to be a hexagonal phase (yellow color, non-perovskite structure) by powder X-ray diffraction (PXRD, FIG. 20, bottom curve). Scanning electron microscopy (SEM) images of hexagonal $FAPbI_3$ NWs grown on a glass substrate at 50° C. for ~20 h were obtained (data not shown). The $FAPbI_3$ NWs typically have lengths from several to tens of micrometers with flat hexagonal end facets. The diameter varies from a few hundred nanometers to several micrometers. However, the yellow products could be turned into black by heating in air at 170° C. for 5 min. The corresponding PXRD pattern (FIG. 20, middle curve) confirms the as-converted products were trigonal phase (a perovskite-type structure). Interestingly, the NW morphology and hexagonal cross section were well-preserved after conversion (FIG. 19 and the inset). Quantitative elemental analysis from energy dispersive X-ray spectroscopy (EDS) on individual NW yields an I/Pb ratio of ~3, in good agreement with the stoichiometry of $FAPbI_3$ (data not shown).

Figure 20:
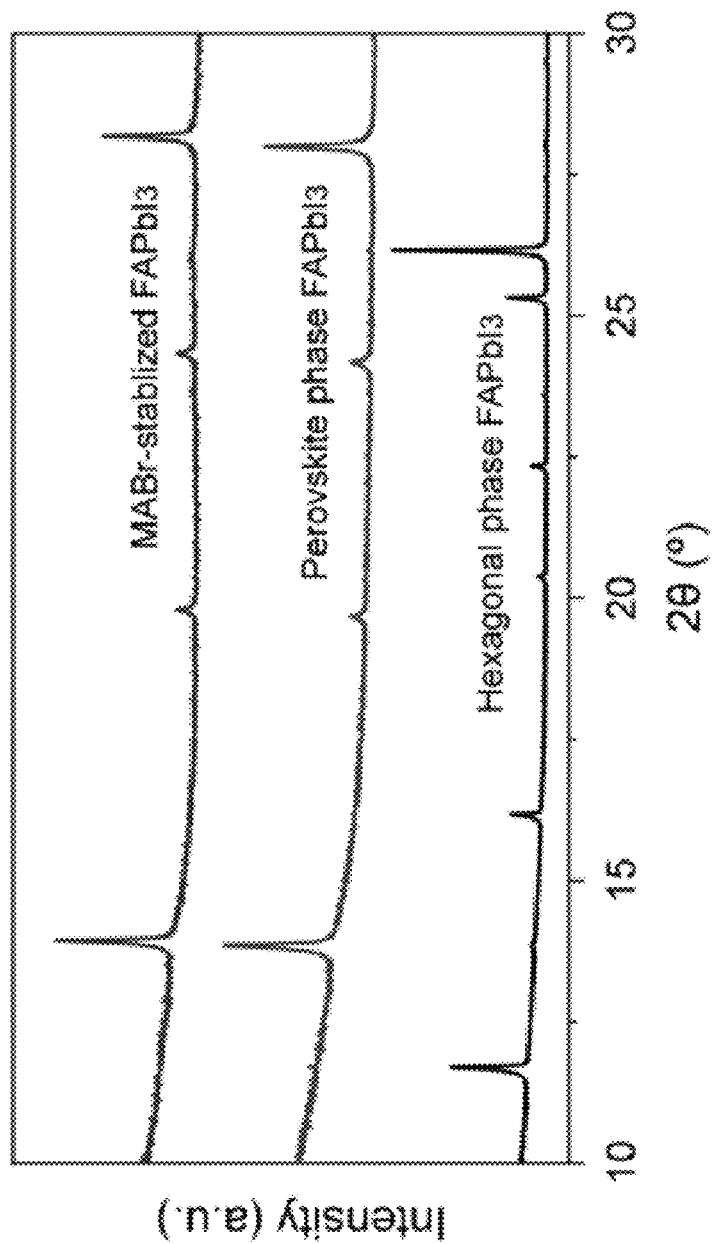
FIG. 20 shows PXRD patterns of as-prepared hexagonal phase FAPbI$_3$, perovskite phase FAPbI$_3$ and perovskite phase MABr-stablized FAPbI$_3$.
Figure 21:
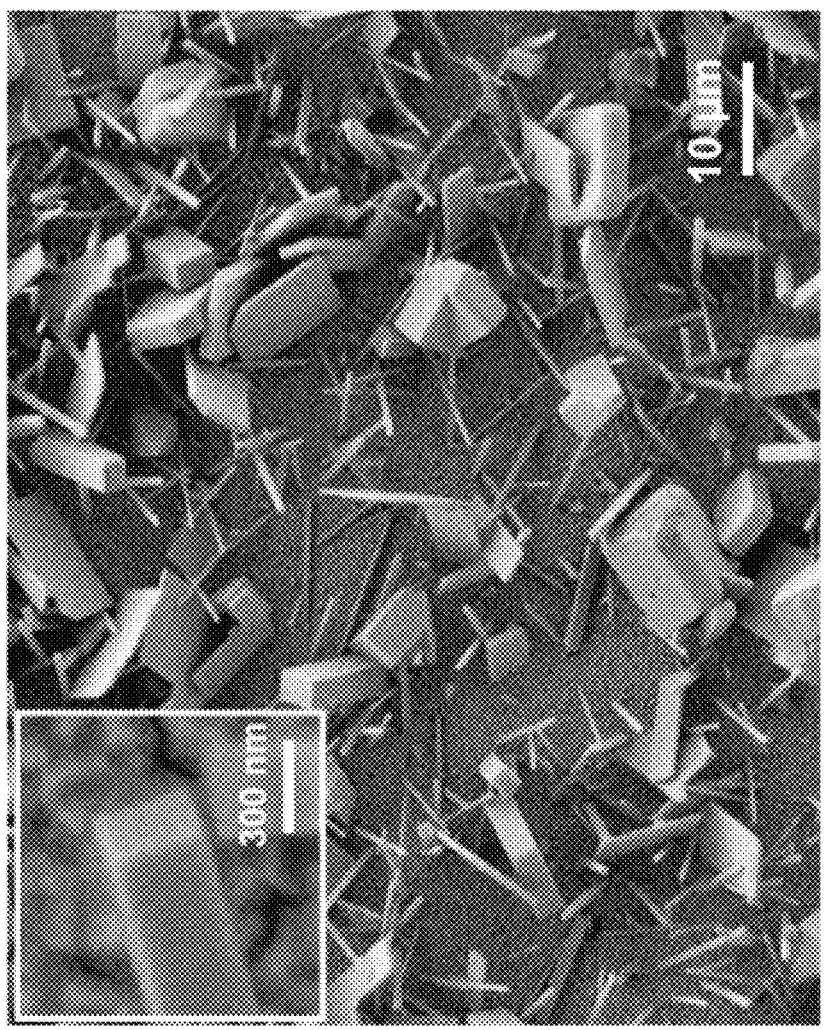
FIG. 21 shows a SEM image of as-grown MABr-stablized FAPbI$_3$ perovskite nanowires. The inset is a top view of a NW, showing a rectangular cross-section and flat end facet.

The match of radii of A, B and X ions plays a critical role in the formation and stability of perovskite structures. A tolerance factor ($a=(r_A+r_X)/\sqrt{2}(r_B+r_X)$, r is the effective ion radius) has been used to evaluate the ionic size mismatches that the perovskite structure can tolerate until a different type of crystal structure is formed. Therefore, simultaneous and synergic compositional modification of A and/or X sites may lead to the stabilization of perovskite structure of $FAPbI_3$ at room temperature. Here, it was found that stabilized single-crystal perovskite phase NW of $FAPbI_3$ alloys can be directly grown by adding small amount of MABr into FAI solution. FIG. 21 shows the SEM images of MABr-stablized $FAPbI_3$ NWs grown at mixed solution of 20 mg/mL FAI and 5 mg/mL MABr. As described in the Materials and Methods section above, a "seeding growth" method was employed in order to grow the NWs better. The inset in FIG. 21 highlights the rectangular cross section of these NWs, in contrast to the hexagonal ones seen in FIG. 19 for the converted $FAPbI_3$ NWs. FIG. 20 (top curve) shows a group of strong diffraction peaks at 13.95°, 19.80°, 24.33° and 28.17° which can be assigned to (100), (110), (111) and (200) lattice planes of the cubic perovskite phase, confirming the perovskite-type structure of as-grown products.

Energy-dispersive X-ray spectroscopy mapping of a single MABr-stablized $FAPbI_3$ NW shows uniform spatial distribution of Pb, I and Br elements (data not shown). Quantitative elemental analysis of EDS yields an I/Br ratio ~2.7/0.3. The ratio of FA/MA was further determined to be ~0.75/0.25 by using $^1$H NMR spectroscopy (data not shown). Confocal microscopy photoluminescence spectra of a single $MAPbI_3$ NW, MABr-stablized $FAPbI_3$ NW, and perovskite phase $FAPbI_3$ NW excited by a 532 nm laser source at room temperature were obtained. The confocal PL spectrum of a single MABr-stablized $FAPbI_3$ NW at room temperature showed an emission peak centered at 786 nm, which is a slight blue shifted from that of to $FAPbI_3$ NWs due to the incorporation of MABr (data not shown).

Figure 22:
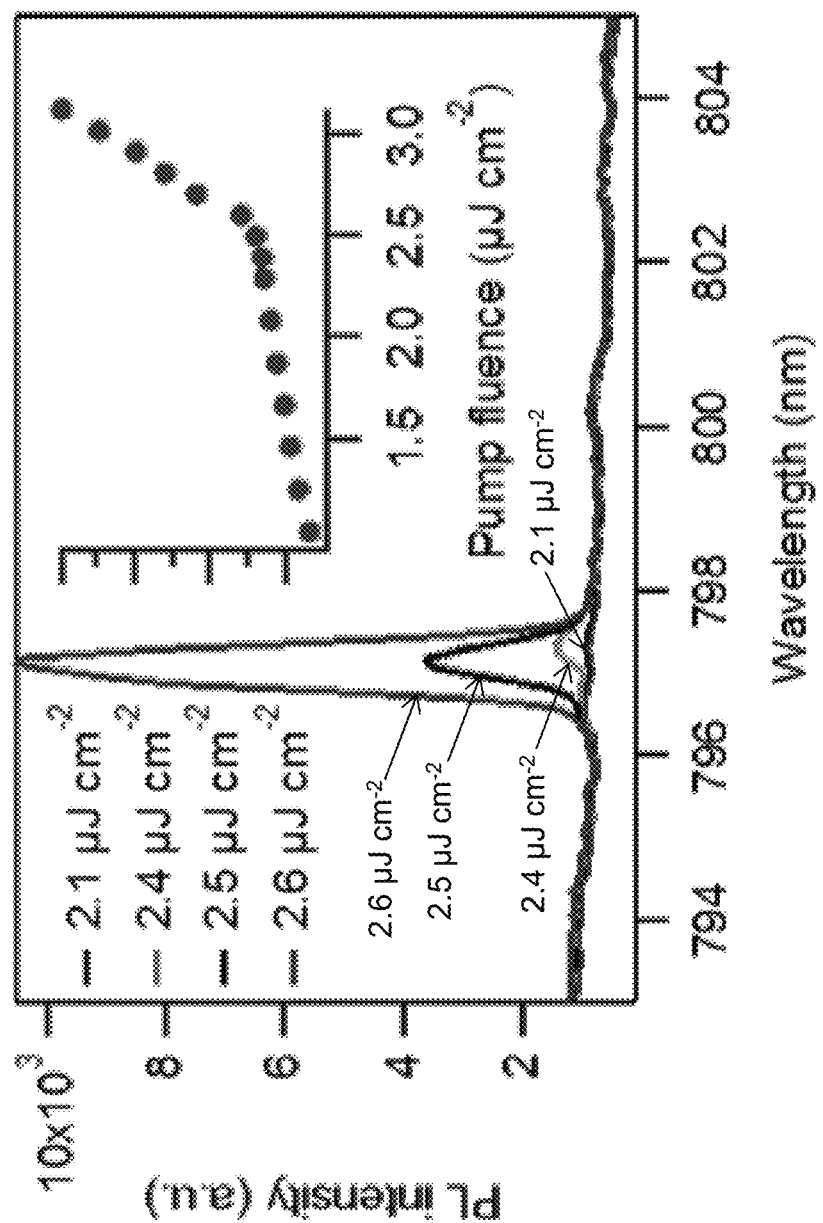
FIG. 22 shows NW emission spectra around the lasing threshold from converted perovskite phase FAPbI$_3$ NWs. Inset: Integrated emission intensity as a function of P showing the lasing threshold ~6.2 μJ cm$^{-2}$.
Figure 23:
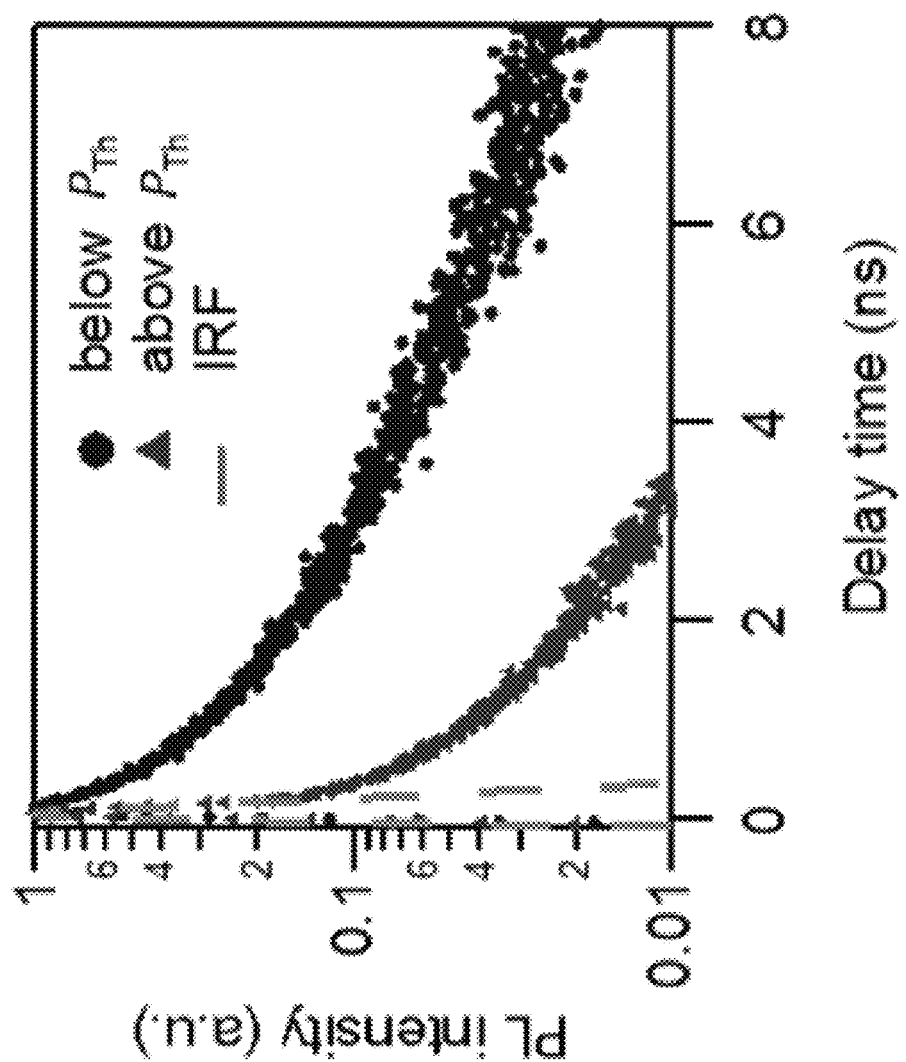
FIG. 23 shows time resolved PL decay kinetics of converted perovskite phase FAPbI$_3$ NW below (circles) and above (triangles) lasing threshold. Also shown in gray is the instrument response function (IRF).
Figure 24:
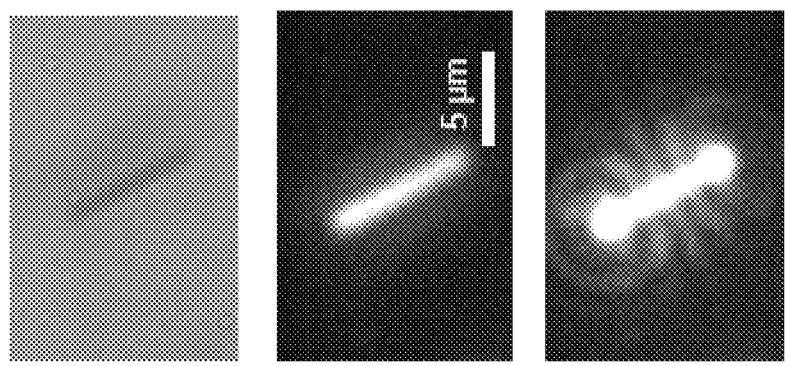
FIG. 24 shows an optical image (upper panel) and fluorescence images of a single converted perovskite phase FAPbI$_3$ NW below (middle panel) and above (lower panel) lasing threshold.

Optically pump lasing on the converted perovskite phase $FAPbI_3$ NWs were conducted on a home build inverted microscope system with 400 nm pulse light excitation (see Materials and Methods). The NW samples were dispersed on to quartz window of a nitrogen gas filled cell by dry contact transfer and kept in nitrogen atmosphere during measurements. The individual NWs were excited evenly by 400 nm laser pulse excitation. A 2D pseudo-color plot of PL spectra of a representative $FAPbI_3$ NW (with a length of ~11 μm) was obtained with pump fluence between 4.1 μJ cm$^{-2}$ and 7.8 μJ cm$^{-2}$ (data not shown). Four PL spectra around lasing threshold are shown in FIG. 22. Below the lasing threshold ($P_{Th}$) ~6.2 μJ cm$^{-2}$, $FAPbI_3$ NW shows a broad PL spectra with center ~813 nm and a full-width-at-half-maximum (FWHM) ~40 nm and the integrated PL intensity grows slowly with pump fluence (inset in FIG. 22). Above $P_{Th}$, a sharp lasing peak at ~824 nm emerges and increases quickly with pump fluence (FIG. 22), while the intensity of the spontaneous emission region approaches saturation (data not shown), indicating the lasing occurrence. The FWHM of the lasing peak ($\delta\lambda$) is ~0.53 nm, corresponding to a quality factor ($Q=\lambda/\delta\lambda$) of ~1554. Further evidence establishing NW lasing come from the time resolved PL decay kinetics and fluorescence images below and above lasing threshold (FIGS. 23 and 24, respectively). Below $P_{Th}$, $FAPbI_3$ NW shows a PL lifetime ~800 ps (FIG. 23, circles, top curve) and a uniform spontaneous emission image from NW (FIG. 24, middle). Above $P_{Th}$, an instrument-limited ultrafast PL decay component (<20 ps) can be observed from time-resolved PL kinetics, corresponding to the stimulated lasing emission (FIG. 23, triangles, middle curve). The coherent lasing emission mostly comes out from two ends of NW and forms interference pattern on fluorescence image (FIG. 24, bottom), further confirming a Fabry-Perot cavity of NW.

The lasing performance of MABr-stabilized $FAPbI_3$ perovskite NWs was also characterized. Similar to $FAPbI_3$ perovskite NWs, the 2D pseudo-color plot of a representative MABr-stablized $FAPbI_3$ NW (length ~7.5 ~m) emission spectra under different pump fluences (data not shown) showed a broad PL spectra (center ~782 nm, FWHM ~41 nm) below $P_{Th}$ (~2.6 μJ cm$^{-2}$) and a narrow lasing peak (FWHM ~0.55 nm, corresponding to Q factor of ~1450) above $P_{Th}$. Above $P_{Th}$, time-resolved PL decay kinetics also showed an instrument-limited ultrafast stimulated emission process (data not shown) and lasing interference pattern from two ends were clearly observed from fluorescence image (data not shown), confirming the lasing occurrence.

Figure 25:
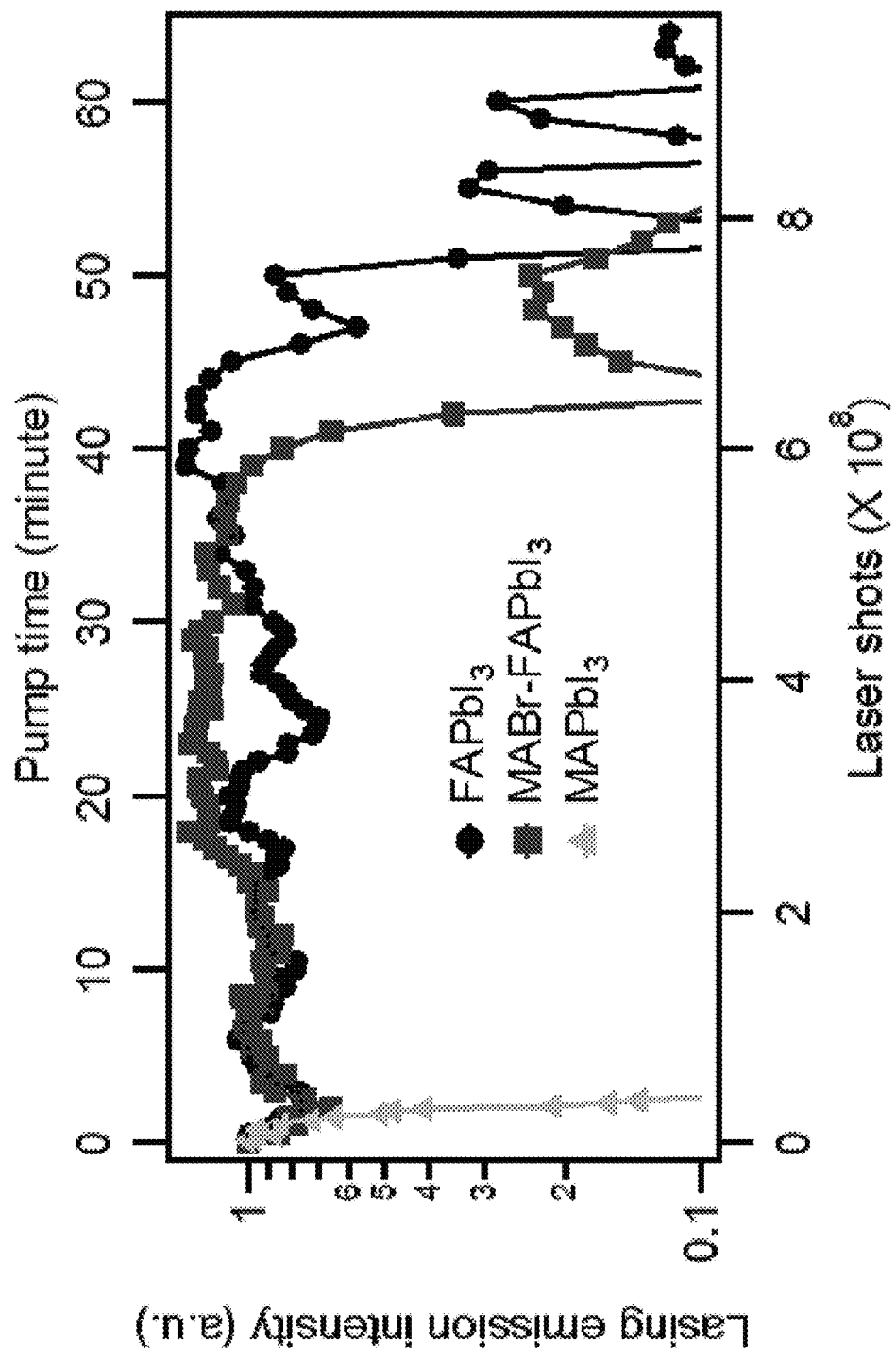
FIG. 25 shows the lasing emission intensity of FAPbI$_3$, MABr-stablized FAPbI$_3$ and MAPbI$_3$ NWs as a function of pump time with up to ~1 h of continuous illumination of 402 nm laser excitation (150 fs, 250 kHz) at room temperature.

The photostability of the lasing emission from these NWs was assessed, which is important for implementing perovskite NW lasers in optoelectronic device applications. The lasing stability of three NIR NW lasers $FAPbI_3$, MABr-$FAPbI_3$ and $MAPbI_3$ was assessed by continuously pumping them with 250 kHz laser at power density of ~1.1 $P_{Th}$. The NW lasers were on quartz window in $N_2$ gas environment without cooling. The pure lasing emission intensities from these NWs (after subtracting the spontaneous emission fraction) as a function of pumping time (or the number of excitation laser shots) are compared in FIG. 25. Note the intensity at zero time has been normalized to unity. The lasing emission intensity from $MAPbI_3$ NW started to drop after ~1 min continuous illumination (which corresponds to ~1.5×10$^7$ laser shots). In contrast, both $FAPbI_3$ and MABr-stabilized $FAPbI_3$ NW lasers show much better photostability: their lasing intensity only dropped after ~45 and ~38 min of continuous illumination, respectively. At that time, they have been excited by at least 6×10$^8$ laser pulses, which is more than one order of magnitude longer than that of $MAPbI_3$ NW lasers. The much improved photostability is consistent with their enhanced thermal stability compared with $MAPbI_3$ NW. It is expected that additional cooling/thermal management will further extend the function lifetime of these NW lasers.

Single-crystal $FAPbBr_3$ NWs, nanorods and nanoplates were also successfully synthesized by replacing FAI with FABr solution. SEM images of as-grown $FAPbBr_3$ NWs were obtained showing flat rectangular end facets (data not shown). Unlike the $FAPbI_3$ with two structural polymorphs, the as-grown $FAPbBr_3$ exists only as a single perovskite phase at room temperature. The corresponding PXRD (data not shown) showed a set of strong diffraction peaks at 14.69°, 20.88°, 29.72° and 33.33° could be well assigned to (100), (110), (111) and (120) planes of pseudo-cubic structure (space group Pm$\bar{3}$m). Compared to $MAPbBr_3$, these diffraction peaks shift to smaller angles due to the larger size of FA cation. The cation-induced tuning of electronic and optical property leads to ~10 nm red shift of PL peak when moving from MA to FA in lead bromide perovskite. Also observed was efficient lasing in the green spectra region from $FAPbBr_3$ NWs at room temperature. Emission spectra showed a broad spontaneous emission spectra centered at ~548 nm with a FWHM ~23 nm below $P_{Th}$ and narrow lasing peaks at ~560 nm with FWHM ~0.24 nm above $P_{Th}$ (corresponds to a quality factor of ~2300). Optical images showed the interference pattern from two-point coherent light sources, also confirming the lasing operation. The 2D pseudo-color plot of NW emission spectra as a function of pump fluence was also obtained (data not shown).

A remarkable advantage of lead halide perovskite system is the bandgap tunability through both cation and/or anion substitutions. Example 2 demonstrated widely tunable lasing wavelength in the spectra region from 790 nm to 500 nm except a gap between 580 nm to 670 nm based on controllable anion substitutions of $MAPbX_3$ NWs. The exception was found in $MAPbBr_{3-x}I_x$ NWs with 1.4>x>0.2, where the emission peaks were unstable under continuous laser illumination (data not shown). Photoexcitation may cause phase segregation between Br-rich and Br-poor phases in $MAPbBr_{3-x}I_x$ films due to the light-induced ion migration. (Hoke, E. T.; Slotcavage, D. J.; Dohner, E. R.; Bowring, A. R.; Karunadasa, H. I.; McGehee, M. D. *Chem. Sci.* 2015, 6, 613-617.)

Interestingly, this issue was found to be mitigated in the double alloys of FA-based perovskites that can possess much better photostability (data not shown). The NWs of perovskite double alloys of $(MA,FA)Pb(Br,I)_3$ were grown by reacting $PbAc_2$ film with a mixed solution of FABr (fixed at 7 mg/mL) and MAI in isopropanol. SEM images of an example of single-crystal NWs of double alloy grown with a mixed solution of 7 mg/mL FABr and 3 mg/mL MAI were obtained (data not shown). The PXRD pattern confirms the cubic perovskite phase of these NWs (data not shown). EDS mapping analysis on a single NW (data not shown) and $^1$H NMR spectra (data not shown) further determine a stoichiometry of $(FA_{0.67}MA_{0.33})Pb(Br_{2.69}I_{0.31})$. The PL peak of the $(MA,FA)Pb(Br,I)_3$ NWs was observed to continuously redshift until 620 nm upon increasing MAI content used in the precursor solution from 1 mg/mL to 3 mg/mL (data not shown). A series of optical images of the $(MA,FA)Pb(Br,I)_3$ NWs with increasing MAI content excited by a 442 nm laser clearly demonstrated colorful emissions and strong waveguide along the axial direction of NW (data not shown).

Figure 26:
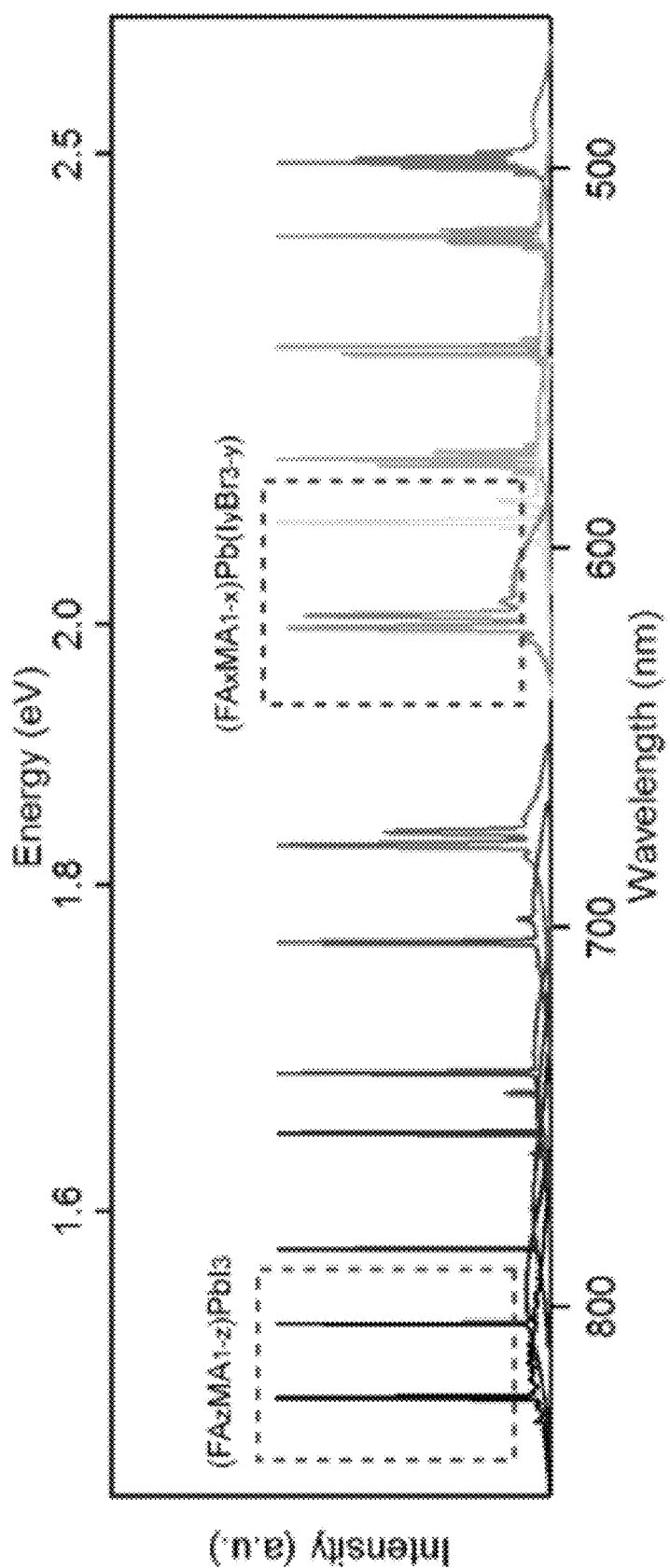
FIG. 26 illustrates broad wavelength-tunable lasing from single-crystal lead perovskite NWs. The rectangular boxes highlight the new wavelength range of emissions achieved by cation alloying (MA,FA)PbI$_3$ NWs or both cation and anion alloying in (FA,MA)Pb(Br,I)$_3$ NWs, which could not be realized in MA-based perovskite alloys. The data outside of the boxes were adapted from Example 2.

As shown in FIG. 26, room-temperature lasing operation from $(FA_{0.71}MA_{0.29})Pb(Br_{2.78}I_{0.22})$ and $(FA_{0.67}MA_{0.33})Pb(Br_{2.69}I_{0.31})$ NWs, was observed, where the lasing peaks are at 595 nm and 621 nm, respectively. The 2D pseudo-color plot of these NWs emission spectra as a function of pump fluence were obtained (data not shown). Although it can be difficult to synthesize NW of FAPb(Br,I)$_3$ alloys from a mixed FABr and FAI solution, it was found that adding a small amount of MA can promote the NWs growth. As shown in FIG. 26, with these new NW lasers based on the double alloys of (MA,FA)Pb(Br,I)$_3$, it is possible to fill in the gap of lasing wavelength previously unavailable with MA-based perovskite. In addition, efficient lasing from (FA$_{0.48}$MA$_{0.54}$)PbI$_3$ NW alloy was also demonstrated with a lasing peak at 805 nm. Detailed structure characterizations and lasing results of cation-mixed (FA,MA)PbI$_3$ NWs were obtained, confirming crystalline nature and lasing performance (data not shown). Therefore, it is clear that the alloying of both cation and/or anion widens the wavelength tunability of lead halide perovskite nanolasers and now these NW lasers can be continuously tunable from 490 nm to 824 nm (see FIG. 26).

Conclusion

In summary, the solution synthesis of high-quality single-crystal NWs of FAPbI$_3$, MABr-stabilized FAPbI$_3$, FAPbBr$_3$, (FA,MA)PbI$_3$ alloys and (FA,MA)Pb(Br,I)$_3$ double alloys have been developed. Room-temperature lasing in the visible and NIR region from these NWs with a low lasing threshold (~several μJ cm$^{-2}$) and high quality factor (~2000) has also been shown. These FA-based perovskite NWs display much better photostability and wider wavelength tunability over MA-based perovskite NWs. These results suggest the FA-based perovskites could be more promising and stable candidates for the future development of light emitting diodes and lasers based on perovskite materials. These results also demonstrate the generality of the solution synthesis of nanostructures for various families of organic-inorganic hybrid perovskite materials with different cations and anions to exploit their diverse physical properties.

Example 4

Nanoplatelets of Two-Dimensional Organic-Inorganic Lead Halide Perovskites for Optoelectronics.

Introduction

In this Example, a solution synthesis of single-crystal nanoplatelets and microrods of (PEA)$_2$PbX$_4$ and their halide alloys with uniform well-defined rectangular geometry through a dissolution-recrystallization process is reported. The growth process is further improved using solution transport growth from the precursor to product substrate and growth of ultra-thin (<50 nm) nanoplates of (PEA)$_2$PbBr$_4$ are demonstrated. The as-grown 2D sheets exhibit strong PL with color tunability from violet (~410 nm) to green (~530 nm) by changing the halide composition. These single-crystal nanostructures not only can serve as model system to understand the fundamental photophysics, such as nonlinear optical properties, quantum confinement and carrier dynamics, of layered perovskites, but also can be building blocks for nanophotonics and optoelectronics.

Materials and Methods

All chemicals and regents were purchased from Sigma-Aldrich and used as received unless specified otherwise.

Synthesis of phenethylammonium halide [C$_6$H$_5$C$_2$H$_4$NH$_3$X, (PEA)X, X=Br, I]. The phenethylammonium halides were synthesized by a similar method reported previously. Briefly, solution of HBr (48 wt. % in water) or HI (57 wt. % in water) was added slowly to phenylethylamine with an equal molar ratio of 1:1 in a flask at 0° C. Then the water was evaporated in a fume hood at an elevated temperature (~100° C.) until phenethylammonium halide crystals precipitated from the solution. After the solution was cooled down, the powder product was filtered and rinsed with diethyl ether several times before it was dried at 80° C. in a vacuum oven for ~24 h to remove the residual water.

Growth of single crystals and nanoplatelets of (PEA)$_2$PbX$_4$ (X=Br and I). First, FTO glass substrates were partially coated with a thin film of PbAc$_2$ through drop-casting an aqueous solution of PbAc$_2$.3H$_2$O (100 mg/mL) and then dried in an oven for 30 min at 60° C. The nanoplatelets of (PEA)$_2$PbBr$_4$ single crystal was synthesized in a glass vial by placing the PbAc$_2$ film into (PEA)Br solution in isopropanol with various concentration from 1 mg/mL to 8 mg/mL at room temperature, with the lead precursor-coated side facing down. After a specified reaction time typically from 1 min to ~20 h, the FTO substrate was taken out and dipped into isopropanol to remove any leftover solution on the substrate, and then dried under a stream of nitrogen flow. The occasionally found large single crystals with lateral dimensions above 100 micrometers were picked up for single-crystal X-ray structure analysis.

For the solution transport growth of (PEA)$_2$PbX$_4$ nanoplatelets and their alloys, a clean substrate, such as a Si wafer or a CaF$_2$ substrate, was first placed on the bottom of a glass vial containing 10 mg/mL PEABr solution, or 15 mg/mL PEAI solution, or a mixed solution of PEABr and PEAI (all in isopropanol). Then a glass substrate spin-coated with PbAc$_2$ film was placed over the substrate with lead PbAc$_2$-coated side facing down on the clean substrate. There is no intentional separation between the two pieces of substrates besides the very small gap caused by the rough PbAc$_2$ coating on the glass substrate. The reaction time was ~20 h.

Structural and morphological characterizations. Optical images were obtained on an Olympus BX51M optical microscope. The photoluminescence (PL) of single nanoplatelet was collected with an Aramis Confocal Raman microscope excited by a 442 nm laser. The sample was transferred to a Si substrate by a dry-transfer method prior to the PL measurement. SEM images were acquired on a LEO SUPRA 55 VP field-emission SEM operated at 3.0 kV. Energy-dispersive X-ray spectroscopy (EDX) was performed on single crystals transferred onto a Si wafer using a LEO 1530 field-emission SEM equipped with an EDS detector operating at 15.0 kV. PXRD data were collected using Cu Kα radiation on a Siemens STOE diffractometer (40 kV, 40 mA).

Results and Discussion

Figure 27:
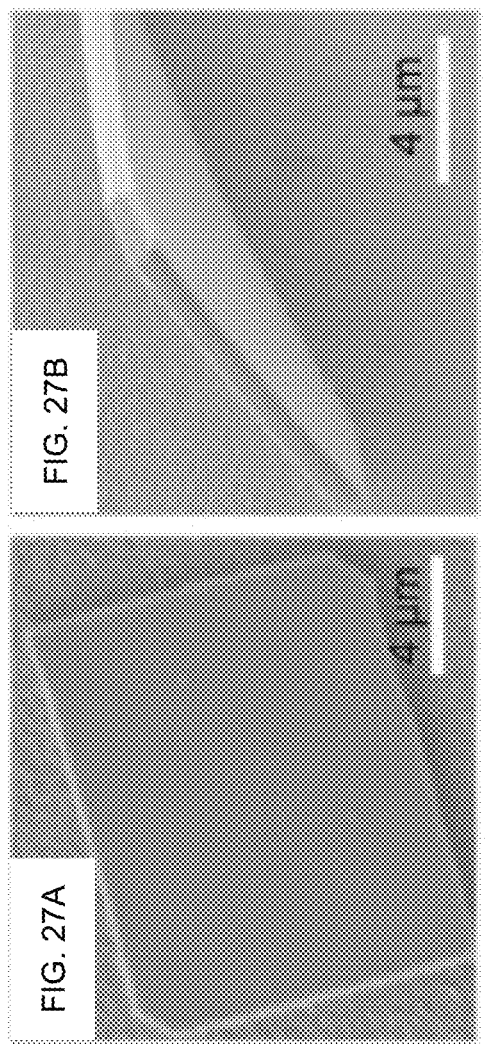
FIG. 27A shows a representative magnified SEM image of a (PEA)$_2$PbBr$_4$ nanoplatelet in a top-down view.
FIG. 27B shows a representative magnified SEM image of a standing (PEA)$_2$PbBr$_4$ nanoplatelet in a cross-section view.

Nanoplatelets of 2D layered perovskites with well-defined morphology can be grown by the method after some modifications on the PbAc$_2$ film deposition, precursor concentration and reaction time. It is important to note that glass substrates partially coated with PbAc$_2$ film were immersed in PEAX/IPA solution, with PbAc$_2$ coated side facing down to bottom. This is because it was found that well-defined nanoplatelets usually formed on the clean area of the substrate near the PbAc$_2$ film, while the products grown on PbAc$_2$ film often exhibited irregular rectangular shape with crystal defects. Herein, (PEA)$_2$PbBr$_4$ is used as an example to illustrate the nanoplatelets growth behaviors. Firstly, the effect of PEABr concentration on the crystal growth was investigated with the reaction time fixed at 1 h. Scanning electron microscopy (SEM) images of (PEA)$_2$PbBr$_4$ nanoplatelets grown using different concentrations of PEABr/IPA solution ranging from 1 mg/mL to 8 mg/mL, and the corresponding powder X-ray diffraction (PXRD) patterns were obtained (data not shown). At a low concentration of 1 mg/mL, only a few rectangular platelets were formed and sparsely distributed on the substrate. The yield of nanoplatelets increased with the concentration of PEABr. The PXRD patterns of the products grown using the concentration of ≥4 mg/mL show a group of strong diffraction peaks with regular spacings at 5.27°, 10.57°, 15.90°, and 21.26°, that could be well-assigned to the (001), (002), (003) and (004) lattice planes of the (PEA)$_2$PbBr$_4$ layered structure without other impurity peaks. However, peaks associated with PbAc$_2$ clearly showed that significant amount of PbAc$_2$ was unreacted at the low concentration of 1-2 mg/mL, suggesting a much slower reaction kinetics at lower concentration. Therefore, an optimized concentration to synthesize well-defined (PEA)$_2$PbBr$_4$ nanoplatelets that are suitable for nanophotonics and nanoelectronics is ≥4 mg/mL. Optical images of (PEA)$_2$PbBr$_4$ nanoplatelets grown using a 4 mg/mL PEABr solution for 2 h (data not shown). The size of as-grown nanoplatelets varies from several micrometers to tens of micrometers. FIG. 27A highlights an individual nanoplatelets with a dimension of ~10 μm×12 μm. FIG. 27B shows a nanoplatelet with a thickness of around 1 μm. The thickness of the plates typically varies from a few hundred nanometers to up to about 2 micrometers and can depend on the growth conditions and the locations of the plates on the substrates. Non-ideal rectangular nanoplatelets were obtained, typically showing evidence of a possible dislocation spiral (data not shown). Energy-dispersive X-ray spectroscopy (EDS) analysis on individual nanoplatelet yields a Br/Pb ratio of 4.2, in reasonable agreement with the stoichiometry of (PEA)$_2$PbBr$_4$. Further EDS mapping shows Br and Pb elements are uniformly distributed within the whole nanoplatelet (data not shown).

The effect of reaction time on the crystal growth of (PEA)$_2$PbBr$_4$ was then investigated, while the concentration of PEABr was fixed at 4 mg/mL. SEM images and PXRD patterns of (PEA)$_2$PbBr$_4$ nanoplatelets synthesized at a reaction time of 1 min, 5 min, 10 min, 45 min, 2 h, 5 h and 18.5 h, respectively, were obtained (data not shown). For comparison, the mophglgy of pre-coated PbAc$_2$ film on FTO glass was also obtained. After a short reaction of 1-5 min, the strong (001) diffraction peak at 5.27° confirms the formation of (PEA)$_2$PbBr$_4$ phase. The corresponding SEM images show small plate-like products with size of ~1 μm on the substrate, however their edges were not well-defined. After extending the reaction time to 10 min, the products start to display well-defined geometry and smooth surfaces. In general, the size and thickness of these platelets continued to increase with the reaction time. The corresponding PXRD patterns also show the dramatical increase of the (001) diffraction peak of (PEA)$_2$PbBr$_4$ as the reaction time increases, indicating the significant enhancement of crystallinity.

The crystal growth behaviors observed above can be well-explained by a dissolution-recrystallization mechanism as described in Example 1, above, that is the PbAc$_2$ precursor is first dissolved to form the PbBr$_4^{2-}$ complex ion in the solution and then recrystallize with organic cations to form (PEA)$_2$PbBr$_4$ crystals. The chemical reactions can be described as following:

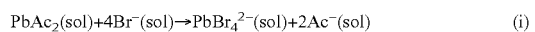
$$PbAc_2(sol)+4Br^-(sol) \rightarrow PbBr_4^{2-}(sol)+2Ac^-(sol) \quad (i)$$

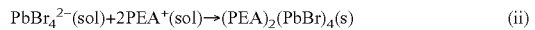
$$PbBr_4^{2-}(sol)+2PEA^+(sol) \rightarrow (PEA)_2(PbBr)_4(s) \quad (ii)$$

Without wishing to be bound to any particular theory, it is speculated that the local supersaturation of the PbBr$_4^{2-}$ complex can strongly affect the growth rate, crystal quality and morphology. As noted above, the free-standing nanoplatelets with well-defined geometry and flat facets were usually found in the clean regions (uncoated with PbAc$_2$) of the substrate neighboring the PbAc$_2$ film; on the other hand, the products grown on PbAc$_2$ film often exhibited complex over-growth with many dislocations and much disorder. The distinct growth behaviors are attributed to the difference of local supersaturation on the substrate. The relative high supersaturation on local PbAc$_2$ film could lead to fast crystal growth, resulting uncontrollable overgrowth. However, for the growth of well-defined microstructures, PbBr$_4^{2-}$ ions need diffuse to other areas (but close to the PbAc$_2$ source) where there remains low supersaturation of PbBr$_4^{2-}$ to recrystallize with organic cations to form (PEA)$_2$PbBr$_4$, which might enable the crystal growth in a more controllable way.

Figure 28:
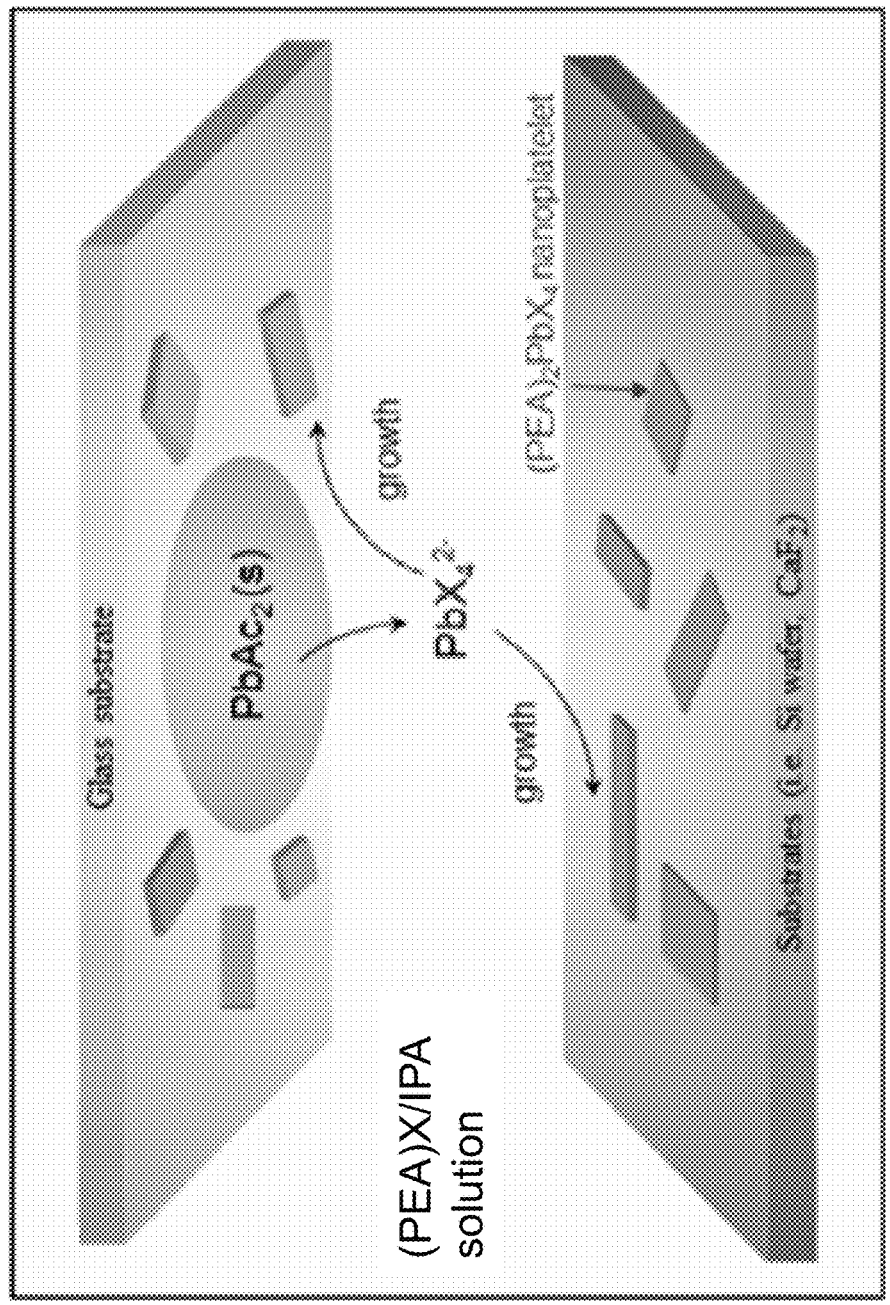
FIG. 28 show a schematic illustration of the solution transport growth process of 2D (PEA)$_2$PbBr$_4$ perovskite nanoplatelets by placing a glass substrate coated with PbAc$_2$ precursor over another clean (uncoated) substrate such as a silicon wafer.
Figure 29:
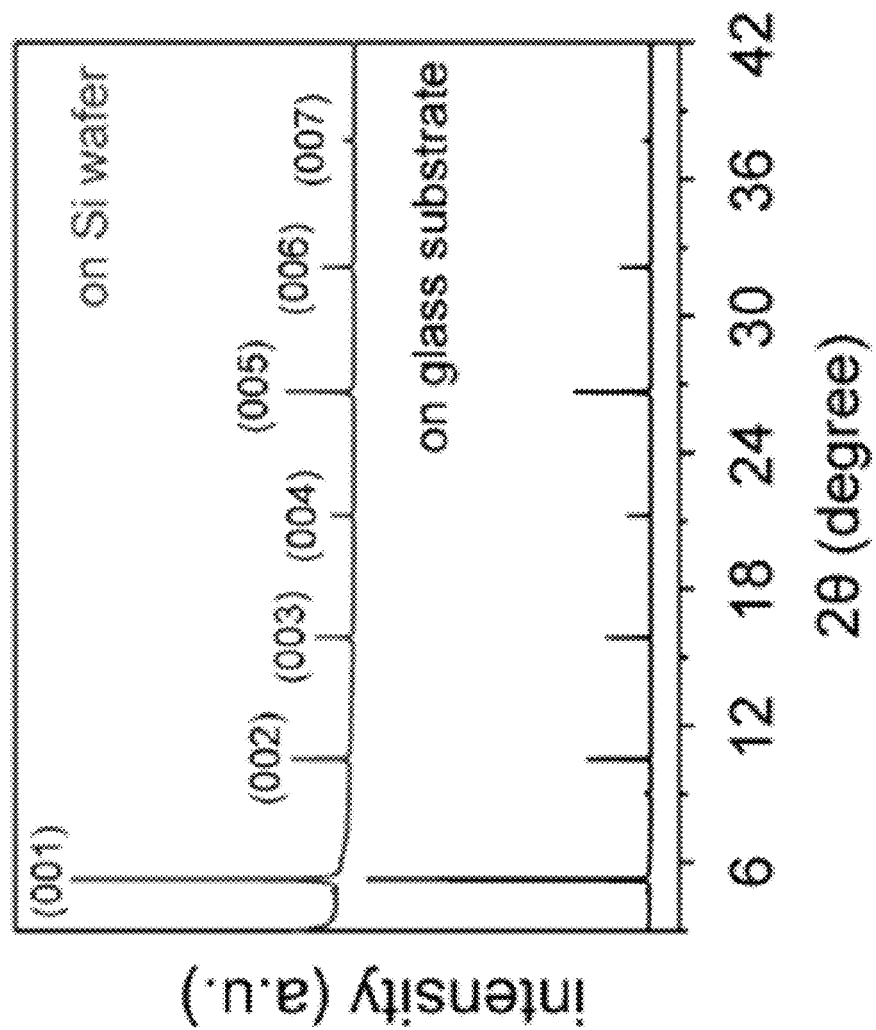
FIG. 29 shows the PXRD patterns of the (PEA)$_2$PbBr$_4$ perovskite nanoplatelets on the precursor substrate and the Si substrate.

To verify this hypothesis and further improve the control of crystal growth, a solution transport crystal growth process was designed to directly grow these nanoplatelets on another clean substrate (i.e. uncoated with PbAc$_2$ precursor film) by placing the PbAc$_2$ film coated glass slide over a silicon wafer (or CaF$_2$ substrate), as illustrated in FIG. 28. In this process, the perovskite products formed on the product substrate must have gone through the solution between the two substrates via the dissolution-recrystallization process, hence the name of "solution transport crystal growth". As shown in FIG. 29, the PXRD patterns of the products on both precursor substrate and Si substrate grown at 10 mg/mL PEABr for 19 h show identical diffraction peaks associated with (PEA)$_2$PbBr$_4$. Optical and SEM images of (PEA)$_2$PbBr$_4$ nanoplatelets with rectangular shape and smooth surface grown on both the clean area of precursor substrate and Si substrate were obtained (data not shown). Even though (PEA)$_2$PbBr$_4$ microstructures can still be observed on the precursor substrate in the region originally coated with PbAc$_2$ precursor, they have much more disorder and poorly controlled morphology and size. The growth of perovskite nanostructures on an opposing substrate clearly confirms the hypothesis above and the dissolution-recrystallization process. FIGS. 30A-B highlight individual nanoplatelets with well-defined geometry grown on the Si substrate. The structures can also be grown via the solution transport growth process on other arbitrary substrates, for example CaF$_2$ substrate (data not shown). Typically, the size of these nanoplatelets on Si substrate varies from a few micrometers to ~a few hundred micrometers (data not shown). Atomic force microscopy (AFM) revealed that the thickness of these nanoplatelets grown via the solution transport process ranges from tens of nanometers to a few micrometers (data not shown). The large variation in dimension among these nanoplatelets can be explained by the facts that the nucleation to initiate the growth of each nanoplatelet might appear at different times and the local supersaturation of the PbBr$_4^{2-}$ are spatially dependent.

More interestingly, the AFM images (data not shown) further revealed the presence of screw dislocation growth spirals on the surface some nanoplatelets. Without wishing to be bound to any particular theory, it is believed that this observation confirms the screw-dislocation driven growth mechanism of these 2D layered materials. However, the formation of pyramid structure without dislocation core was also observed (data not shown), suggesting the presence of layer-by-layer growth mechanism.

The nanostructure growth can be expanded to other 2D (PEA)$_2$PbX$_4$ perovskite analogues and their alloys. For example, single-crystal nanoplatelets of (PEA)$_2$PbI$_4$ were also synthesized through the solution transport growth method by replacing the precursor solution of PEABr with PEAI. It was observed that low concentration of PEAI leads to slow reaction kinetics and incomplete conversion, resulting a low yield of (PEA)$_2$PbI$_4$ and the formation of PbI$_2$ crystals (data not shown). This is because low concentration of I$^-$ ion will limit the formation of PbI$_4^{2-}$ complex to reach a proper concentration. Therefore, under such a condition, the growth of other phases could become more thermodynamically favorable. With increasing I$^-$ concentration, the growth of (PEA)$_2$PbI$_4$ becomes dominated due to the increasing amount of PbI$_4^{2-}$ complex in the solution. However, even higher concentration of PEAI could lead to uncontrollable crystal growth. SEM images of (PEA)$_2$PbI$_4$ microstructures grown using a PEA/IPA solution with a proper concentration of 15 mg/mL for ~20 h were obtained (data not shown). Magnified optical images (data not shown) of individual free-standing nanoplatelets and microrods with well-defined morphology were obtained. Images also revealed microstructures with rectangular cross section and flat facets. The size of these microstructures is around 10-100 μm with a thickness varies from hundreds nanometer to a few micrometer, depending on the reaction time, precursor concentration, and the growth area on the substrate. EDS analysis carried out on individual microstructures confirmed a stoichiometry of (PEA)$_2$PbI$_4$ (data not shown).

Also successfully synthesized were single-crystal microstructures of a series of halide alloys of the 2D perovskite (PEA)$_2$Pb(Br,I)$_4$ through the solution transport crystal growth by using mixed solutions of PEABr and PEAI precursors with different ratios. Representative SEM images of the microstructures of (PEA)$_2$Pb(Br,I)$_4$ alloys grown on precursor substrate using a mixed precursor solution of PEABr at 6 mg/mL and PEAI at 9 mg/mL (data not shown) revealed that the as-grown microstructures are often formed in irregualar shapes and in dense clusters. However, SEM and optical images (data not shown) of microstructures grown via the solution transport growth on the Si substrate exhibit more defined shape and are more sparsely dispersed. Interestingly, unlike pure (PEA)$_2$PbI$_4$ or (PEA)$_2$PbBr$_4$, it was found that the use of mixed precursor solution tended to promote the growth of other morphologies beyond rectangles, such as hexagonal, rhombic and octagonal structures. EDS analysis (data not shown) of an indivial hexgonal nanoplatelet confirmed the successful alloying of Br and I, yielding an estimated stiochimetry of (PEA)$_2$PbBr$_{2.4}$I$_{1.6}$. PXRD patterns of the alloy nanostructures grown using different ratios of Br/I in the precusror solution were also obtained (data not shown). Interestingly, it was noticed that the (00l) peaks (corresponds to c lattice parameter) changes discontinuously with incresing Br/I ratio. A sudden shift of the (00l) peaks was observed in the alloy of (PEA)$_2$PbBr$_{2.4}$I$_{3.4}$(the ratio was detemined by EDS analysis), but then remained unchanged as the Br content further increased. The unusual trend has been observed in the thin films of (PEA)$_2$Pb(Br,I)$_4$ alloys, which may be explained by the varying c lattice constants in the (PEA)$_2$PbX$_4$ crystal structures due to a sudden changing conformations of PEA group in these alloys.

Figure 31:
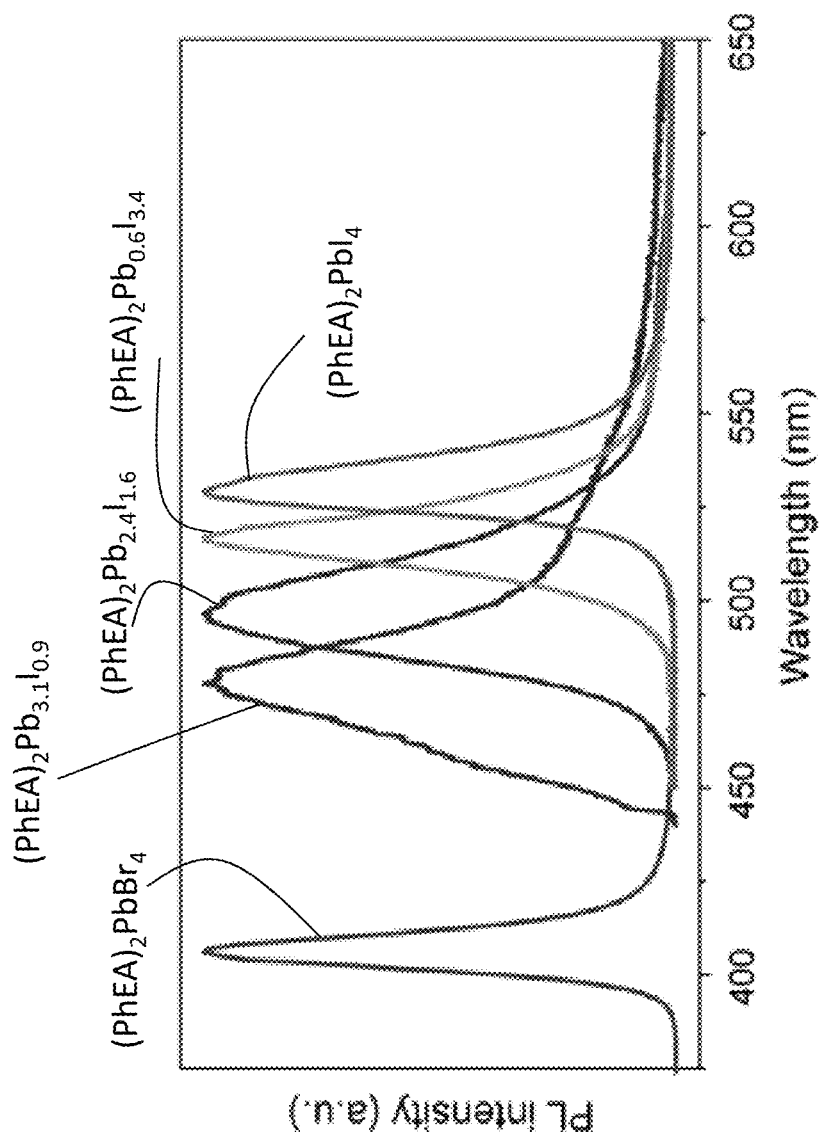
FIG. 31 shows the confocal microscopy photoluminescence spectra of individual (PEA)$_2$Pb(Br,I)$_4$ microstures excited by a 442 nm laser source at room temperature. Note the PL spectra of (PEA)$_2$PbBr$_4$ was collected on the sample at Si substrate excited by 365 nm.

As a result of quantum confinement, these layered perovskites exhibit several attractive photophysical features, such as high quantum efficiency, high color purity (narrow emission bandwidth), and controllable color tunablity, for lighting and display applications. Preliminary optical studies that show that these single-crystal (PEA)$_2$PbX$_4$ layered perovskite microstructures have strong room temperature photoluminescence with a small full-width-at-half-maximum (FWHM). PL spectra collected on the as-grown (PEA)$_2$PbBr$_4$ and (PEA)$_2$PbI$_4$ nanoplatelets on Si substrate show a band edge emission centered at 406 nm and 529 nm, with a FWHM of ~11 nm and ~17 nm, respectively. Moreover, as shown in FIG. 31, the PL spectra collected on individual nanoplatelets with different stoichiometry show a continuous blue shift from green to violet with increasing Br content, in agreement with the increasing bandgap due to the alloying of the Br into the (PEA)$_2$PbI$_4$. As shown in FIGS. 32A-E, a series of optical images of these alloy microstructures excited by a 442 nm CW laser clearly demonstrate tunable emissions and strong waveguiding effect among these microstructures. Interestingly, it was noticed that the PL spectra of the (PEA)$_2$PbX$_4$ microstructures grown on precursor substrates are characterized by a more asymmetric shape with clear PL tails, which might indicate higher extonic trap density, compared to the microstructures grown on Si substrate. Also noticed was an increase of full-width-at-half-maximum (FWHM) of the PL peaks with the increase of the Br content in these alloys, which might be due to the increased inhomogeneity arising from structural and chemical disorder.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A method for growing single-crystal perovskite structures, the method comprising immersing a film of a metal precursor compound on a surface of a substrate, the metal precursor compound comprising a metal ion B, in a solution comprising a cation precursor compound, the cation precursor compound comprising a cation ion A and an anion X, at a concentration of the cation precursor compound, a growth time, and a growth temperature sufficient to dissolve the film to release the metal ion B into the solution to form an intermediate complex with the anion X in the solution and sufficient to induce recrystallization of the intermediate complex with the cation ion A out of the solution to form a plurality of single-crystal perovskite structures composed of A, B and X,
   wherein the structures of the plurality of single-crystal perovskite structures are elongated structures having opposing end facets which are substantially parallel to one another and substantially perpendicular to a longitudinal axis of the elongated structure,
   and further wherein the perovskite of the perovskite structures has a formula ABX$_3$, wherein A, the cation ion, is a protonated amine comprising an organic group; B, the metal ion, is selected from Pb$^{2+}$, Sn$^{2+}$, and Ge$^{2+}$; and X, the anion, is a halide; or further wherein perovskite of the perovskite structures has formula $A_2BX_4$, wherein A, the cation ion, is selected from $C_{n1}H_{2n1+1}NH_3^+$, wherein $n_1$ is 3 or greater; $Cn_2H_{2n2-1}C_{n3}H_{2n3}NH_3^+$, wherein $n_2$ is 3 or greater and wherein $n_3$ is 0 or greater; and $C_6H_5C_{n4}H_{2n4}NH_3^+$, wherein $n_4$ is 0 or greater; B, the metal ion, is selected from $Pb^{2+}$, $Sn^{2+}$, and $Ge^{2+}$; and X, the anion, is a halide.

2. The method of claim 1, wherein the perovskite of the perovskite structures has the formula $ABX_3$.

3. The method of claim 1, wherein the perovskite of the perovskite structures has the formula $ABX_3$, and further wherein A is selected from a primary ammonium and an iminium.

4. The method of claim 3, wherein A is selected from methylammonium, formamidinium, and phenethylamine; and X is selected from $F^-$, $I^-$, $Br^-$ and $Cl^-$.

5. The method of claim 1, wherein the film is positioned to oppositely face a surface of a second substrate and the plurality of single-crystal perovskite structures are formed on the surface of the second substrate.

6. The method of claim 5, wherein the perovskite of the perovskite structures has the formula $A_2BX_4$.

7. The method of claim 6, wherein A is selected from phenethylamine and cyclohexylamine.

8. The method of claim 1, wherein the structures comprise plates, belts, rods, wires, tubes or combinations thereof.

9. The method of claim 1, wherein the structures are characterized by an average aspect ratio of 10 or greater.

10. The method of claim 9, wherein the structures are characterized by an average thickness t or average diameter d in the range of from about 50 nm to about 10 µm.

11. The method of claim 10, wherein the structures are characterized by an average thickness t or average diameter d in the range of from about 50 nm to about 1 µm.

12. The method of claim 1, wherein the structures are nanowires configured to produce lasing action when the nanowires are under the influence of an applied electromagnetic field.

13. The method of claim 1, wherein the concentration of the cation precursor compound is sufficiently high to dissolve the film of the metal precursor compound, but sufficiently low such that the perovskite is able to crystallize out of the solution.

14. The method of claim 1, wherein the growth temperature is room temperature or no more than about 40° C. above room temperature.

15. The method of claim 1, wherein the elongated structures of the plurality of single-crystal perovskite structures are each composed of a plurality of facets, the opposing end facets being ones of the plurality of facets, wherein neighboring facets of the plurality of facets meet at substantially sharp edges.

16. The method of claim 1, further comprising collecting the plurality of single-crystal perovskite structures from the surface of the substrate.

17. A method for growing single-crystal perovskite structures, the method comprising immersing a film of a metal precursor compound on a surface of a substrate, the metal precursor compound comprising a metal ion B, in a solution comprising a cation precursor compound, the cation precursor compound comprising a cation ion A and an anion X, at a concentration of the cation precursor compound, a growth time, and a growth temperature sufficient to dissolve the film to release the metal ion B to form a complex with the anion X and sufficient to induce recrystallization of the complex with the cation ion A to form a plurality of single-crystal perovskite structures composed of A, B and X, wherein the structures are nanowires configured to produce lasing action when the nanowires are under the influence of an applied electromagnetic field, and further wherein the nanowires are characterized by a rectangular cross-section or a hexagonal cross-section;

and further wherein the perovskite of the perovskite structures has a formula $ABX_3$, wherein A, the cation ion, is a protonated amine comprising an organic group; B, the metal ion, is selected from $Pb^{2+}$, $Sn^{2+}$, and $Ge^{2+}$; and X, the anion, is a halide; or further wherein perovskite of the perovskite structures has formula $A_2BX_4$, wherein A, the cation ion, is selected from $C_{n1}H_{2n1+1}NH_3^+$, wherein $n_1$ is 3 or greater; $Cn_2H_{2n2-1}C_{n3}H_{2n3}NH_3^+$, wherein $n_2$ is 3 or greater and wherein $n_3$ is 0 or greater; and $C_6H_5C_{n4}H_{2n4}NH_3^+$, wherein $n_4$ is 0 or greater; B, the metal ion, is selected from $Pb^{2+}$, $Sn^{2+}$, and $Ge^{2+}$; and X, the anion, is a halide.

18. A method for growing single-crystal perovskite structures, the method comprising immersing a film of a metal precursor compound on a surface of a substrate, the metal precursor compound comprising a metal ion B, in a solution comprising a cation precursor compound, the cation precursor compound comprising a cation ion A and an anion X, at a concentration of the cation precursor compound, a growth time, and a growth temperature sufficient to dissolve the film to release the metal ion B to form a complex with the anion X and sufficient to induce recrystallization of the complex with the cation ion A to form a plurality of single-crystal perovskite structures composed of A, B and X, wherein the structures are nanowires configured to produce lasing action when the nanowires are under the influence of an applied electromagnetic field, and further wherein the nanowires have end facets configured to provide a Fabry-Perot optical cavity;

and further wherein the perovskite of the perovskite structures has a formula $ABX_3$, wherein A, the cation ion, is a protonated amine comprising an organic group; B, the metal ion, is selected from $Pb^{2+}$, $Sn^{2+}$, and $Ge^{2+}$; and X, the anion, is a halide; or further wherein perovskite of the perovskite structures has formula $A_2BX_4$, wherein A, the cation ion, is selected from $C_{n1}H_{2n1+1}NH_3^+$, wherein $n_1$ is 3 or greater; $Cn_2H_{2n2-1}C_{n3}H_{2n3}NH_3^+$, wherein $n_2$ is 3 or greater and wherein $n_3$ is 0 or greater; and $C_6H_5C_{n4}H_{2n4}NH_3^+$, wherein $n_4$ is 0 or greater; B, the metal ion, is selected from $Pb^{2+}$, $Sn^{2+}$, and $Ge^{2+}$; and X, the anion, is a halide.

19. A single-crystal perovskite structure configured to produce lasing action when under the influence of an applied electromagnetic field, wherein the perovskite has formula $ABX_3$, wherein A is a protonated amine comprising an organic group; B is selected from $Pb^{2+}$, $Sn^{2+}$, and $Ge^{2+}$; and X is a halide;

or the perovskite has formula $A_2BX_4$, wherein A is selected from $C_{n1}H_{2n1+1}NH_3^+$, wherein $n_1$ is 3 or greater; $Cn_2H_{2n2-1}C_{n3}H_{2n3}NH_3^+$, wherein $n_2$ is 3 or greater and wherein $n_3$ is 0 or greater; and $C_6H_5C_{n4}H_{2n4}NH_3^+$, wherein $n_4$ is 0 or greater; B is selected from $Pb^{2+}$, $Sn^{2+}$, and $Ge^{2+}$; and X is a halide, wherein the single-crystal perovskite structure is an elongated structure having opposing end facets which are configured to provide a Fabry-Perot optical cavity.

20. The single-crystal perovskite structure of claim 19, wherein the elongated structure is a nanowire.

21. The single-crystal perovskite structure of claim 19, wherein the elongated structure is a nanoplate.

* * * * *